(12) United States Patent
Leunis et al.

(10) Patent No.: US 8,586,569 B2
(45) Date of Patent: Nov. 19, 2013

(54) BETULONIC AND BETULINIC ACID DERIVATIVES

(75) Inventors: Jean-Claude Leunis, Wavre (BE); Emmanuel Couche, Wavre (BE)

(73) Assignee: Jean-Claude Leunis, Bonlez (BE)

( * ) Notice: Subject to any disclaimer, the term of this patent is extended or adjusted under 35 U.S.C. 154(b) by 1051 days.

(21) Appl. No.: 12/204,354

(22) Filed: Sep. 4, 2008

(65) Prior Publication Data
US 2009/0068257 A1 Mar. 12, 2009

Related U.S. Application Data

(63) Continuation of application No. PCT/EP2007/052154, filed on Mar. 7, 2007.

(30) Foreign Application Priority Data

Mar. 7, 2006 (GB) .................................. 0604535.5

(51) Int. Cl.
*A61K 31/56* (2006.01)
*A61K 31/58* (2006.01)
*C07J 43/00* (2006.01)
*C07J 53/00* (2006.01)

(52) U.S. Cl.
USPC ........................... 514/182; 514/176; 552/510

(58) Field of Classification Search
USPC .................................. 514/176, 182; 552/510
See application file for complete search history.

(56) References Cited

U.S. PATENT DOCUMENTS

| 6,403,816 B1 | 6/2002 | Jaggi et al. |
| 6,670,345 B1 | 12/2003 | Ramadoss |

FOREIGN PATENT DOCUMENTS

| WO | WO 00/46235 | 8/2000 |
| WO | WO 01/18029 | 3/2001 |
| WO | WO 02/16395 | 2/2002 |

OTHER PUBLICATIONS

Hashimoto et al. "Anti-AIDS Agents. XXVII. synthesis and Anti-HIV Activity of Betulinic Acid and Dihydrobetulinic Acid Derivatives" Biological & Medicinal Chemistry 5(12) 1997 2133-2143 XP002102686.

Hata et al. "Anti-leukemia activities of Lup-28-al-20(29)-en-3-one, a lupane triterpene" Toxicology Letters 143(1) 2003:1-7 XP002441650.

Hata et al. "Differentiation- and Apoptosis-Inducing Activities by Pentacyclic Triterpenes on a Mouse Melanoma Cell Line" Journal of Natural Products 2002 65(5):645-648 XP002967006.

Kashiwada et al. "Synthesis and anti-HIV activity of 3-alkylamido-3-deoxy-betulinic acid derivatives" Chemical & Pharmaceutical Bulletin SEP 2000;48(9):1387-1390 XP002441649.

Ku et al. "A novel secobetulinic acid 3,4-lactose from *Viburnum aboricolum*" Helvetica Chimica Acta 86(3) 2003:697-702. XP002441647.

Mahato et al. "Reactions in High Boiling Solvent II Effect of Raney Nickel on Triterpenoids" Tetrahedron 27(1) 1971:177-186 XP002441648.

Pellizzaro et al "Cholesteryl Butyrate in Solid Lipid Nanospheres as an Alternative Approach for Butyric Acid Delivery" Anticancer Research Helenic Anticancer Institute 1999:19(58)3921-3926 XP008068752.

Sorokina et al. "Betulonic acid and derivatives, a new group of agents reducing side effects of cytostatics" Doklady Biological Sciences: Proceedings of the Academy of Sciences of the USSR, Biological Sciences Section 2004 399:434-437.

Urban et al. "Influence of esterification and modification of A-ring in a group of lupane acids on their cytotoxicity" Bioorganic & Medicinal Chemistry 2005 13(19) 5527-5535 XP005038808.

Urban et al. "Synthesis of A-seco derivatives of betulinic acid with cytotoxic activity" Journal of Natural Products 2004 67(7):1100-1105 XP002441651.

*Primary Examiner* — Barbara P Badio
(74) *Attorney, Agent, or Firm* — Fulbright & Jaworski LLP; Scott D. Rothenberger; Colin L. Fairman

(57) ABSTRACT

The present invention relates to betulonic and betulinic acid derivatives and, in particular, to C-28 and C-3 derivatives. The present invention relates to betulonic acid esters, dihydro-betulonic acid esters, PAG-modified betulinic acid derivatives, and PAG-modified dihydro-betulinic acid derivatives. Betulinic acid and derivatives thereof may be bound to a poly(alkylene glycol) (PAG) such as poly(ethylene glycol). Binding may be via a linker, such as a diamine, an amino acid, a peptide, an ester or a carbonate.

The compounds of the present invention may be used for the treatment of cancer or a viral infection. The present invention also provides pharmaceutical compositions comprising the compounds of the present invention. The present invention further provides processes for the preparation of the compounds of the present invention, for example, from betulin.

6 Claims, 10 Drawing Sheets

PAG carbamate

PAG succinimide derivative,
wherein Y = O or NH, and n = 2, 3, 4 or 5

PAG camphorquinone derivative,
wherein Y = O or NH

PAG succinimide derivative

PAG phenylglyoxal derivative

PAG imidazole derivative

PAG maleimide derivative,
wherein n = 1, 2, 3, 4, 5 or 6

PAG carbonates, wherein R =

PAG triazine derivative

PAG azide derivative

PAG sulfonates, wherein R =

PAG xanthate derivative

PAG imidoester

PAG ester,
wherein X = Cl or I,
and n = 1, 2, 3, 4, 5 or 6

PAG carboxylic acid,
wherein n = 1, 2, 3, 4, 5 or 6

PAG vinylsulfone derivative

PAG maleimide derivative

PAG iodoacetamide derivative

PAG—(CH$_2$)$_n$—CHO

PAG aldehyde derivative,
wherein n = 1, 2, 3, 4, 5 or 6

PAG orthopyridyl disulfide derivative

BETULONIC AND BETULINIC ACID DERIVATIVES

CROSS-REFERENCE TO RELATED APPLICATIONS

This application is a continuation of International Patent Application No. PCT/EP2007/052154, filed on Mar. 7, 2007, which claims priority to Great Britain Application No. 0604535.5, filed on Mar. 7, 2006, the entire contents of both of which are incorporated herein by reference.

FIELD OF THE INVENTION

The present invention relates to betulonic and betulinic acid derivatives and, in particular, to C-28 and C-3 derivatives. The present invention relates to betulonic acid esters, dihydro-betulonic acid esters, PAG-modified betulinic acid derivatives, and PAG-modified dihydro-betulinic acid derivatives. Betulinic acid and derivatives thereof may be bound to a poly(alkylene glycol) (PAG) such as poly(ethylene glycol). Binding may be via a linker, such as a diamine, an amino acid, a peptide, an ester or a carbonate.

The compounds of the present invention may be used for the treatment of cancer or a vital infection. The present invention also provides pharmaceutical compositions comprising the compounds of the present invention. The present invention further provides processes for the preparation of the compounds of the present invention, for example, from betulin.

BACKGROUND OF THE INVENTION

Betulinic acid (BetA) and betulin come from a variety of botanical sources such as bark from *Betula alba*, *Platanus orientalis*, *Corylus avellana*, *Carpinus betulus*, *Alnus glutinosa* as well as from *Ziziphus* sp. Rhamnaceae (Jiri Patocka, *Journal of Applied Biomedicine*, 2003, 1, 7-12. E. L. Ménard et al., *Helvetica Chimica Acta*, 1963, XLVI, 1801-1811).

BetA is thus found in many plant species, although in a low concentration compared to betulin. The rare exception is the rich content of BetA in a clover species named *Menyanthes trifoliate*, which is a bog plant (C. Huang et al., *Yao Xue Xue Bao*, 1995, 30, 621-626).

Methods of synthesis of many derivatives of BetA and betulonic acid have been described, including amino acid and amide derivatives (Darrick S. H. L. Kim et al., *Bioorganic & Medicinal Chemistry Letters*, 1998, 8, 1707-1712. O. B. Flekhter et al., in *Bioorg Khim.*, 2004, 30, 89-98; and in *Russian Journal of Bioorganic Chemistry*, 2004, 30, 80-88), as well as hydrophobic derivatives.

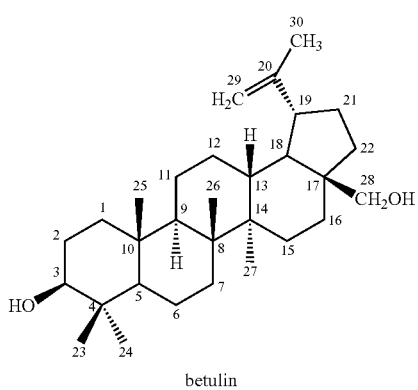

betulin

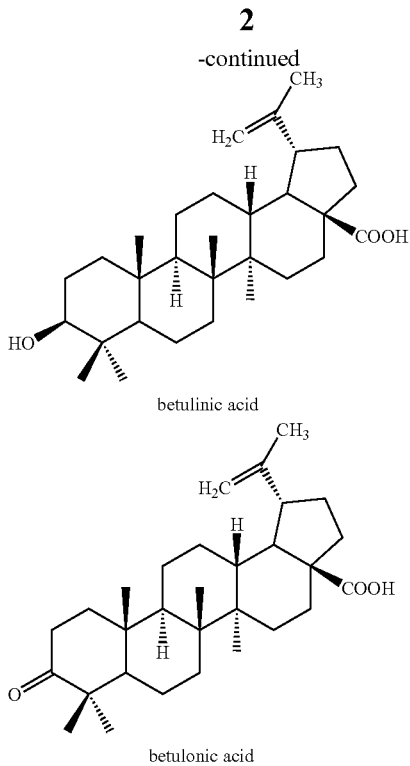

betulinic acid betulonic acid

A cyclopropane derivative of betulin has been converted by oxidation into the corresponding BetA and betulonic acid derivatives. The 20,29-dihydro-20,29-dichloromethylene betulinic acid proved to be the most cytotoxic toward human melanoma and human ovarian carcinoma cell lines (A. V. Symon et al. in *Bioorg. Khim.*, 2005, 31, 320-325; and in *Russian Journal of Bioorganic Chemistry*, 2005, 31, 286-291).

The potential value of triterpenoids, especially pentacyclic triterpenes like betulin and BetA, in the induction of apoptosis in malignant tumour cells has been recognised for some years now (Emily Pisha et al., *Nature Medicine*, 1995, 1, 1046-1451. Simone Fulda et al., in *Cancer Res.*, 1997, 57, 4956-4964; in *J. Biol. Chem.*, 1998, 273, 33942-33948; and in *Int. J. Cancer*, 1999, 82, 435-441).

BetA demonstrates selective cytotoxicity against melanoma cells and other malignant cells of neuroectodermal origin (Tino Galgon et al., *Exp. Dermatol.*, 2005, 14, 736-743). Growth inhibition is evident in all neoplastic cell lines and is independent of the status of the apoptotic inducer protein, p53 (Valentina Zuco et al., *Cancer Lett.*, 2002, 175, 17-25).

Tumoural tissue grows when the equilibrium between cell replication and cell death (apoptosis) is not maintained. The immunological mechanisms that control such cellular cycles are complex, being based on the activity of a variety of cytokines as well as on the expression of certain genes.

Two genes are of primary importance:
1. The gene p53, called tumour-suppressor, which codes for the apoptotic inducer protein, p53; and
2. The gene Bcl-2, a proto-oncogene encoding the Bcl-2 family of proteins. Bcl-2 proteins inhibit apoptosis by inhibiting caspase activities. Failure in cancer therapy has been linked to high expression of the Bcl-2 gene (D. Maslinska, *Neurol. Neurochir. Pol.*, 2003, 37, 315-326; A. Linjawi et al., *J. Am. Coll. Surg*, 2004, 198, 83-90; J. Huang et al., *Biol. Pharm. Bull.*, 2005, 28, 2068-2074).

In addition to this genetic regulation, different membrane proteins play a part in the control of the cell cycle by acting as receptors for cytokines that regulate apoptosis. Among these cytokines are tumour necrosis factor (TNF) and nerve growth factor (NGF). The binding of such cytokines to their specific receptors induces the activation of caspases, which in turn leads to the proteolysis of a variety of substrates including the nuclear enzyme, poly(ADP-ribose) polymerase (PARP). Hydrolysis of PARP induces apoptosis. It is important to note that this mechanism by-passes the proto-oncogene, Bcl-2 (the protein products of which inhibit caspase activities).

The mitochondrion also plays an important role in apoptosis. In 1998, S. Fulda et al. described BetA as a cytotoxic agent that triggers apoptosis by a direct effect at the mitochondrial membrane level, even when the caspases are chemically inhibited (*J. Biol. Chem.*, 273, 33942-33948). BetA directly induced loss of mitochondrial transmembrane potential; soluble cytochrome c excreted in the cytoplasm of the cell thus activated caspases 9 and 3 leading to apoptosis. Action of BetA is thus Bcl-2 independent (V. Zuco et al., *Cancer Lett.*, 2002, 175, 17-25).

In 1999, S. M. Swanson et al. suggested that metabolism of BetA is not necessary for the induction of apoptosis in melanoma cells and that metabolites of BetA are not responsible for its specificity in inducing apoptosis in cancer cells (S. M. Swanson et al., *Proc. Amer. Assoc. Cancer Res., March* 1999, 40).

Recently, BetA was recognised as a selective inhibitor of human melanoma growth and was reported to induce apoptosis of these cells (Darrick S. H. L. Kim et al., *Bioorganic & Medicinal Chemistry Letters,* 1998, 8, 1707-1712; E. Pisha et al., *Nature Medicine,* 1995, 1, 1046-1051; S. Fulda et al., *Cancer Res.*, 1997, 57, 4956-4964). The growth inhibitory action of BetA was more effective against melanoma cell lines than against normal melanocytes. This was recently confirmed in mice bearing human melanoma xenografts (D. A. Eiznhamer and Z. Q. Xu, *Drugs,* 2004, 7, 359-373).

The anti-proliferative action of BetA seems to be independent of the p53 status and, despite the induction of apoptosis, the expression of the anti-apoptotic protein Mcl-1 is induced (Edgar Selzer et al., *Journal of Investigative Dermatology,* 2000, 114, 935-940).

Furthermore, a recent publication indicates that BetA activates the transcription factor NF-kappaB in a variety of tumour cell lines and induces apoptosis in a cell-type dependent manner (Hubert Kasperczyk et al., *Oncogene,* 2005, 24, 6945-6956).

Another study showed that BetA suppresses NF-kappaB activation as well as NF-kappaB regulated gene expression induced by carcinogens, TNF, interleukin-1 (IL-1) and oxidative stress (Yasunari Takada, Bharat B. Aggarwal, *J. Immunol.*, 2003, 171, 3278-3286).

The inhibition of HIV-1 replication by BetA and some other triterpenoids has also been described (Erik De Clercq, *Rev. Med. Virol.,* 2000, 10, 255-277. Chaomei Ma et al., *Chem. Pharm. Bull. (Tokyo),* 1999, 47, 141-145. Taisei Kanamoto et al., *Antimicrob. Agents Chemother.,* 2001, 45, 1225-1230).

A new derivative, 3-O-(3',3'-dimethylsuccinyl)-betulinic acid (DSB), blocks HIV-1 maturation by inhibiting the cleavage of the capsid precursor, CA-SP1, which leads to a defect in viral core condensation of the viral particles (Donglei Yu et al., *Expert Opin. Investig. Drugs,* 2005, 14, 681-693).

Recently, Boc-lysinated betulonic acid has been found to be useful in the treatment of cancer, in particular prostate cancer (Brij B. Saxena, *Bioorganic & Medicinal Chemistry Letters*, 2006, 14, 6349-6358).

A recent review article by R. Mukherjee et al. (*Anti-Cancer Agents in Medicinal Chemistry,* 2006, 6, 271-279) studies the structure activity relationship of a number of betulinic acid derivatives. The paper concludes that the C-28 carboxylic acid functionality is essential for eliciting cytotoxicity, that a C-3 ester functionality enhances cytotoxicity, and that a C-2 halo-substituent improves cytotoxicity.

Nevertheless, there is of course always a need for alternative compounds for the treatment of diseases such as cancer and viral infections.

It has now been found that betulonic acid derivatives, in particular betulonic acid esters, dihydro-betulonic acid esters, PAG-modified betulinic acid derivatives, and PAG-modified dihydro-betulinic acid derivatives, are useful in the treatment of cancer and viral infections such as HIV, HSV and influenza infection. The ketone functionality of the betulonic acid esters and the dihydro-betulonic acid esters allows these esters to be derivatised and bound to a poly(alkylene glycol), for example, poly(ethylene glycol) or monomethoxy poly (ethylene glycol), which provides the esters with improved solubility and stability in vivo.

SUMMARY OF THE INVENTION

In a first aspect, the present invention provides a compound having the structure (I):

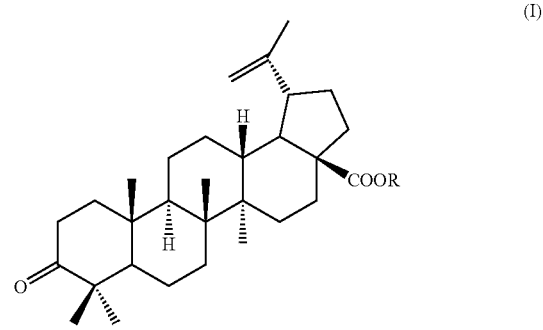

(I)

wherein R is an alkyl, alkenyl, alkynyl, aryl, arylalkyl, arylalkenyl, arylalkynyl, alkylaryl, alkenylaryl or alkynylaryl group, which may optionally be substituted, which may optionally include one or more heteroatoms N, O or S in its carbon skeleton, and which may optionally include one or more carboxy groups —CO— in its carbon skeleton, provided that R is not —CH$_3$, —CH$_2$—C$_6$H$_5$, —CH$_2$—O—CO—C(CH$_3$)$_3$, —CH$_2$—O—CO—CH$_3$,

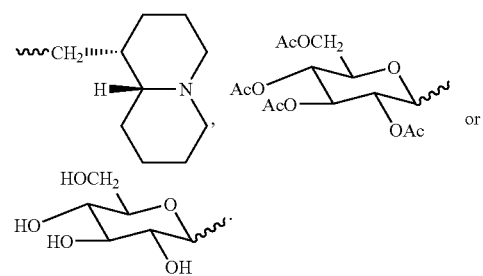

The first aspect of the present invention also provides a compound having the structure (II):

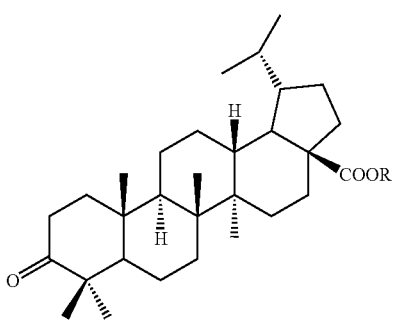

(II)

wherein R is an alkyl, alkenyl, alkynyl, aryl, arylalkyl, arylalkenyl, arylalkynyl, alkylaryl, alkenylaryl or alkynylaryl group, which may optionally be substituted, which may optionally include one or more heteroatoms N, O or S in its carbon skeleton, and which may optionally include one or more carboxy groups —CO— in its carbon skeleton, provided that R is not

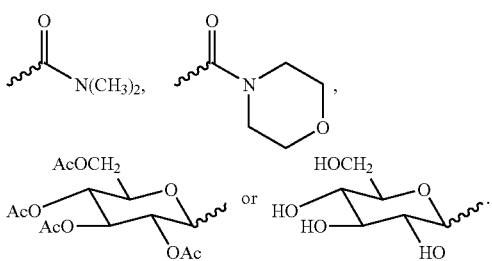

For the purposes of the present invention, an "alkyl" group is defined as a monovalent saturated hydrocarbon, which may be straight-chained or branched, or be or include one or more cyclic groups. An alkyl group may optionally include one or more heteroatoms N, O or S in its carbon skeleton. Preferably an alkyl group includes 0, 1, 2, 3 or 4 nitrogen atoms in its carbon skeleton. Preferably an alkyl group includes 0, 1, 2, 3 or 4 oxygen atoms in its carbon skeleton. Preferably an alkyl group includes 0, 1, 2, 3 or 4 sulphur atoms in its carbon skeleton. An alkyl group may optionally include one or more carboxy groups —CO— in its carbon skeleton. Preferably an alkyl group includes 0, 1, 2, 3 or 4 carboxy groups —CO— in its carbon skeleton, more preferably an alkyl group does not include any carboxy groups —CO— in its carbon skeleton. Examples of alkyl groups are methyl, ethyl, cyclohexyl and decahydro-naphthalene groups. Preferably an alkyl group is a $C_2$-$C_{30}$ alkyl group, which is defined as an alkyl group containing from 2 to 30 carbon atoms. An "alkylene" group is similarly defined as a divalent alkyl group. In one embodiment, an alkyl group is or includes one or more cyclic groups and contains 17 to 25 carbon atoms. In another embodiment, an alkyl group is straight-chained or branched and contains 2 to 10 carbon atoms.

An "alkenyl" group is defined as a monovalent hydrocarbon, which comprises at least one carbon-carbon double bond, which may be straight-chained or branched, or be or include one or more cyclic groups. An alkenyl group may optionally include one or more heteroatoms N, O or S in its carbon skeleton. Preferably an alkenyl group includes 0, 1, 2, 3 or 4 nitrogen atoms in its carbon skeleton. Preferably an alkenyl group includes 0, 1, 2, 3 or 4 oxygen atoms in its carbon skeleton. Preferably an alkenyl group includes 0, 1, 2, 3 or 4 sulphur atoms in its carbon skeleton. An alkenyl group may optionally include one or more carboxy groups —CO— in its carbon skeleton. Preferably an alkenyl group includes 0, 1, 2, 3 or 4 carboxy groups —CO— in its carbon skeleton, more preferably an alkenyl group does not include any carboxy groups —CO— in its carbon skeleton. Examples of alkenyl groups are vinyl, allyl, cyclohexenyl and octahydro-naphthalene groups. Preferably an alkenyl group is a $C_2$-$C_{30}$ alkenyl group, which is defined as an alkenyl group containing from 2 to 30 carbon atoms. An "alkenylene" group is similarly defined as a divalent alkenyl group. In one embodiment, an alkenyl group is or includes one or more cyclic groups and contains 17 to 25 carbon atoms. In another embodiment, an alkenyl group is straight-chained or branched and contains 2 to 10 carbon atoms.

An "alkynyl" group is defined as a monovalent hydrocarbon, which comprises at least one carbon-carbon triple bond, which may be straight-chained or branched, or be or include one or more cyclic groups. An alkynyl group may optionally include one or more heteroatoms N, O or S in its carbon skeleton. Preferably an alkynyl group includes 0, 1, 2, 3 or 4 nitrogen atoms in its carbon skeleton. Preferably an alkynyl group includes 0, 1, 2, 3 or 4 oxygen atoms in its carbon skeleton. Preferably an alkynyl group includes 0, 1, 2, 3 or 4 sulphur atoms in its carbon skeleton. An alkynyl group may optionally include one or more carboxy groups —CO— in its carbon skeleton. Preferably an alkynyl group includes 0, 1, 2, 3 or 4 carboxy groups —CO— in its carbon skeleton, more preferably an alkynyl group does not include any carboxy groups —CO— in its carbon skeleton. Examples of alkynyl groups are ethynyl, propargyl, but-1-ynyl and but-2-ynyl groups. Preferably an alkynyl group is a $C_2$-$C_{30}$ alkynyl group, which is defined as an alkynyl group containing from 2 to 30 carbon atoms. An "alkynylene" group is similarly defined as a divalent alkynyl group.

An "aryl" group is defined as a monovalent aromatic hydrocarbon. An aryl group may optionally include one or more heteroatoms N, O or S in its carbon skeleton. Preferably an aryl group includes 0, 1, 2, 3 or 4 nitrogen atoms in its carbon skeleton. Preferably an aryl group includes 0, 1, 2, 3 or 4 oxygen atoms in its carbon skeleton. Preferably an aryl group includes 0, 1, 2, 3 or 4 sulphur atoms in its carbon skeleton. An aryl group may optionally include one or more carboxy groups —CO— in its carbon skeleton. Preferably an aryl group includes 0, 1, 2, 3 or 4 carboxy groups —CO— in its carbon skeleton, more preferably an aryl group does not include any carboxy groups —CO— in its carbon skeleton. Examples of aryl groups are phenyl, naphthyl, anthracenyl, phenanthrenyl, furanyl, pyrrolyl, thiophenyl ($C_4H_3S$), oxazolyl, imidazolyl, thiazolyl, isoxazolyl, pyrazolyl, isothiazolyl, pyridinyl, quinolinyl, isoquinolinyl, indolyl, pyridazinyl, pyrimidinyl, pyrazinyl and favonyl ($C_{15}H_9O_2$) groups. Preferably an aryl group is a $C_{4-30}$ aryl group, which is defined as an aryl group containing from 4 to 30 carbon atoms. An "arylene" group is similarly defined as a divalent aryl group.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

For the purposes of this invention, an optionally substituted alkyl, alkenyl, alkynyl, aryl, arylalkyl, arylalkenyl, arylalkynyl, alkylaryl, alkenylaryl or alkynylaryl group may be substituted with one or more of —F, —Cl, —Br, —I, —$CF_3$, —$CCl_3$, —$CBr_3$, —$CI_3$, —OH, —SH, —$NH_2$, —CN, —$NO_2$, —COOH, —$R^1$—O—$R^2$, —$R^1$—S—$R^2$, —$R^1$—SO—$R^2$, —$R^1$—$SO_2$—$R^2$, —$R^1$—$SO_2$—$OR^2$, —$R^1O$—$SO_2$—$R^2$, —$R^1$—$SO_2$—$N(R^2)_2$, —$R^1$—$NR^2$—$SO_2$—$R^2$, —$R^1O$—$SO_2$—$OR^2$, —$R^1O$—$SO_2$—$N(R^2)_2$, —$R^1$—$NR^2$—$SO_2$—$OR^2$, —$R^1$—$NR^2$—$SO_2$—$N(R^2)_2$, —$R^1$—$N(R^2)_2$, —$R^1$—$N(R^2)_3^+$, —$R^1$—$P(R^2)_2$, —$R^1$—$Si(R^2)_3$, —$R^1$—CO—$R^2$, —$R^1$—CO—$OR^2$, —$R^1O$—CO—$R^2$, —$R^1$—CO—$N(R^2)_2$, —$R^1$—$NR^2$—CO—$R^2$, —$R^1O$—CO—$OR^2$, —$R^1O$—CO—$N(R^2)_2$, —$R^1$—$NR^2CO$—$OR^2$, —$R^1$—$NR^2CO$—$N(R^2)_2$, —$R^1$—CS—$R^2$, —$R^1$—CS—$OR^2$, —$R^1O$—CS—$R^2$, —$R^1$—CS—$N(R^2)_2$, —$R^1$—$NR^2$—CS—$R^2$, —$R^1O$—CS—$OR^2$, —$R^1O$—CS—$N(R^2)_2$, —$R^1$—$NR^2$—CS—$OR^2$, —$R^1$—$NR^2$—CS—$N(R^2)_2$ or —$R^2$. In this context, —$R^1$— is independently a chemical bond, a $C_{1-10}$ alkylene, $C_{1-10}$ alkenylene or $C_{1-10}$ alkynylene group. —$R^2$ is independently hydrogen, unsubstituted $C_{1-6}$ alkyl, unsubstituted $C_{1-6}$ alkenyl, unsubstituted $C_{1-6}$ alkynyl or unsubstituted $C_{6-10}$ aryl. Optional substituent(s) are not taken into account when calculating the total number of carbon atoms in the parent group substituted with the optional substituent(s). Preferably a substituted group comprises 1, 2 or 3 substituents, more preferably 1 or 2 substituents, and even more preferably 1 substituent.

Any optional substituent may be protected. Suitable protecting groups for protecting optional substituents are known in the art, for example from "Protective Groups in Organic Synthesis" by T. W. Greene and P. G. M. Wuts (Wiley-Interscience, $3^{rd}$ edition, 1999).

In one embodiment, R comprises a fused ring system, which may comprise one or more double bonds, and which may optionally be substituted. The fused ring system may comprise one or more five and/or six membered rings, which may comprise one or more double bonds, and which may optionally be substituted. The fused ring system may have a sterane structure as shown:

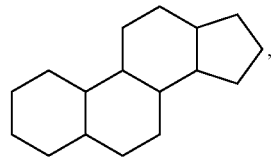 [SMILES: C1CCC2C(C1)CCC1C3CCCC3CCC21 ; ","]

which may comprise one or more double bonds, and which may optionally be substituted.

In one embodiment, R is a steroid alcohol moiety. In a preferred embodiment, R is a cholesteryl moiety, such that the compound of the present invention is cholesteryl betulonate having the structure (Ia-α) or (Ia-β) or a saturated derivative thereof having the structure (IIa-α) or (IIa-β):

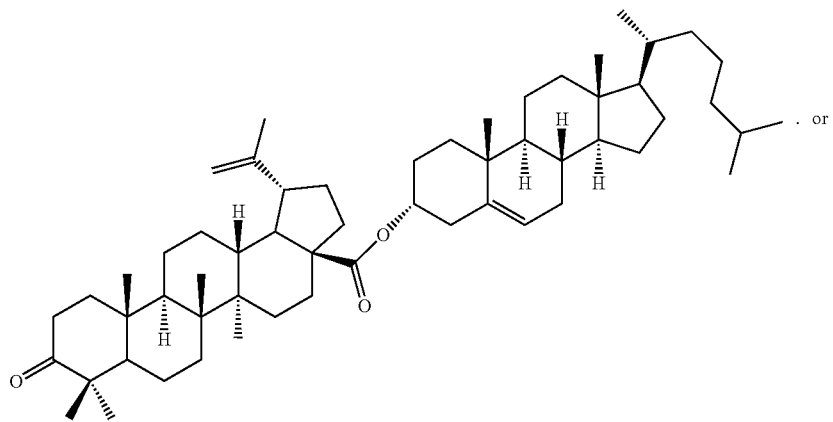

(Ia-α)

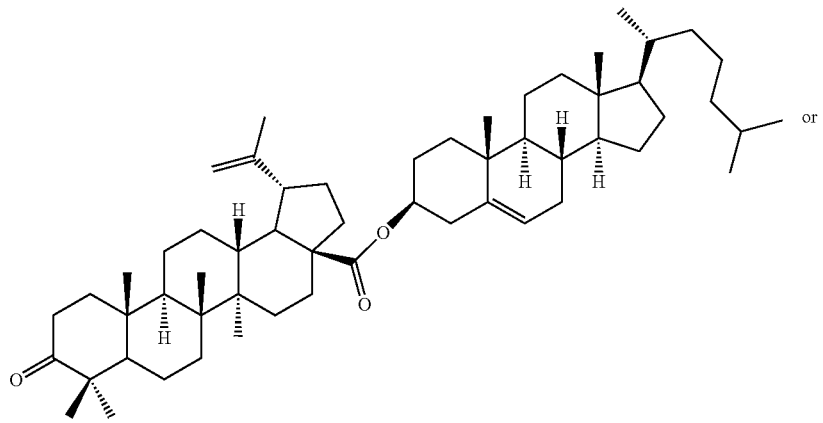

(Ia-β)

-continued

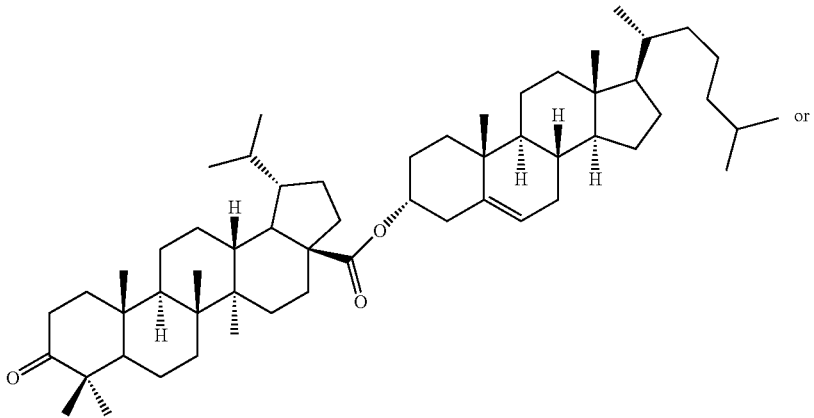

(IIa-α)

or

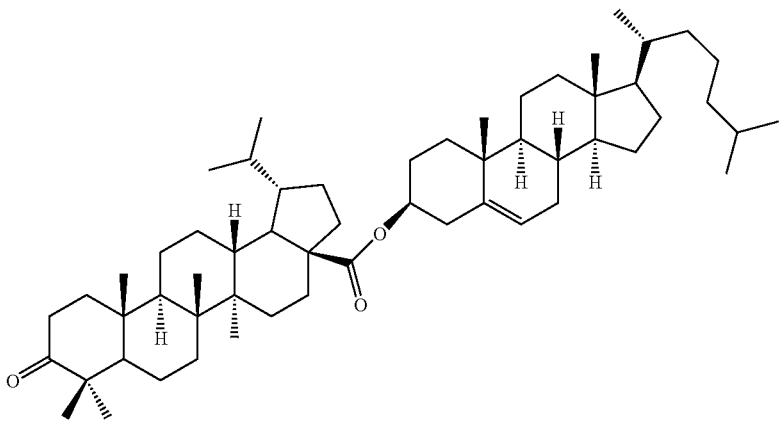

(IIa-β)

In one embodiment, R is a steroid hormone moiety or a steroid hormone metabolite moiety. In a preferred embodiment, R is an estrogen moiety such as an estradiol moiety, a progestogen moiety such as a progesterone moiety, an androgen moiety such as a testosterone moiety, or a dehydroepiandrosterone moiety.

In one embodiment, R is an alkyl, alkenyl, alkynyl, aryl, arylalkyl, arylalkenyl, arylalkynyl, alkylaryl, alkenylaryl or alkynylaryl group, which may optionally be substituted, and which may optionally include one or more heteroatoms N, O or S in its carbon skeleton.

In another embodiment, R is an alkyl, alkenyl, alkynyl, aryl, arylalkyl, arylalkenyl, arylalkynyl, alkylaryl, alkenylaryl or alkynylaryl group, containing from 2 to 20 carbon atoms, which may optionally be substituted. R may be an alkyl, aryl, arylalkyl, arylalkenyl, arylalkynyl, alkylaryl, alkenylaryl or alkynylaryl group, containing from 2 to 10 carbon atoms, which may optionally be substituted with —OH.

In yet another embodiment, R is an alkyl or alkenyl group, which may optionally be substituted. Preferably, R is an alkyl or alkenyl group, containing from 2 to 30 carbon atoms, which may optionally be substituted. Preferably, R is an alkyl group containing from 6 to 18 carbon atoms or R is an alkenyl group containing from 16 to 22 carbon atoms, each of which may optionally be substituted. If substituted, R may be substituted with a terminal —CO$_2$H or —CONH$_2$ group. Preferably, R is:

(a) —(CH$_2$)$_m$—CH$_3$, wherein m=13 to 18;
(b) —(CH$_2$)—(CH$_2$CH=CH)$_n$—(CH$_2$)$_p$—CH$_3$, wherein m=0 to 7, n=1 to 6, and p=0 to 7;
(c) —(CH$_2$)$_m$—CO$_2$H wherein m=1 to 8; or
(d) —(CH$_2$)$_m$—CONH$_2$, wherein m=1 to 8.

In particular for compounds of formula II, another preferred embodiment is where R is —(CH$_2$)$_m$—O—CO—CH$_3$, wherein m=1 to 6, preferably m=1.

The compound of the present invention may be used in the preparation of derivatives.

A derivative of a compound of the first aspect of the present invention may be bound to a poly(alkylene glycol), preferably via a linker. Preferably a derivatised ketone functionality of the compound is bound to the poly(alkylene glycol), preferably via a linker. Preferably, a derivatised ketone functionality of the compound is bound to the linker, which is in turn bound to the poly(alkylene glycol). Preferably the derivatised ketone functionality is an amine, an alcohol or a thiol, more preferably an amine. If present, the linker is preferably a diamine such as ornithine. Preferably, the poly(alkylene glycol) is
(a) poly(ethylene glycol) [HO—(CH$_2$CH$_2$O)$_n$—H],
(b) monomethoxy poly(ethylene glycol) [CH$_3$O—(CH$_2$CH$_2$O)$_n$—H],
(c) monoamino poly(ethylene glycol) [H$_2$N—(CH$_2$CH$_2$O)$_n$—H],
(d) monoamino monomethoxy poly(ethylene glycol) [H$_2$N—(CH$_2$CH$_2$O)$_n$—CH$_3$],
(e) mono (substituted amino) poly(ethylene glycol) [RHN—(CH$_2$CH$_2$O)$_n$—H],
(f) mono(substituted amino) monomethoxy poly(ethylene glycol) [RHN—(CH$_2$CH$_2$O)$_n$—CH$_3$],
(g) monocarboxy poly(ethylene glycol) [HO$_2$C—(CH$_2$)$_p$O—(CH$_2$CH$_2$O)$_n$—H], or (h) monocarboxy monomethoxy poly(ethylene glycol)
[HO$_2$C—(CH$_2$)$_p$O—(CH$_2$CH$_2$O)$_n$—CH$_3$],
wherein
n is an integer, preferably wherein n is from 1 to 1500,
R is an alkyl, alkenyl, alkynyl, aryl, arylalkyl, arylalkenyl, arylalkynyl, alkylaryl, alkenylaryl or alkynylaryl group, which may optionally be substituted and which may optionally include one or more heteroatoms N, O or S in its carbon skeleton, and
p is 1, 2, 3, 4, 5 or 6.

For the purposes of the present invention, a poly(alkylene glycol) (PAG) is a compound of the formula H—(O-alkyl)$_n$-OH which is herein abbreviated to PAG-OH. The repeating alkyl group of a poly(alkylene glycol) may be straight-chained or branched, preferably the alkyl group is straight-chained. The poly(alkylene glycol) may be functionalised at one end, for example with a terminal —R, —NH$_2$, —NHR, —NR$_2$, —SH, —SR or —CO$_2$H group, wherein R is an alkyl, alkenyl, alkynyl, aryl, arylalkyl, arylalkenyl, arylalkynyl, alkylaryl, alkenylaryl or alkynylaryl group, which may optionally be substituted and which may optionally include one or more heteroatoms N, O or S in its carbon skeleton, preferably wherein R is an unsubstituted alkyl group, more preferably wherein R is an unsubstituted C$_{1-6}$ alkyl group. The poly(alkylene glycol) may be functionalised at both ends, provided at least one end is functionalised with a terminal —NH$_2$, —NHR or —SH group, wherein R is defined as immediately above. Preferably, a poly(alkylene glycol) is of the formula HO—[(CH$_2$)$_m$O]$_n$—H, wherein m is from 1 to 4, and n is from 1 to 1500.

Attaching PAGs to therapeutically active compounds confers many new and interesting properties to the compounds with regard to their use as drugs. As a general rule, PAG-modified compounds exhibit increased stability, an increased metabolic half-life, decreased immunogenicity, and decreased toxicity.

PAGs are linear, hydrophilic, uncharged and flexible polymers, which are commercially available in a variety of molecular weights. PAGs are not toxic and generally recognised as safe. In particular, monomethoxy poly(ethylene glycol) (mPEG) is approved by the FDA as a vehicle or base for a number of pharmaceutical preparations and has a low order of toxicity in oral, parenteral and epidermal applications. When administered intravenously to humans, mPEGs with a molecular weight of 1 to 6 kDa are readily excreted, mainly via the kidney.

Preferably, to effect covalent attachment of PAGs to betulonic acid ester derivatives, a hydroxyl end-group of the PAG polymer is converted into a reactive functional group. Methods of activating PAGs are known in the art. European patent EP 0 632 082, which is incorporated herein by reference in its entirety, discusses a wide variety of methods of activating PAGs. Examples of activated PAGs are shown in FIG. 1. Methods of obtaining these activated PAGs are known to those skilled in the art. The activated PAGs may be isolated before coupling to the betulonic acid ester derivatives. Alternatively, the activated PAGs may be prepared in situ and coupled to the betulonic acid ester derivatives without isolating.

A preferred method of activating PAGs for the purposes of the present invention is the use of phosgene (Cl$_2$CO) or 1,1'-carbonyldiimidazole (CDI) to provide a PAG chloroformate or a PAG 1-carbonylimidazole, followed by the use of 4-dimethylaminopyridine (DMAP) to provide a PAG carbamate (see Scheme 1, DMAP carbamate methodology).

Scheme 1

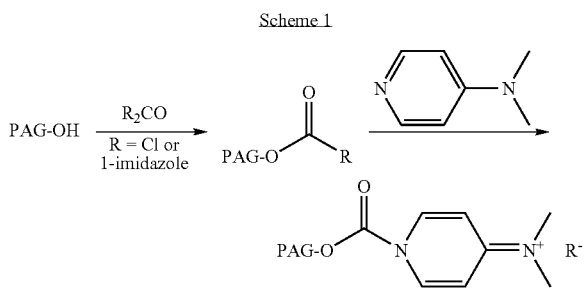

An alternative preferred method of activating PAGs for the purposes of the present invention is the use of Mukaiyama's reagent (2-chloro-1-methylpyridinium iodide, CMPI) on a PAG carboxylic acid to provide a PAG ester (see Scheme 2, CMPI ester methodology).

Scheme 2

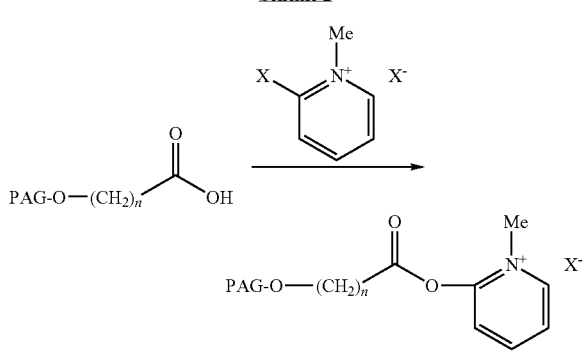

wherein n = 1, 2, 3, 4, 5 or 6 and each X independently = Cl or I

Since the betulonic acid ester derivatives of the present invention lack a suitable functional group for coupling to activated PAGs, the betulonic acid ester derivatives may be derivatised before coupling. In one embodiment, the C-3 ketone functionality of a betulonic acid ester derivative is reduced to provide the corresponding betulinic acid ester derivative, which is coupled to an activated PAG via the C-3 hydroxyl group (see Scheme 3).

Scheme 3

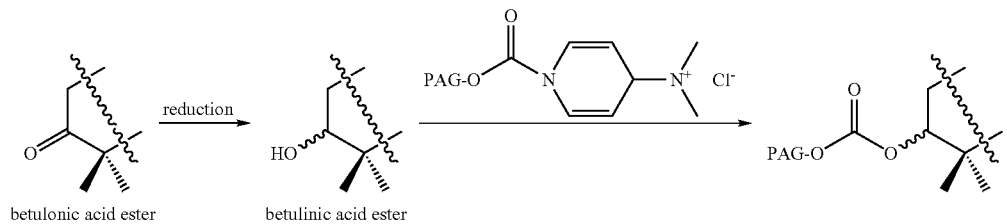

betulonic acid ester     betulinic acid ester

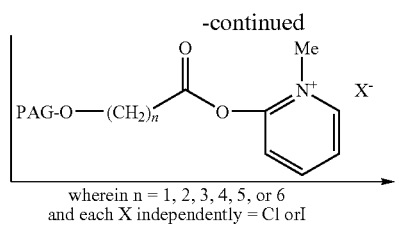

wherein n = 1, 2, 3, 4, 5, or 6
and each X independently = Cl or I

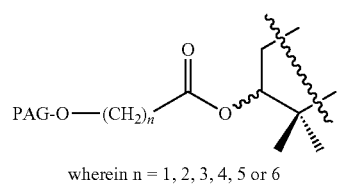

wherein n = 1, 2, 3, 4, 5 or 6

In another embodiment, the C-3 hydroxyl group of the betulinic acid ester derivative is converted into an amino group or a sulfhydryl group, which is coupled to an activated PAG via the C-3 amino or sulfhydryl group (see Scheme 4).

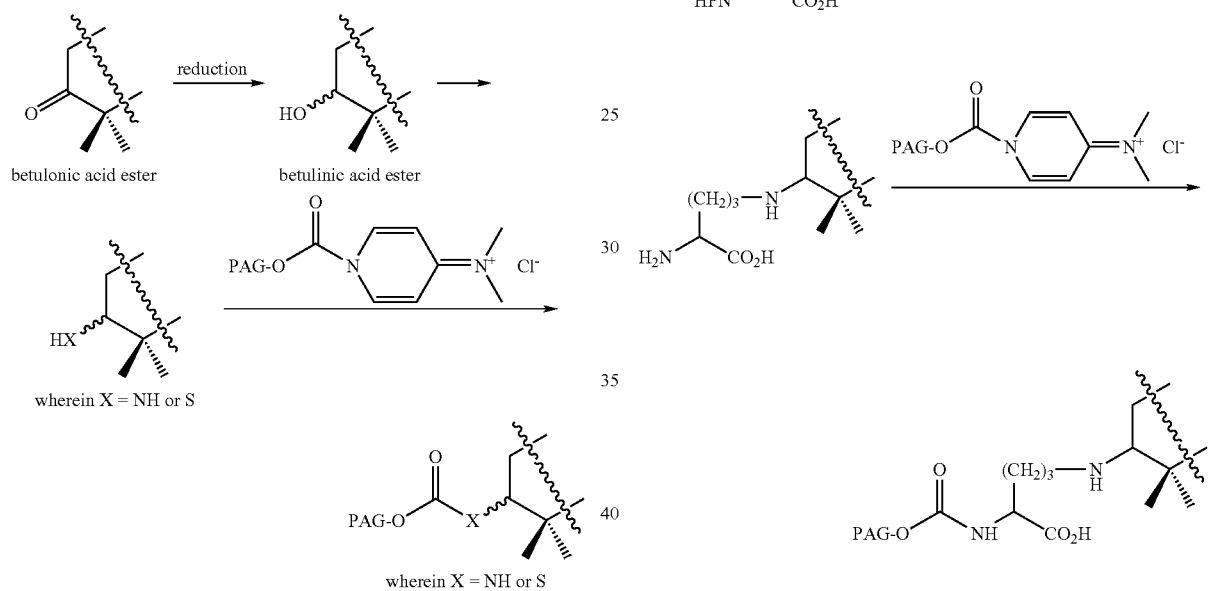

In another embodiment, a linker is coupled to the C-3 ketone functionality of a betulonic acid ester derivative, and the linker is then coupled to an activated PAG (see Scheme 5). A preferred linker is a diamine, such as ornithine, which may be suitably protected, for example, with a Boc or an Fmoc group. Suitable protecting groups are known in the art, for example from "Protective Groups in Organic Synthesis" by T. W. Greene and P. G. M. Wuts (Wiley-Interscience, 3$^{rd}$ edition, 1999).

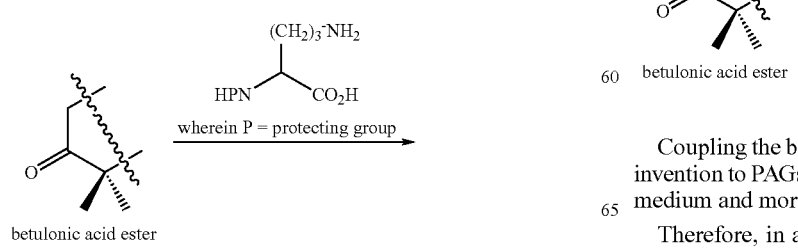

Alternatively, a PAG may be covalently attached to a betulonic acid ester derivative without activating the PAG and without prior derivatisation of the betulonic acid ester derivative. For example, PAG-OH, PAG-NH$_2$, PAG-NHR or PAG-SH can be condensed with the C-3 ketone functionality of a betulonic acid ester derivative under reductive conditions (see Scheme 6).

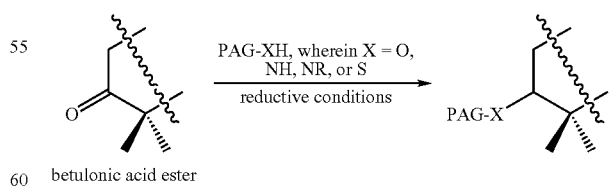

Coupling the betulonic acid ester derivatives of the present invention to PAGs renders the esters more soluble in aqueous medium and more stable in vivo.

Therefore, in a second aspect, the present invention provides a compound having the structure (III):

(III)

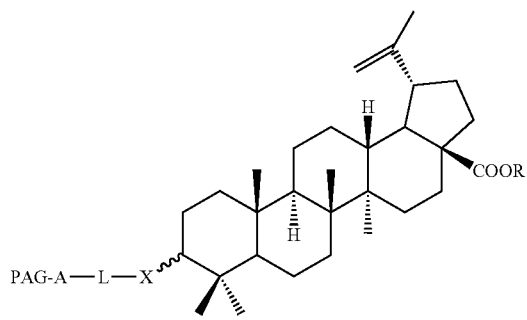

wherein
R is hydrogen or an alkyl, alkenyl, alkynyl, aryl, arylalkyl, arylalkenyl, arylalkynyl, alkylaryl, alkenylaryl or alkynylaryl group, which may optionally be substituted, which may optionally include one or more heteroatoms N, O or S in its carbon skeleton, and which may optionally include one or more carboxy groups —CO— in its carbon skeleton, X is NH, O or S, L is a bond or a linker, A is a bond or an activation moiety, and PAG is a poly(alkylene glycol), provided that the compound is not

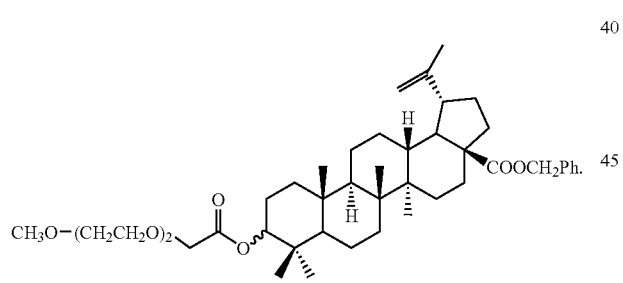

The second aspect of the present invention also provides a compound having the structure (IV):

(IV)

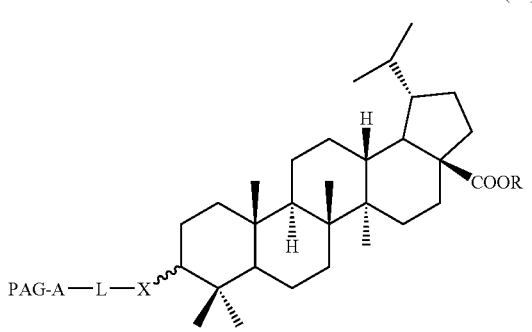

wherein
R is hydrogen or an alkyl, alkenyl, alkynyl, aryl, arylalkyl, arylalkenyl, arylalkynyl, alkylaryl, alkenylaryl or alkynylaryl group, which may optionally be substituted, which may optionally include one or more heteroatoms N, O or S in its carbon skeleton, and which may optionally include one or more carboxy groups —CO— in its carbon skeleton, X is NH, O or S, L is a bond or a linker, A is a bond or an activation moiety, and PAG is a poly(alkylene glycol).

In one embodiment, R comprises a fused ring system, which may comprise one or more double bonds, and which may optionally be substituted. The fused ring system may comprise one or more five and/or six membered rings, which may comprise one or more double bonds, and which may optionally be substituted. The fused ring system may have a sterane structure as shown:

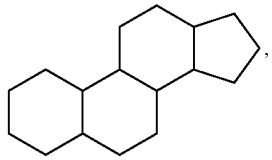 [SMILES: C1CCC2C(C1)CCC1C3CCCC3CCC21 ; ","]

which may comprise one or more double bonds, and which may optionally be substituted.

In one embodiment, R comprises a steroid alcohol moiety. In a preferred embodiment, the steroid alcohol moiety is a cholesteryl moiety, in which case the compound has the structure (IIIa-α), (IIIa-β), (IVa-α) or (IVa-β):

(IIIa-α)

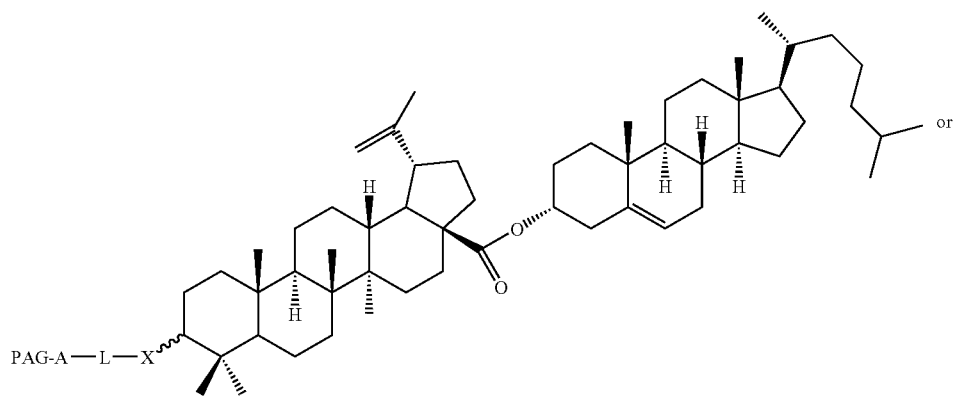

or

-continued
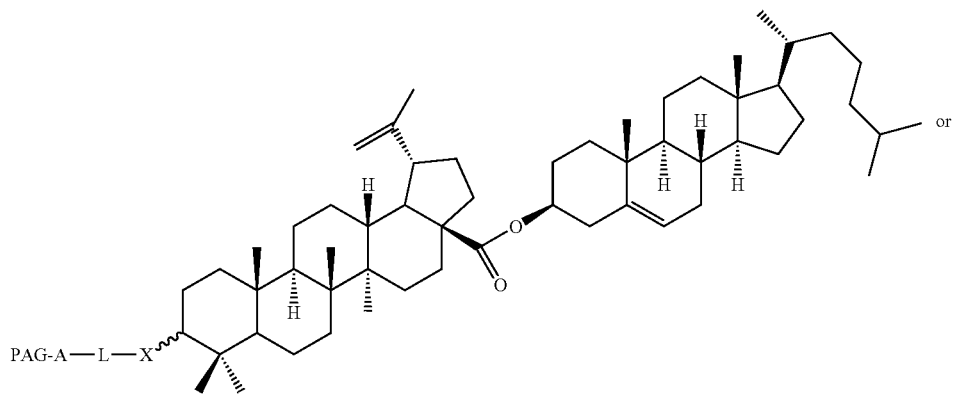
(IIIa-β)
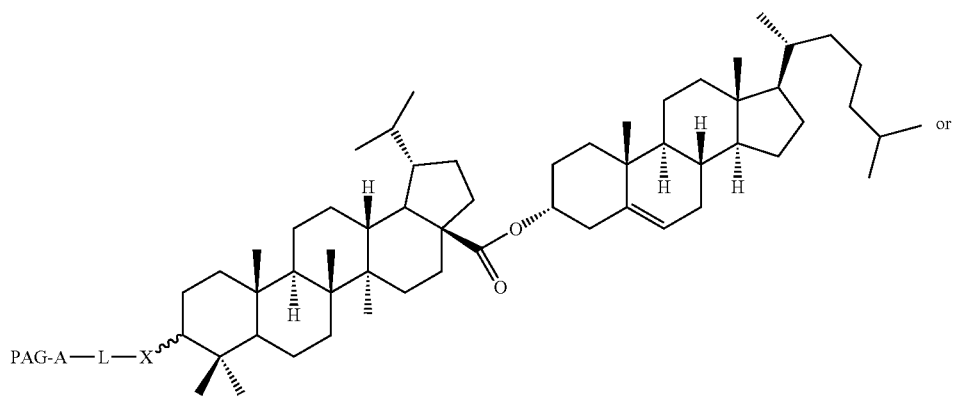
(IVa-α)
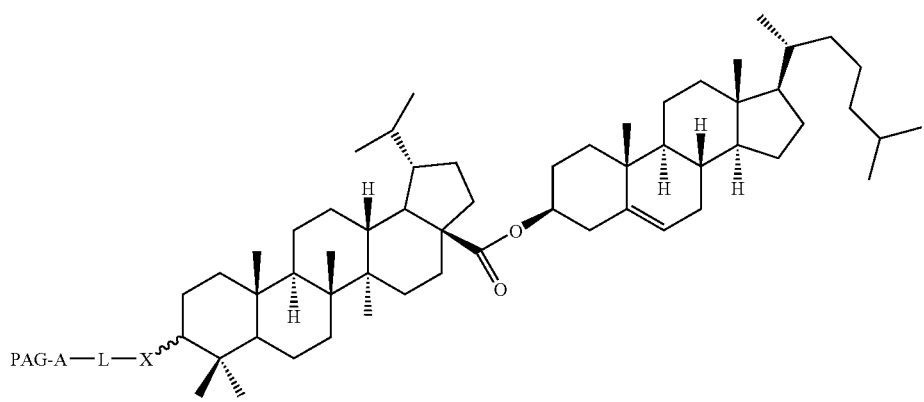
(IVa-β)
In a preferred embodiment, the compound has the structure (IIIb-α), (IIIb-β), (IVb-α), (IVb-β), (IIIc-α), (IIIc-β), (IVc-α) or (IVc-β):

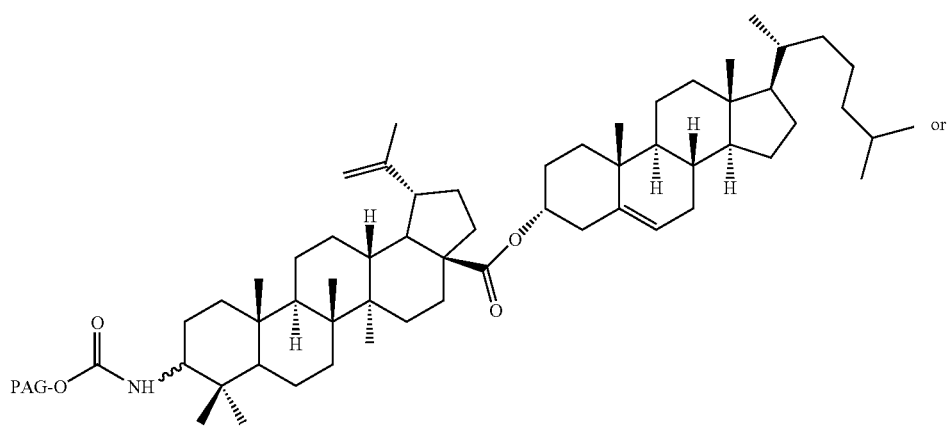
(IIIb-α)
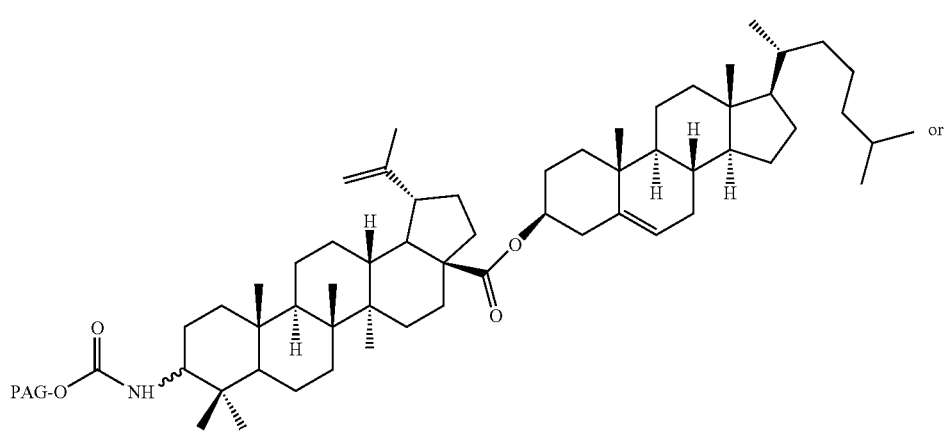
(IIIb-β)
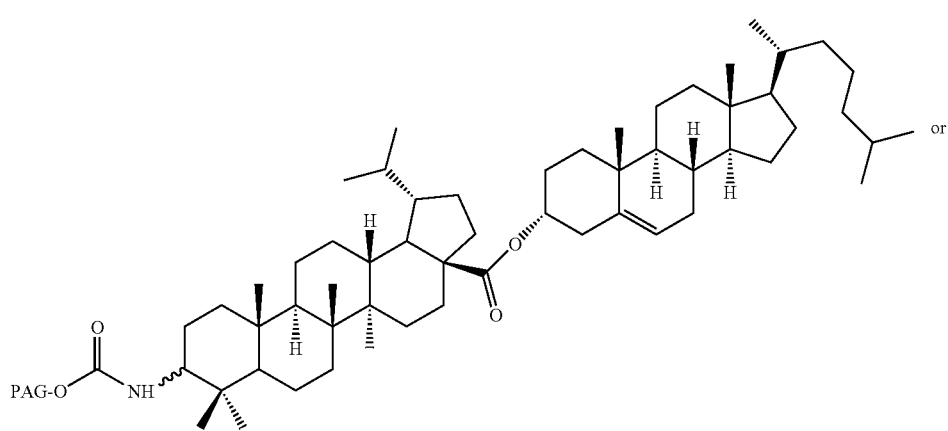
(IVb-α)

-continued
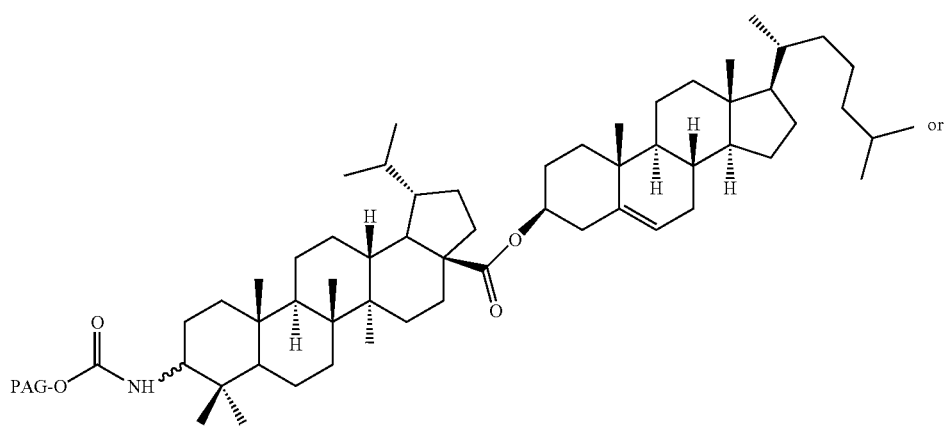
(IVb-β)
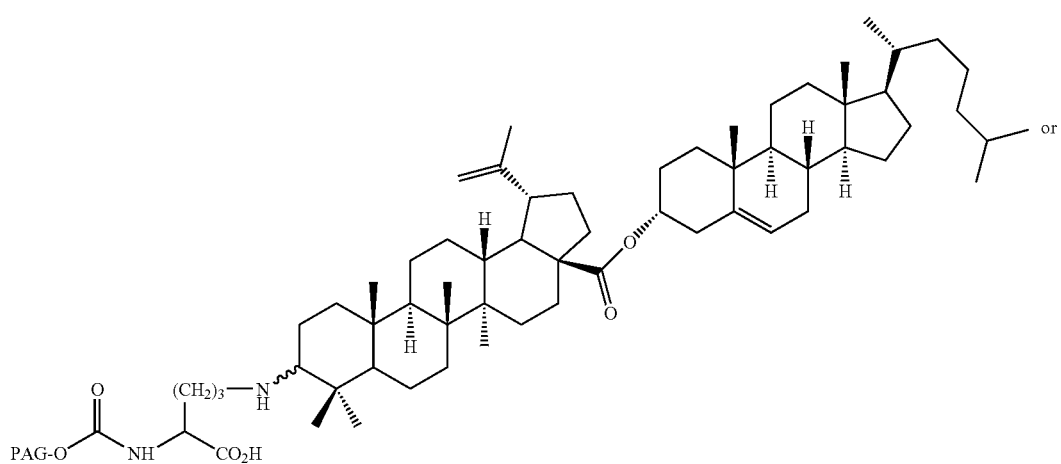
(IIIc-α)
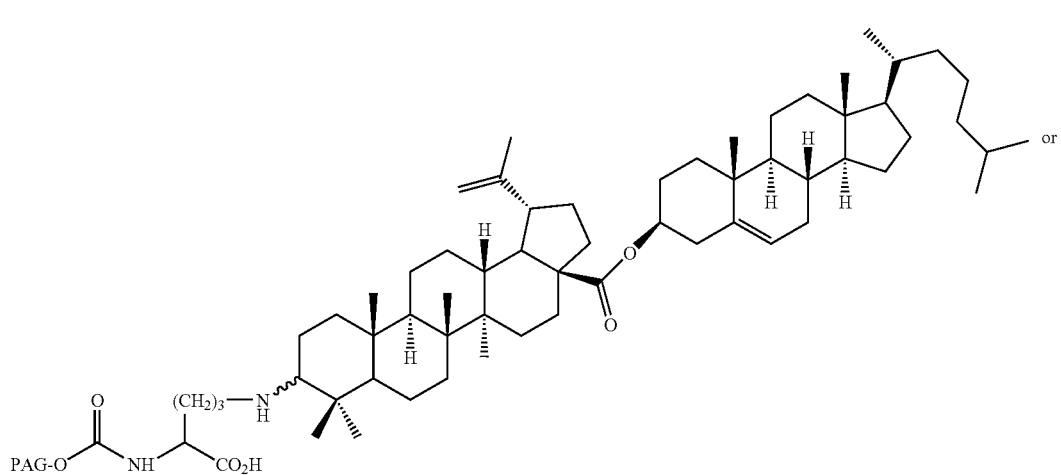
(IIIc-β)

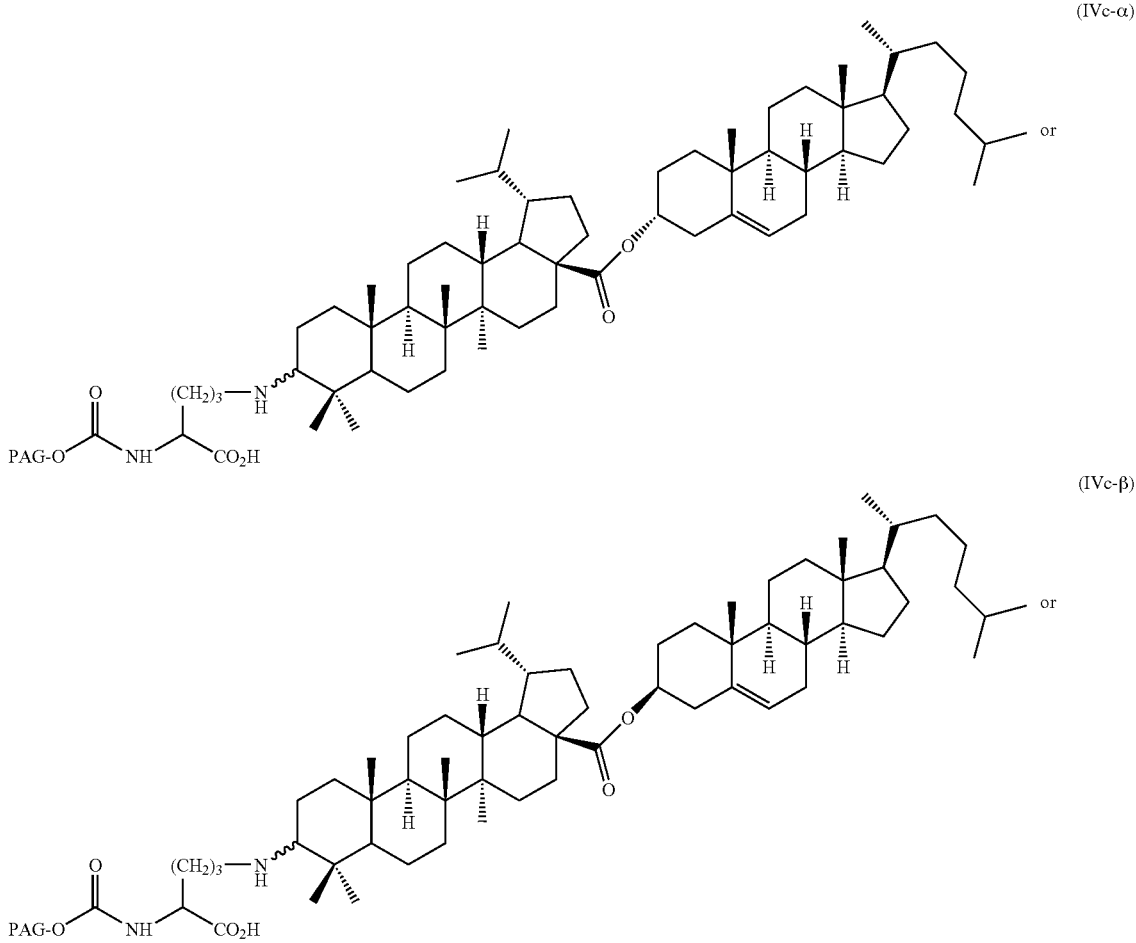

In one embodiment, R is a steroid hormone moiety or a steroid hormone metabolite moiety. In a preferred embodiment, the steroid hormone moiety is an estrogen moiety such as an estradiol moiety, a progestogen moiety such as a progesterone moiety, an androgen moiety such as a testosterone moiety, or a dehydroepiandrosterone moiety.

In one embodiment, R is an alkyl, alkenyl, alkynyl, aryl, arylalkyl, arylalkenyl, arylalkynyl, alkylaryl, alkenylaryl or alkynylaryl group, which may optionally be substituted, which may optionally include one or more heteroatoms N, O or S in its carbon skeleton, and which may optionally include one or more carboxy groups —CO— in its carbon skeleton. In another embodiment, R is an alkyl, alkenyl, alkynyl, aryl, arylalkyl, arylalkenyl, arylalkynyl, alkylaryl, alkenylaryl or alkynylaryl group, which may optionally be substituted, and which may optionally include one or more heteroatoms N, O or S in its carbon skeleton.

In another embodiment, R is hydrogen or an alkyl, alkenyl, alkynyl, aryl, arylalkyl, arylalkenyl, arylalkynyl, alkylaryl, alkenylaryl or alkynylaryl group, containing from 2 to 20 carbon atoms, which may optionally be substituted. In another embodiment, R is an alkyl, alkenyl, alkynyl, aryl, arylalkyl, arylalkenyl, arylalkynyl, alkylaryl, alkenylaryl or alkynylaryl group, containing from 2 to 20 carbon atoms, which may optionally be substituted. R may be an alkyl, aryl, arylalkyl, arylalkenyl, arylalkynyl, alkylaryl, alkenylaryl or alkynylaryl group, containing from 2 to 10 carbon atoms, which may optionally be substituted with —OH.

In another embodiment, R is an alkyl or alkenyl group, which may optionally be substituted. Preferably, R is an alkyl or alkenyl group, containing from 2 to 30 carbon atoms, which may optionally be substituted. Preferably, R is an alkyl group containing from 6 to 18 carbon atoms or R is an alkenyl group containing from 16 to 22 carbon atoms, each of which may optionally be substituted. If substituted, R may be substituted with a terminal —CO$_2$H or —CONH$_2$ group. Preferably, R is:

(a) —(CH$_2$)$_m$—CH$_3$, wherein m=13 to 18;
(b) —(CH$_2$)$_m$—(CH$_2$CH=CH)$_n$—(CH$_2$)$_p$—CH$_3$, wherein m=0 to 7, n=1 to 6, and p=0 to 7;
(c) —(CH$_2$)$_m$—CO$_2$H, wherein m=1 to 8;
(d) —(CH$_2$)$_m$—CONH$_2$, wherein m=1 to 8; or
(e) —(CH$_2$)$_m$—O—CO—CH$_3$, wherein m=1 to 6, preferably m=1.

In yet another embodiment, R is —CH$_3$, —CH$_2$—O—CO—C(CH$_3$)$_3$, or —CH$_2$—O—CO—CH$_3$.

In one embodiment, X is NH. In another embodiment, X is O. In yet another embodiment, X is S. Preferably X is NH.

In one embodiment, L is a bond. In another embodiment, L a linker. The linker may be derived from a diamine (such as ornithine) or an amino acid (such as lysine, glycine or ornithine). The linker may be, or form part of a peptide, an ester or a carbonate.

As outlined above, to effect covalent attachment of PAGs to therapeutically active compounds, a hydroxyl end-group of the PAG polymer may be converted into a reactive functional group. The activation moiety A is the remainder, if any, of such a reactive functional group. If a preferred activated PAG is used, the PAG carbamate shown in Scheme 1 above, then the activation moiety A is —O—CO—.

In one embodiment, the poly(alkylene glycol) is poly(ethylene glycol), such as monomethoxy poly(ethylene glycol).

In preferred PAG-A-L-X— moieties, the -A-L- moiety is an alkyl group, which may optionally be substituted, which may optionally include one or more heteroatoms N, O or S in its carbon skeleton, and which may optionally include one or more carboxy groups —CO— in its carbon skeleton. Preferably, the -A-L- moiety is an unsubstituted alkyl group, which optionally includes one or more heteroatoms N, O or S in its carbon skeleton, and which optionally includes one or more carboxy groups —CO— in its carbon skeleton. Preferably, the -A-L- moiety is an unsubstituted alkyl group, which optionally includes one or more heteroatoms N or O in its carbon skeleton, and which optionally includes one or more carboxy groups —CO— in its carbon skeleton. Preferably, the -A-L- moiety is an unsubstituted alkyl group, which includes 0, 1, 2, 3 or 4 nitrogen atoms, and 0, 1, 2, 3 or 4 oxygen atoms, and 0, 1, 2, 3 or 4 carboxy groups —CO— in its carbon skeleton.

Preferred PAG-A-L-X— moieties are:

(a)

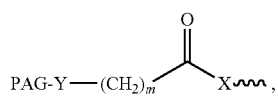

wherein Y=bond, O or NH, and m=0 to 30 (preferably m=0 to 10);

(b)

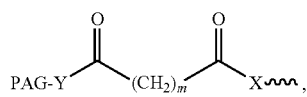

wherein Y=bond, O or NH, and m=0 to 30 (preferably m=0 to 10);

(c)

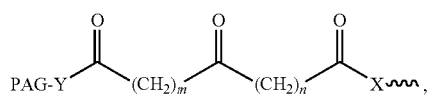

wherein Y=bond, O or NH, m=0 to 30, and n=0 to 30 (preferably m=0 to 10, and preferably n=0 to 10);

(d)

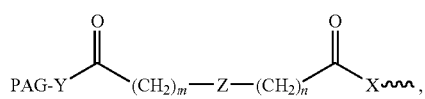

wherein Y=bond, O or NH, Z=O or NH, m=0 to 30, and n=0 to 30 (preferably m=0 to 10, and preferably n=0 to 10);

(e)

wherein Y=bond, O or NH, and m=0 to 30 (preferably m=0 to 10);

(f)

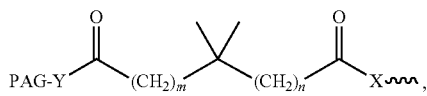

wherein Y=bond, O or NH, m=0 to 30, and n=0 to 30 (preferably m=0 to 10, and preferably n=0 to 10);

(g)

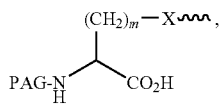

wherein m=1 to 6 (preferably m=3 or 4);

(h)

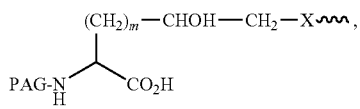

wherein m=1 to 4 (preferably m=1 or 2);

(i)

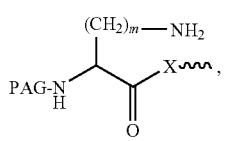

wherein m=1 to 6 preferably n=3 or 4);

(j)

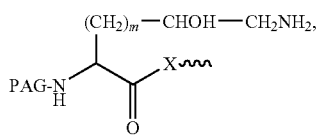

wherein m=1 to 4 (preferably m=1 or 2);

(k)

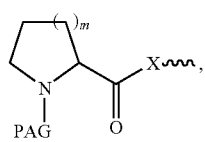

wherein m=1 or 2; or (l)

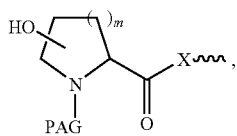

wherein n=1 or 2; and
wherein PAG and X are as defined above.

Further preferred PAG-A-L-X— moieties are:

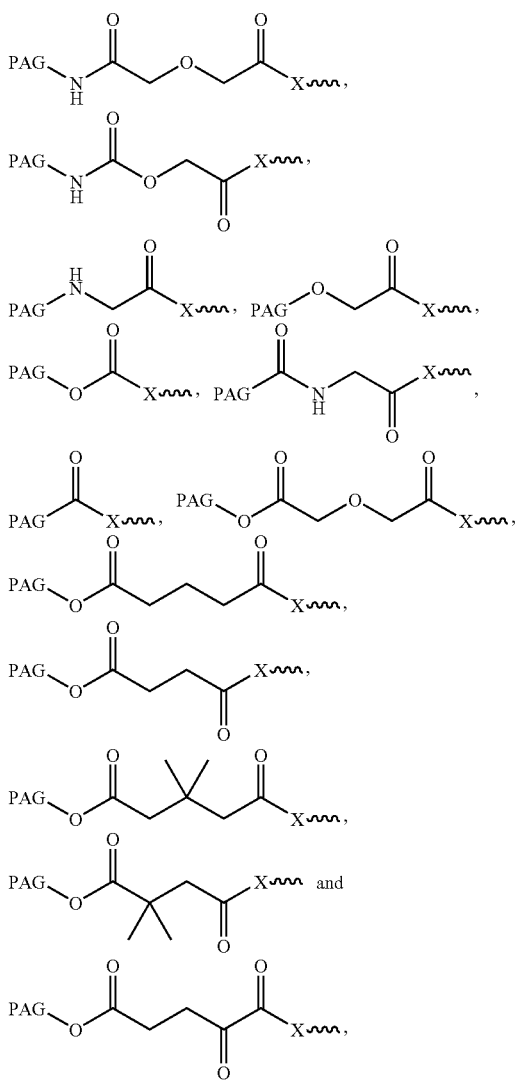

wherein PAG and X are as defined above.

The compounds of the first and second aspect of the present invention may be used in medicine, preferably as an anticancer agent or an antiviral agent. The compounds of the first and second aspect of the present invention are generally non-toxic to non-cancerous cells, whilst being cytotoxic to a wide range of cancer cells. The anticancer agent of the present invention can be used in, for example, the treatment of brain cancer, colon cancer, liver cancer, ovarian cancer, breast cancer, skin cancer, lung cancer, prostate cancer, neuroblastoma, fibrosarcoma or leukaemia. Especially when R is a steroid hormone moiety or a steroid hormone metabolite moiety, the anticancer agent of the present invention can be used in the treatment of hormonally dependent cancers, such as ovarian cancer, breast cancer or prostate cancer. The antiviral agent of the present invention can be used in, for example, the treatment of HIV-1, HIV-2, HSV-1, HSV-2 or influenza infection.

Many compounds of the first and second aspect of the present invention, in particular C 3 PAG-modified compounds, C-28 fatty acid esters and C-28 acetoalkyl esters of the present invention, are water soluble. This is advantageous, because it facilitates the administration of the compounds to patients. Without wishing to be bound by theory, it is currently believed that, following administration to a patient, C-28 fatty acid esters of the present invention are hydrolysed in vivo by endogenous lipase activity.

Therefore, in a third aspect, the present invention provides a pharmaceutical composition comprising a compound of the present invention and a pharmaceutically acceptable carrier or diluent.

The pharmaceutical composition of the present invention may comprise PEG-albumin or a liposome. PEG-albumin can be prepared from bovine serum albumin or human serum albumin. PEG-albumin can be prepared by the pegylation methods described above in relation to the compounds of the present invention. Again, a preferred pegylation method activates the PAG using phosgene ($Cl_2CO$) or 1,1'-carbonyldiimidazole (CDI) followed by 4-dimethylaminopyridine (DMAP) (see Scheme 1 above). An alternative preferred pegylation method activates a PAG carboxylic acid using Mukaiyama's reagent (2-chloro-1-methylpyridinium iodide, CMPI) (see Scheme 2 above).

In a fourth aspect, the present invention provides a use of a compound of the present invention in the manufacture of a medicament, preferably for the treatment of cancer or for the treatment of a viral infection. The medicament of the present invention can be used in, for example, the treatment of HIV-1, HIV-2, HSV-1, HSV-2 or influenza infection. The medicament of the present invention can also be used in, for example, the treatment of brain cancer, colon cancer, liver cancer, ovarian cancer, breast cancer, skin cancer, lung cancer, prostate cancer, neuroblastoma, fibrosarcoma or leukaemia. Especially when R is a steroid hormone moiety or a steroid hormone metabolite moiety, the medicament of the present invention can be used in the treatment of hormonally dependent cancers, such as ovarian cancer, breast cancer or prostate cancer.

The pharmaceutical composition or medicament employed in the present invention can be administered by oral, parental (including intravenous, subcutaneous, intramuscular, intradermal, intratracheal, intraperitoneal, intraarticular and intraabdominal), transdermal, airway (aerosol), rectal, vaginal or topical (including buccal, mucosal and sublingual) administration.

For oral administration, the compounds of the invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. If desired, the tablets may be coated.

Capsules for oral use include hard gelatine capsules in which the active ingredient is mixed with a solid diluent, and soft gelatine capsules wherein the active ingredient is mixed with water or an oil.

Formulations for rectal administration may be presented as a suppository with a suitable base.

Formulations suitable for vaginal administration may be presented as pessaries, tampons, creams, gels, pastes, foams or spray formulations containing in addition to the active ingredient such carriers as are known in the art to be appropriate.

For parenteral use, the compounds of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents, wetting agents and preservatives. The compounds of the invention may also be presented as liposome formulations.

For topical and transdermal administration, the compounds of the invention will generally be provided in the form of ointments, cataplasms (poultices), pastes, powders, dressings, creams, plasters or patches.

Suitable suspensions and solutions can be used in inhalers for airway (aerosol) administration.

In general, a suitable dose will be in the range of 0.01 to 10 mg per kilogram body weight of the recipient per day, preferably in the range of 0.1 to 5 mg per kilogram body weight per day. The desired dose is preferably presented once a day, but may be dosed as two, three, four, five, six or more sub-doses administered at appropriate intervals throughout the day. These sub-doses may be administered in unit dosage forms, for example, containing 1 to 1500 mg, preferably 10 to 1000 mg, and most preferably 20 to 500 mg of active ingredient per unit dosage form.

In a fifth aspect, the present invention provides a method of treating cancer, comprising administering a therapeutically effective amount of a compound of the present invention to a subject in need of such treatment. The cancer may be brain cancer, colon cancer, liver cancer, ovarian cancer, breast cancer, skin cancer, lung cancer, prostate cancer, neuroblastoma, fibrosarcoma or leukaemia. Especially when R is a steroid hormone moiety or a steroid hormone metabolite moiety, the compound of the present invention can be used in the treatment of hormonally dependent cancers, such as ovarian cancer, breast cancer or prostate cancer. Preferably the subject is a mammal, more preferably a human.

The present invention also provides a method of treating a viral infection, comprising administering a therapeutically effective amount of a compound of the present invention to a subject in need of such treatment. The viral infection may be HIV-1, HIV-2, HSV-1, HSV-2 or influenza infection. Preferably the subject is a mammal, more preferably a human.

In a sixth aspect, the present invention provides a process for the preparation of a compound of the first or second aspect of the present invention, comprising the step of esterifying the C-28 carboxylic acid of betulonic acid or of a PAG-substituted betulinic acid derivative. The esterification may be carried out using triphenylphosphine and diethyl azodicarboxylate (DEAD) in a Mitsunobu reaction, for example to prepare a cholesteryl or farnesyl ester. Alternatively, the esterification may be carried out using a base such as DBU in a nucleophilic substitution reaction, for example to prepare an acetoxymethyl ester.

The betulonic acid may be obtained by oxidising betulin. The oxidation may be carried out using chromium trioxide and sulphuric acid as patented in 1998 by Pezzuto et al. (U.S. Pat. No. 5,804,575) and modified in 2002 by N. I. Petrenko et al. (*Chemistry of Natural Compounds,* 38, 331-339). The process of the present invention may further comprise the steps of reducing the C-3 ketone of betulonic acid or a derivative thereof to an alcohol, amine or thiol functionality, and PAG-modifying the C-3 alcohol, amine or thiol functionality. The esterification of the C-28 carboxylic acid may be carried out before or after any of steps of oxidising betulin to betulonic acid, reducing the C-3 ketone of betulonic acid or a derivative thereof to an alcohol, amine or thiol functionality, and PAG-modifying the C-3 alcohol, amine or thiol functionality.

An advantage of the process of the present invention is that it and any of its steps can be carried out on an industrial scale and in high yield. For the purposes of the present invention, the term "industrial scale" means that the product of a reaction is obtained in batches of 1 g, 20 g, 50 g, 100 g, 500 g, 1 kg, 5 kg, 10 kg, 25 kg or more. For the purposes of the present invention, the term "high yield" means that the product of a reaction is obtained in a yield of 50%, 60%, 70%, 80%, 90% or more relative to the starting material.

In a seventh aspect, the present invention provides a use of a compound of the present invention for the preparation of a derivative. The ketone functionality of the compound of the present invention may be reduced to an alcohol functionality. The reduction may be carried out using $NaBH_4$ or $M^+BHR_3^-$, wherein $M^+$ is $Na^+$, $Li^+$ or $K^+$, and R is independently a $C_{1-4}$ alkyl group, for example, s-butyl.

In an eighth aspect, the present invention provides a process for the preparation of a compound of the second aspect of the present invention, comprising the step of reducing the ketone functionality of a compound of the first aspect of the present invention to an alcohol functionality. The reduction may be carried out using $NaBH_4$ or $M^+BHR_3^-$, wherein $M^+$ is $Na^+$, $Li^+$ or $K^+$, and R is independently a $C_{1-4}$ alkyl group, for example, s-butyl.

BRIEF DESCRIPTION OF THE DRAWINGS

The present invention will now be described by way of example with reference to the accompanying drawings in which.

DETAILED DESCRIPTION OF THE INVENTION

Figure 1:
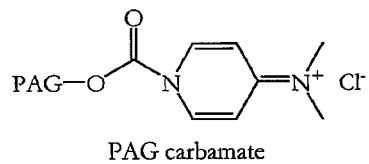
FIG. 1 shows examples of activated PAGs.
Figure 1:
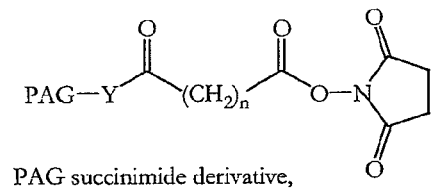
Figure 1:
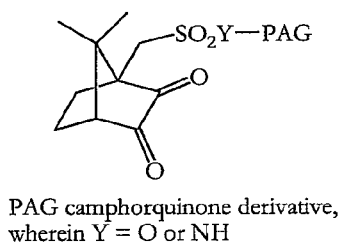
Figure 1:
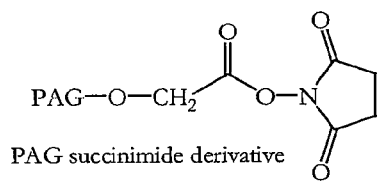
Figure 1:
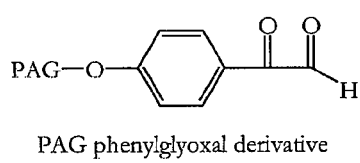
Figure 1:
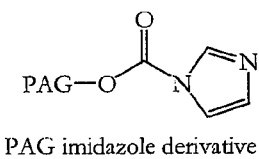
Figure 1:
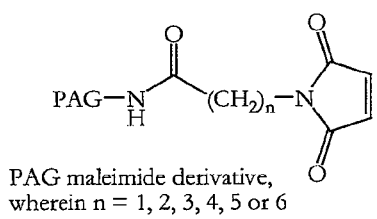
Figure 1:
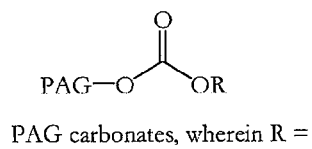
Figure 1:
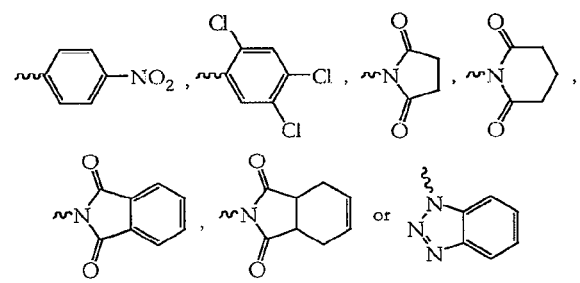
Figure 1:
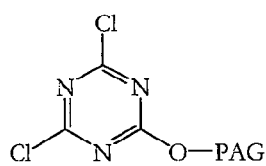
Figure 1:
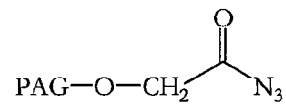
Figure 1:
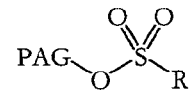
Figure 1:
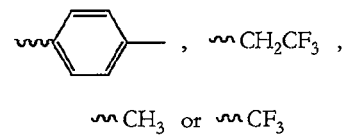
Figure 1:
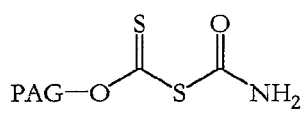
Figure 1:
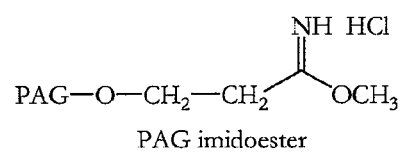
Figure 1:
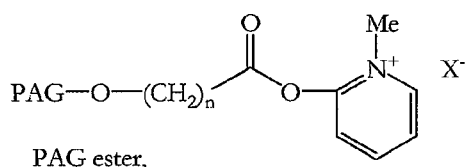
Figure 1:
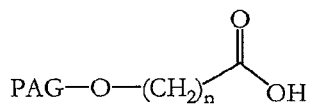
Figure 1:
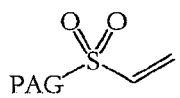
Figure 1:
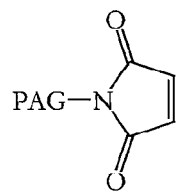
Figure 1:
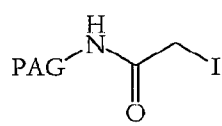
Figure 1:
Figure 1:
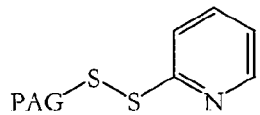

The present invention will now be described with reference to the following examples. It will be appreciated that what follows is by way of example only and that modifications to detail may be made whilst still falling within the scope of the invention.

Example 1 synthesis of 3-oxo-lup-20(29)-en-28-oic acid (betulonic acid) 1

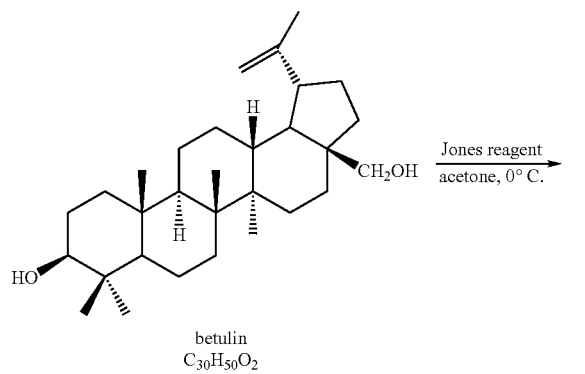

betulin
$C_{30}H_{50}O_2$

Jones reagent
acetone, 0° C.

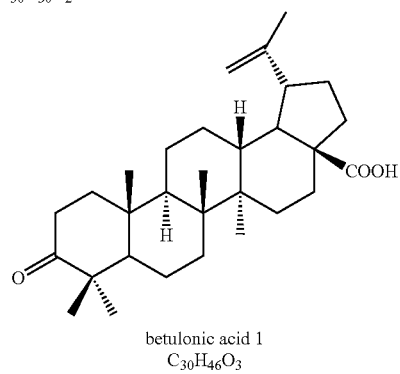

betulonic acid 1
$C_{30}H_{46}O_3$

In a 250 ml round-bottomed flask, equipped with a magnetic stirring bar, a 100 ml addition funnel and a septum fitted with a nitrogen inlet, was placed 1 g (2.258 mmol) betulin in 150 ml acetone. The flask was cooled with an ice-acetone bath and the suspension of betulin was treated dropwise with Jones' reagent [L. F. Fieser, M. Fieser, *Reagents for Organic Synthesis*, vol. 1, 1967, p. 143] over 15 minutes. The reaction mixture was stirred at 0° C. for 2 hours and then treated with methanol (25 ml) until it turned dark green. The reaction mixture was poured onto a mixture of ice and water (50 ml), then acetone and methanol were removed under reduced pressure. The aqueous residue was extracted three times with 40 ml ethyl acetate. The combined organic extracts were washed first with water (20 ml) and then with brine (15 ml), then dried ($MgSO_4$). The solvent was evaporated under reduced pressure to give a white solid. The crude residue was purified by chromatography on silica gel 60G (ethyl acetate/petroleum ether 40-60° C., 1/9 then 1/4) to yield first 59 mg (6%) betulonal as a white solid, then 880 mg (86%) betulonic acid 1 as a white solid.

Betulonal ($C_{30}H_{46}O_2$):

m.p.: 121-123° C. (AcOEt/EP) [N. G. Komissarova et al., *Chem. Nat. Compounds*, 2002, vol. 38, p. 58-61]

$^1$H-NMR (CDCl$_3$): 0.91 (s, 3H, Me (26)), 0.94 (s, 3H, Me (25)), 0.97 (s, 3H, Me (27)), 1.00 (s, 3H, Me (24)), 1.05 (s, 3H, Me (23)), 1.15-1.50 (m, 12H), 1.68 (s, 3H, Me (29)), 1.66-1.89 (m, 5H), 1.96-2.03 (m, 2H), 2.05-2.14 (m, 2H), 2.32-2.55 (m, 3H), 2.94-2.98 (m, 1H), 4.61 (s, 1H, =CH$_2$), 4.74 (s, 1H, =CHO), 9.65 (d, 1H, J=1.5, —CHO)

$^{13}$C-NMR (CDCl$_3$): see Table 1

IR (KBr, cm$^{-1}$): 3600, 2700, 1730, 1705, 1645, 870 [N. G. Komissarova et al., *Chem. Nat. Compounds*, 2002, vol. 38, p. 58-61]

$[\alpha]_D^{25}$=+53.8° (c=1.77×10$^{-3}$ g/cm$^3$, CHCl$_3$) [M. Zakaria et al., *Phytochemistry*, 1994, vol. 23, p. 1484]

Betulonic Acid 1 ($C_{30}H_{46}O_3$)

m.p.: 246-248° C. (AcOEt/EP) [N. I. Petrenko et al., *Chem. Nat. Compounds*, 2002, vol. 38, p. 331-339]

$^1$H-NMR (CDCl$_3$): 0.92 (s, 3H, Me (26)), 0.96 (s, 3H, Me (25)), 0.98 (s, 3H, Me (27)), 1.00 (s, 3H, Me (24)), 1.06 (s, 3H, Me (23)), 1.15-1.49 (m, 14H), 1.55-1.69 (m, 3H), 1.68 (s, 3H, Me (29)), 1.87-2.00 (m, 3H), 2.18-2.51 (m, 4H), 2.97-3.03 (m, 1H, H—C (19)), 4.60 (s, 1H, H—C (30)), 4.73 (s, 1H, H—C (30))

$^{13}$C-NMR (CDCl$_3$): see Table 1

$[\alpha]_D^{20}$=+43° (c=4.05×10$^{-3}$ g/cm$^{-3}$, CHCl$_3$) [N. I. Petrenko et al., *Chem. Nat. Compounds*, 2002, vol. 38, p. 331-339]

Example 2 synthesis of α-cholesteryl 3-oxo-lup-20(29)-en-28-oate 2a (Mitsunobu reaction)

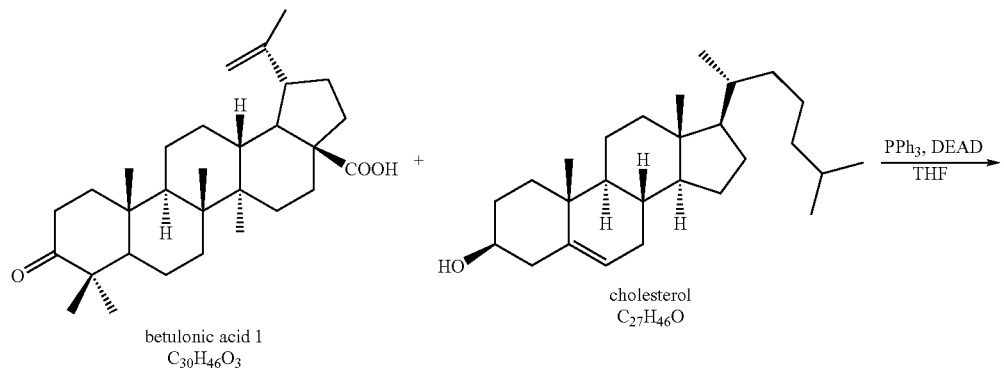

betulonic acid 1
$C_{30}H_{46}O_3$ cholesterol
$C_{27}H_{46}O$

PPh$_3$, DEAD
THF

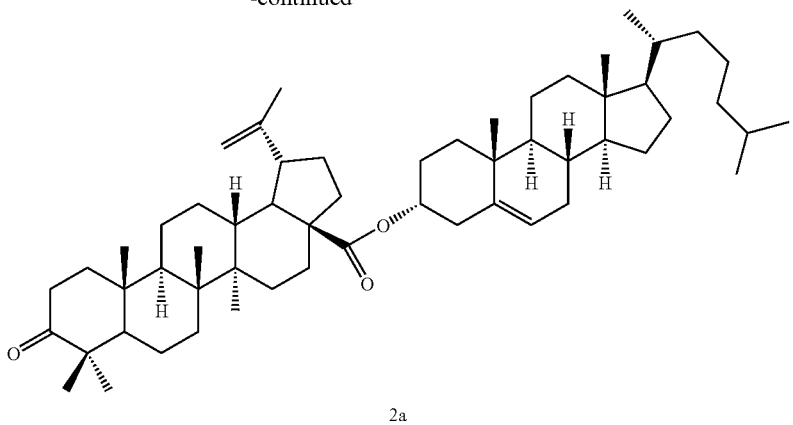

2a

In a 100 ml round-bottomed flask, equipped with a magnetic stirring bar and a septum fitted with a nitrogen inlet, was placed 772 mg (2.0 mmol) cholesterol in 30 ml dry THF. The flask was cooled with an ice-acetone bath. 1.047 g (3.99 mmol) triphenyl phosphine and 1 g (2.199 mmol) betulonic acid 1 were added, in that order. Then 627 µl (3.99 mmol) diethyl azadicarboxylate (DEAD) was added dropwise by syringe. Then the solution was warmed to room temperature and stirred for 17 hours. The solution was quenched with water (30 ml) and extracted three times with ethyl acetate. The combined organic extracts were dried (MgSO$_4$) and the solvent was evaporated under reduced pressure to give a yellow solid. The crude residue was purified by chromatography on silica gel 60G (ethyl acetate/petroleum ether 40-60° C., 5/95 then 1/9) to yield 858 mg (52%) 2a as a white solid.

α-Cholesteryl 3-oxo-lup-20(29)-en-28-oate 2a
($C_{57}H_{90}O_3$)

$^1$H-NMR (CDCl$_3$): 0.69 (s, 3H, Me (49)), 0.85 (d, 3H, J=1.2, Me (57)), 0.86 (d, 3H, J=1.2, Me (56)), 0.92 (s, 3H, Me (26)), 0.93 (d, 3H, J=6.5, Me (51)), 0.95 (s, 3H, Me (25)), 0.97 (s, 3H, Me (27)), 1.02 (s, 3H, Me (24)), 1.04 (s, 3H, Me (48)), 1.07 (s, 3H, Me (23)), 1.69 (s, 3H, Me (30)), 0.84-2.44 (m, 49H), 2.49-2.55 (m, 3H), 3.02 (dt, 1H, J=4.2, 6.6, H—C (19)), 4.61 (s, 1H, H—C (29)), 4.72 (s, 1H, H—C (30)), 5.09 (m, 1H, H—C (33)), 5.30 (d, 1H, J=5.1, H—C (36))

$^{13}$C-NMR (CDCl$_3$): see Table 1

IR (KBr, cm$^{-1}$): 2925 s, 1709 s, 1667 w, 1633 w, 1460 s, 1378 s, 1190 s, 1139 s

MS (APCI positive): 823 [M+H]$^+$ (100%), 805 [M+H—H$_2$O]$^+$ (9%), 455 [M+H-Cholesteryl]$^+$ (12%), 437 [M+H-Cholesteryl-H$_2$O]$^+$ (33%), 369 [M+H-Betulonic Acid]$^+$ (64%)

$[\alpha]_D^{20}$=−7.2° (c=5.96×10$^{-3}$ g/cm$^3$, CH$_2$Cl$_2$)

Example 3 synthesis of farnesyl 3-oxo-lup-20(29)-en-28-oate 2b
(Mitsunobu reaction)

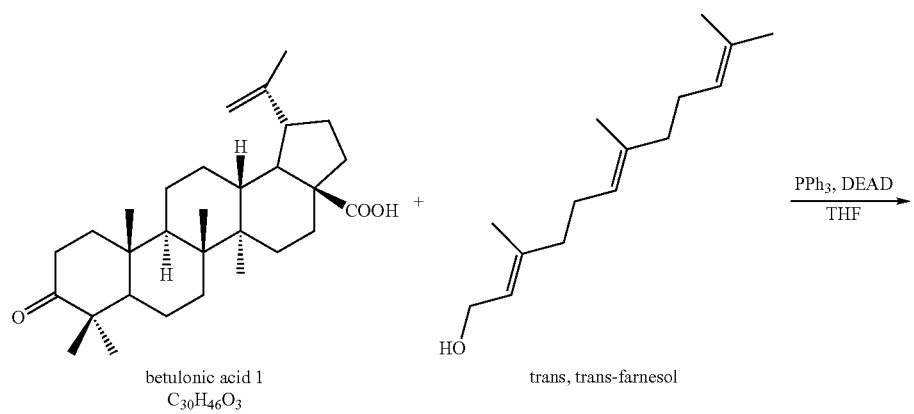

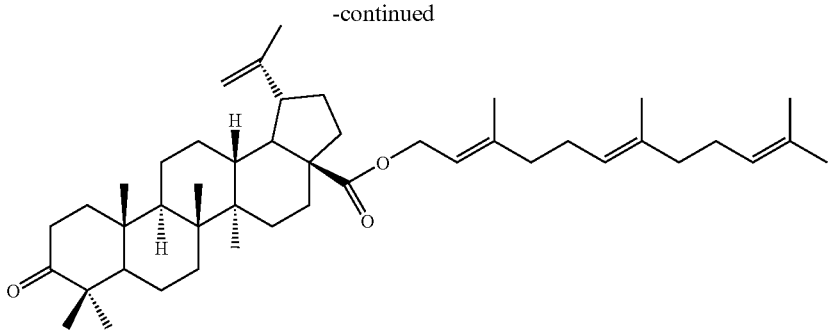

2b

In a 50 ml round-bottomed flask, equipped with a magnetic stirring bar and a septum fitted with a nitrogen inlet, was placed 70 mg (0.314 mmol) trans,trans-farnesol in 10 ml dry THF. The flask was cooled with an ice-acetone bath. 165 mg (0.629 mmol) triphenyl phosphine and 150 mg (0.330 mmol) betulonic acid 1 were added, in that order. Then 274 μl (0.838 mmol) diethyl azadicarboxylate (DEAD) in toluene (40% w/w) was added dropwise by syringe. Then the solution was warmed to room temperature and stirred for 17 hours. The solution was quenched with water (25 ml) and extracted three times with diethyl ether. The combined organic extracts were dried (MgSO$_4$) and the solvent was evaporated under reduced pressure to give a yellow solid. The crude residue was purified by chromatography on silica gel 60G (ethyl acetate/petroleum ether 40-60° C., 5/95 then 1/9) to yield 70 mg (34%) 2b as a pale yellow oil.

Farnesyl 3-oxo-lup-20(29)-en-28-oate 2b ($C_{45}H_{70}O_3$)

$^1$H-NMR (CDCl$_3$): 0.92 (s, 3H, Me (26)), 0.94 (s, 3H, Me (25)), 0.97 (s, 3H, Me (27)), 1.02 (s, 3H, Me (24)), 1.06 (s, 3H, Me (23)), 1.60 (s, 6H, Me (44) & Me (45)), 1.68 (s, 6H, Me (30) & Me (43)), 1.72 (s, 3H, Me (42)), 0.90-1.50 (m, 16H), 1.87-2.10 (m, 12H), 2.15-2.25 (m, 2H), 2.43 (m, 2H—C (2)), 3.01 (dt, 1H, J=4.3, 10.8, H—C (19)), 4.59 (m, 2H—C (31)), 4.61 (d, 1H, J=1.6, H—C (29)), 4.72 (d, 1H, J=1.6, H—C (29)), 5.08 (m, 1H, H—C (36)), 5.10 (m, 1H, H—C (40)), 5.36 (t, 1H, J=6.9, H—C (32))

$^{13}$C-NMR (CDCl$_3$): see Table 1

Example 4 synthesis of acetoxymethyl 3-oxo-lup-20(29)-en-28-oate 2c (nucleophilic substitution)

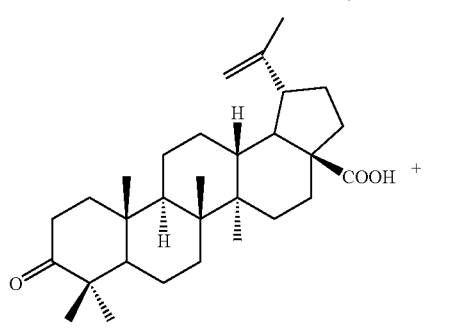

betulonic acid 1
$C_{30}H_{46}O_3$

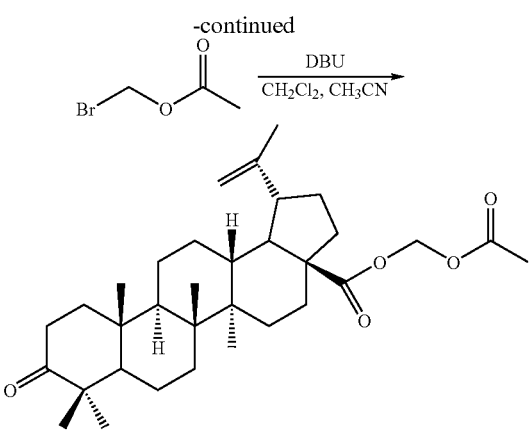

2c

In a 50 ml round-bottomed flask, equipped with a magnetic stirring bar and a septum fitted with a nitrogen inlet, was placed 1.88 g (4.04 mmol) betulonic acid 1, 435 μl (4.44 mmol) bromomethyl acetate, 11.7 ml dichloromethane and 3.9 ml acetonitrile. The flask was cooled with an ice-acetone bath and 416 μl (4.24 mmol) diazabicyclo[5.4.0]undecene (DBU) was added dropwise by syringe. Then the solution was warmed to room temperature and stirred for 16 hours, then concentrated in the presence of silica gel 60G (300 mg) under reduced pressure. The crude residue was purified by chromatography on silica gel 60G (ethyl acetate/petroleum ether 40-60° C., 1/9 then 1/4) to yield 1.86 g (85.3%) 2c as a white solid.

Acetoxymethyl 3-oxo-lup-20(29)-en-28-oate 2c ($C_{33}H_{50}O_5$)

m.p.: 86-91° C. (CH$_3$OH) [M. Urban et al., Bioorg. Med. Chem., 2005, vol. 13, p. 5527-5535]

$^1$H-NMR (CDCl$_3$): 0.90 (s, 3H, Me (26)), 0.94 (s, 3H, Me (25)), 0.96 (s, 3H, Me (27)), 1.00 (s, 3H, Me (24)), 1.05 (s, 3H, Me (23)), 1.10-1.60 (m, 14H), 1.66 (s, 3H, Me (30)), 1.64-1.75 (m, 3H), 1.82-1.95 (m, 3H), 2.08 (s, 3H, Me (33)), 2.23 (m, 2H), 2.42 (m, 2H—C (2)), 2.98 (dt, 1H, J=4.2, 7.0, H—C (19)), 4.59 (m, 1H, H—C (29)), 4.72 (s, 1H, H—C (29)), 5.69 (d, 1H, J=5.4, H—C (31)), 5.78 (d, 1H, J=5.4, H—C (31))

$^{13}$C-NMR (CDCl$_3$): see Table 1

IR (KBr, cm$^{-1}$): 2930 s, 1765 s, 1742 s, 1704 s, 1632 w, 1458 s, 1369 s, 1215 s, 1105 s, 1002 s, 975 s, 877 m

MS (ESI positive): 590 [M+Na+CH$_3$CN]$^+$ (51%), 549 [M+Na]$^+$ (100%), 527 [M+H]$^+$ (24%)

$[\alpha]_D^{20}=+31°$ (c=0.32×10⁻³ g/cm³, CHCl₃) [M. Urban et al., *Bioorg. Med. Chem.*, 2005, vol. 13, p. 5527-5535]

Example 5 synthesis of α-cholesteryl 3β-hydroxy-lup-20(29)-en-28-oate 3a-β (reduction)

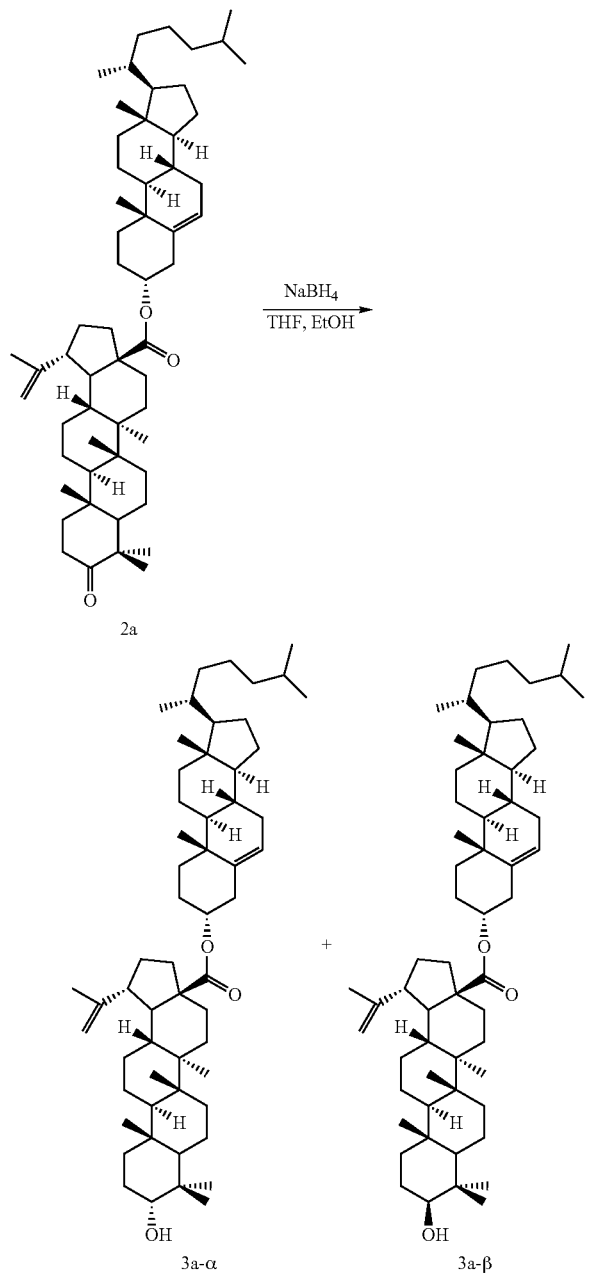

In a 50 ml round-bottomed flask, equipped with a magnetic stirring bar and a septum fitted with a nitrogen inlet, was placed 688 mg (0.8356 mmol) derivative 2a, 10 ml THF and 10 ml ethanol 96%. The flask was cooled with an ice-acetone bath and 150 mg (3.947 mmol) sodium borohydride was added by spatula. Then the solution was warmed to room temperature and stirred for 1.5 hours, then concentrated in the presence of silica gel 60G (300 mg) under reduced pressure. The crude residue was purified by chromatography on silica gel 60G (ethyl acetate/petroleum ether 40-60° C., 5/95 then 1/9) to yield 36 mg (5%) 3a-α as a white solid, then 639 mg (93%) 3a-β as a white solid (ratio 3a-α/3a-β=5.4/94.6).

α-Cholesteryl 3α-hydroxy-lup-20(29)-en-28-oate
3a-α(C₅₇H₉₂O₃)

¹H-NMR (CDCl₃): 0.69 (s, 3H, Me (49)), 0.82 (s, 6H, Me (24), Me (26)), 0.85 (d, 3H, J=1.2, Me (57)), 0.87 (d, 3H, J=1.2, Me (56)), 0.91 (s, 3H, Me (48)), 0.92 (d, 3H, J=6.5, Me (51)), 0.93 (s, 3H, Me (25)), 0.97 (s, 3H, Me (27)), 1.03 (s, 3H, Me (23)), 1.69 (s, 3H, Me (30)), 0.84-2.30 (m, 51H), 2.50 (d, 1H, J=15.1, H—C (34)), 3.01 (dt, 1H, J=4.3, 11.2, H—C (19)), 3.38 (br, 1H, H—C (3)), 4.60 (d, 1H, J=1.2, H—C (29)), 4.72 (d, 1H, J=1.2, H—C (29)), 5.08 (br, 1H, H—C (33)), 5.30 (d, 1H, J=5.1, H—C (36))
¹³C-NMR (CDCl₃): see Table 1

α-Cholesteryl 3β-hydroxy-lup-20(29)-en-28-oate
3a-β (C₁₇H₉₂O₃)

¹H-NMR (CDCl₃): 0.69 (s, 3H, Me (49)), 0.75 (s, 3H, Me (24)), 0.81 (s, 3H, Me (26)), 0.85 (d, 3H, J=1.2, Me (57)), 0.87 (d, 3H, J=1.2, Me (56)), 0.90 (s, 3H, Me (48)), 0.92 (d, 3H, J=6.5, Me (51)), 0.96 (s, 3H, Me (25)), 0.97 (s, 3H, Me (27)), 1.03 (s, 3H, Me (23)), 1.69 (s, 3H, Me (30)), 0.84-2.30 (m, 51H), 2.50 (d, 1H, J=15.1, H—C (34)), 3.01 (dt, 1H, J=4.3, 11.2, H—C (19)), 3.18 (dd, 1H, J=5.1, 10.7, H—C (3)), 4.60 (s, 1H, H—C (29)), 4.72 (d, 1H, J=1.8, H—C (29)), 5.08 (br, 1H, H—C (33)), 5.30 (s, 1H, —OH), 5.31 (d, 1H, J=5.1, H—C (36))
¹³C NMR (CDCl₃): see Table 1
IR (KBr, cm⁻¹): 3445 m, 2925 s, 1712 s, 1458 s, 1373 s, 1177 s, 1141 s, 1035 s, 907 s, 732 s
MS (ESI positive): 411 [M+H-Cholesteryl-CO₂]⁺ (100%)

Example 6 synthesis of acetoxymethyl 3β-hydroxy-lup-20(29)-en-28-oate 3c-β (reduction)

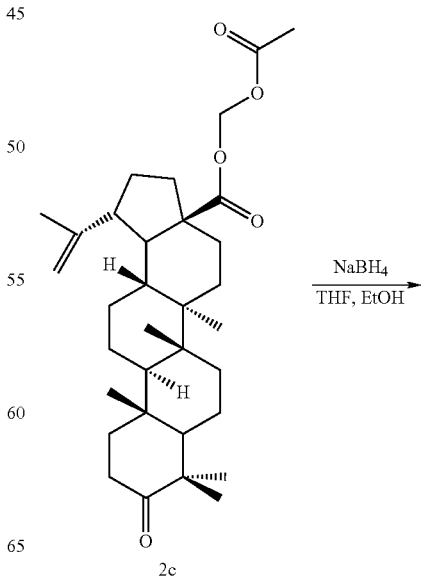

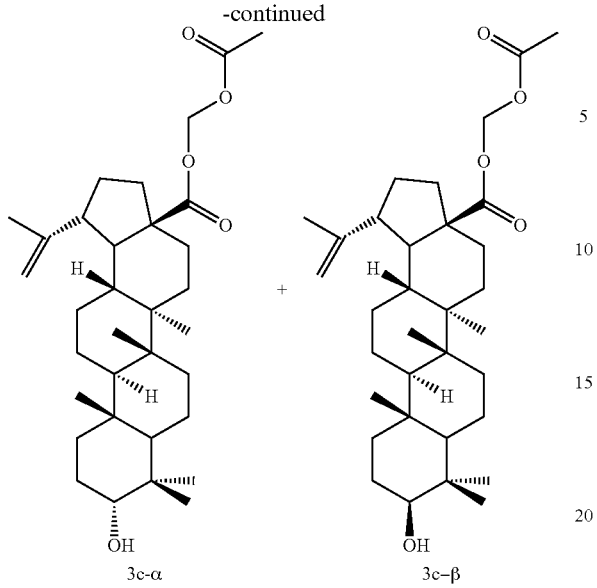

In a 50 ml round-bottomed flask, equipped with a magnetic stirring bar and a septum fitted with a nitrogen inlet, was placed 2.13 g (4.04 mmol) derivative 2c, 20 ml THF and 1 ml ethanol 96%. The flask was cooled with an ice-acetone bath and 442 mg (11.6 mmol) sodium borohydride was added by spatula. Then the solution was warmed to room temperature and stirred for 2 hours, then concentrated in the presence of silica gel 60G (500 mg) under reduced pressure. The crude residue was purified by chromatography on silica gel 60G (ethyl acetate/petroleum ether 40-60° C., 1/9 then 1/4) to yield 64.7 mg (3.0%) 3c-α as a white solid, then 1064 mg (49.7%) 3c-β as a white solid (ratio 3c-α/3c-β=5.7/94.3).

Acetoxymethyl 3α-hydroxy-lup-20(29)-en-28-oate 3c-α($C_{33}H_{52}O_5$)

$^1$H-NMR ($CDCl_3$): 0.76 (s, 3H, Me (24)), 0.82 (s, 3H, Me (26)), 0.92 (s, 3H, Me (25)), 0.96 (s, 6H, Me (23), Me (27)), 1.10-1.60 (m, 16H), 1.68 (s, 3H, Me (30)), 1.64-1.75 (m, 4H), 1.82-1.95 (m, 3H), 2.10 (s, 3H, Me (33)), 2.23 (m, 2H), 2.98 (dt, 1H, J=4.2, 7.0, H—C (19)), 3.38 (m, 1H, H—C (3)), 4.60 (s, 1H, H—C (29)), 4.73 (s, 1H, H—C (29)), 5.71 (d, 1H, J=5.4, H—C (31)), 5.79 (d, 1H, J=5.4, H—C (31))

Acetoxymethyl 3β-hydroxy-lup-20(29)-en-28-oate 3c-β ($C_{33}H_{52}O_5$)

m.p.: 178-179° C. (AcOEt/EP)
$^1$H-NMR ($CDCl_3$): 0.73 (s, 3H, Me (24)), 0.80 (s, 3H, Me (26)), 0.90 (s, 3H, Me (25)), 0.94 (s, 6H, Me (23), Me (27)), 1.10-1.60 (m, 16H), 1.68 (s, 3H, Me (30)), 1.64-1.75 (m, 4H), 1.82-1.95 (m, 3H), 2.10 (s, 3H, Me (33)), 2.23 (m, 2H), 2.98 (dt, 1H, J=4.2, 7.0, H—C (19)), 3.16 (dd, 1H, J=5.4, 10.8, H—C (3)), 4.60 (s, 1H, H—C (29)), 4.73 (s, 1H, H—C (29)), 5.70 (d, 1H, J=5.4, H—C (31)), 5.79 (d, 1H, J=5.4, H—C (31))
$^{13}$C-NMR ($CDCl_3$): see Table 1
IR (KBr, $cm^{-1}$): 3530 m, 2920 s, 1761 s, 1708 s, 1633 w, 1444 s, 1364 s, 1224 s, 1137 s, 1043 s, 970 s, 874 m
MS (ESI positive): 511 [M+H—$H_2O$]$^+$ (16%), 411 [M+H—$CO_2CH_2O_2CCH_3$]$^+$ (100%)
$[\alpha]_D^{20}$=+10.9° (c=4.12×10$^{-3}$ g/cm$^3$, $CH_2Cl_2$)

Example 7 synthesis of α-cholesteryl 3β-(methoxypolyethylene glycol acetoxy)-lup-20(29)-en-28-oate 4a-β (via CMPI ester methodology)

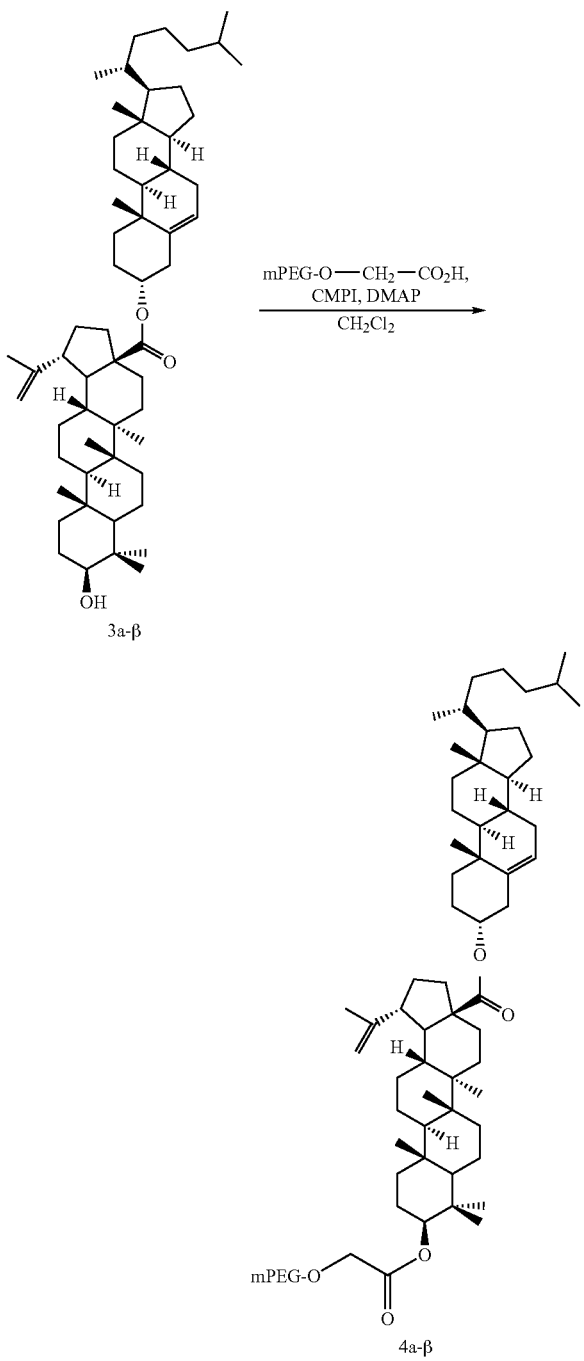

In a dry 50 ml round-bottomed flask, equipped with a magnetic stirring bar and a septum fitted with nitrogen inlet, was placed 350 mg (0.4240 mmol) derivative 3a-β in 25 ml dry dichloromethane. The flask was cooled with an ice-acetone bath and 921 mg (0.1843 mmol) methoxypolyethylene glycol 5,000 acetic acid (mPEG-O—CH$_2$—CO$_2$H), 184 mg (0.7208 mmol) 2-chloro-1-methylpyridinium iodide (CMPI) and 184 mg (1.509 mmol) DMAP were added, in that order, and stirred for 20 minutes at −5° C. Then the solution was warmed to room temperature and stirred for 48 hours. The solution was quenched with water (15 ml) and extracted three times with dichloromethane. The combined organic extracts were dried (MgSO$_4$). The solvent was evaporated under reduced pressure to yield a yellow oil that was recrystallised twice from propan-2-ol (125 ml), then lyophilized to give a white solid 4a-β (683 mg, 63.8%).

α-Cholesteryl 3β-(methoxypolyethylene glycol acetoxy)-lup-20(29)-en-28-oate 4a-β

$^1$H-NMR (CDCl$_3$): 0.67 (s, 3H, Me (49)), 0.81 (s, 3H, Me (24)), 0.82 (s, 3H, Me (26)), 0.84 (s, 3H, Me (25)), 0.86 (d, 3H, J=1.2, Me (57)), 0.88 (d, 3H, J=1.2, Me (56)), 0.90 (s, 3H, Me (48)), 0.91 (d, 3H, J=6.5, Me (51)), 0.93 (s, 3H, Me (27)), 1.02 (s, 3H, Me (23)), 1.67 (s, 3H, Me (30)), 0.84-2.30 (m, 51H), 2.48 (d, 1H, J=15.1, H—C (37)), 3.01 (dt, 1H, J=4.3, 11.2, H—C (19)), 3.36 (s, 3H, MeO from mPEG), 3.39 (m, 2H), 3.62 (br, PEG), 3.86 (m, 2H), 4.11 (s, 2H, —OCOCH$_2$OPEG), 4.55 (m, 1H, H—C (3)), 4.59 (s, 1H, H—C (29)), 4.70 (d, 1H, J=1.8, H—C (29)), 5.07 (br, 1H, H—C (33)), 5.30 (d, 1H, J=5.1, H—C (36))

$^{13}$C-NMR (CDCl$_3$): see Table 1

Example 8 synthesis of acetoxymethyl 3β-(methoxypolyethylene glycol acetoxy)-lup-20(29)-en-28-oate 4c-β (via CMPI ester methodology)

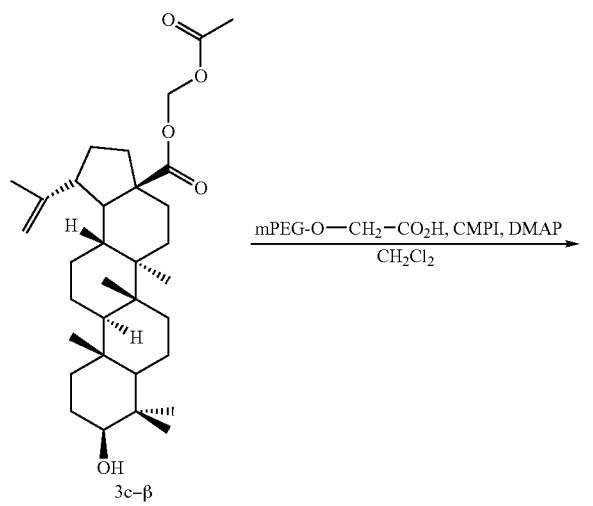

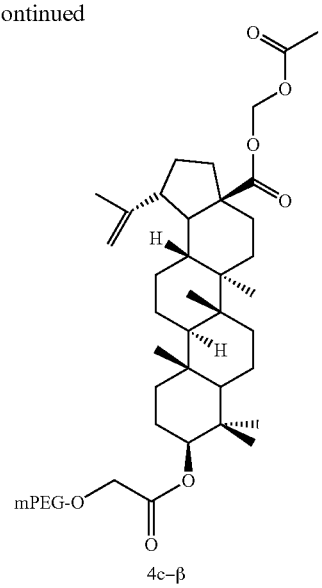

In a dry 50 ml round-bottomed flask, equipped with a magnetic stirring bar and a septum fitted with nitrogen inlet, was placed 250 mg (0.4728 mmol) derivative 3c-β in 25 ml dry dichloromethane. The flask was cooled with an ice-acetone bath and 1.03 g (0.2073 mmol) methoxypolyethylene glycol 5,000 acetic acid (mPEG-O—CH$_2$—CO$_2$H), 205 mg (0.8038 mmol) 2-chloro-1-methylpyridinium iodide (CMPI) and 208 mg (1.702 mmol) DMAP were added, in that order, and stirred for 20 minutes at −5° C. Then the solution was warmed to room temperature and stirred for 48 hours. The solution was quenched with water (15 ml) and extracted three times with dichloromethane. The combined organic extracts were dried (MgSO$_4$). The solvent was evaporated under reduced pressure to yield a yellow oil that was recrystallised twice from propan-2-ol (125 ml), then lyophilized to give a white solid 4c-β (751 mg, 50%).

Acetoxymethyl 3β-(methoxypolyethylene glycol acetoxy)-lup-20(29)-en-28-oate 4c-β

$^1$H-NMR (CDCl$_3$): 0.80 (s, 3H, Me (24)), 0.82 (s, 6H, Me (25), Me (26)), 0.90 (s, 3H, Me (27)), 0.94 (s, 3H, Me (23)), 1.10-1.60 (m, 16H), 1.66 (s, 3H, Me (30)), 1.64-1.75 (m, 4H), 1.82-1.95 (m, 3H), 2.08 (s, 3H, Me (33)), 2.23 (m, 2H), 2.98 (dt, 1H, J=4.2, 7.0, H—C (19)), 3.36 (s, 3H, MeO from in PEG), 3.39 (m, 2H), 3.62 (br, PEG), 3.86 (m, 2H), 4.11 (s, 2H, —OCOCH$_2$OPEG), 4.53 (m, 1H, H—C (3)), 4.59 (s, 1H, H—C (29)), 4.71 (s, 1H, H—C (29)), 5.69 (d, 1H, J=5.4, H—C (31)), 5.78 (d, 1H, J=5.4, H—C (31))

$^{13}$C-NMR (CDCl$_3$): see Table 1

Example 9 synthesis of 3-oxo-lupan-28-oic acid (20,29-dihydro-betulonic acid) 5

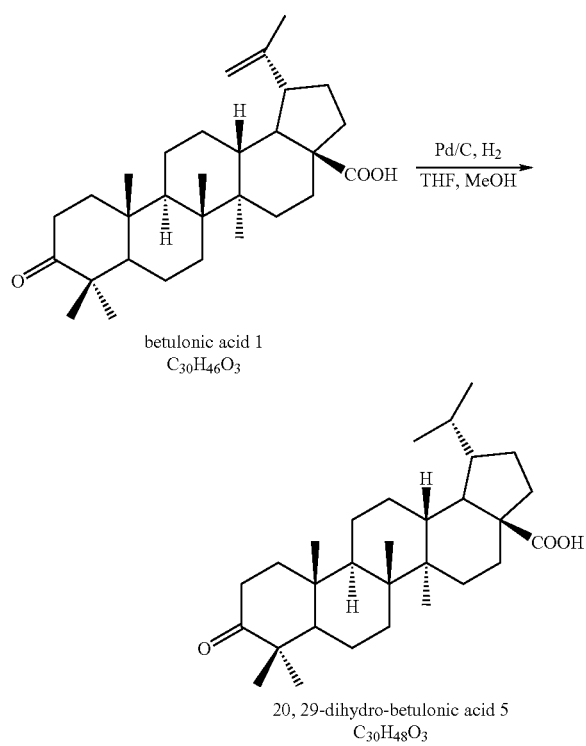

In a 250 ml round-bottomed flask, equipped with a septum fitted with a hydrogen inlet, was placed 15 g (32.989 mmol) betulonic acid 1 in a mixture of 110 ml anhydrous THF and 10 ml methanol. This reaction mixture was hydrogenated at 4 atm and room temperature over 3 g Pd/C (10% w/w). After 24 hours, the catalyst was filtered off and the solution concentrated under reduced pressure to give a white solid. The solid was recrystallised from acetone to give 13.04 g (87%) 20,29-dihydro-betulonic acid 5.

3-Oxo-lupan-28-oic acid (20,29-dihydro-betulonic acid) 5 ($C_{30}H_{48}O_3$)

m.p.: 185-186° C. (AcOEt/EP)

$^1$H-NMR (CDCl$_3$): 0.75 (d, 3H, J=6.9, Me (29)), 0.84 (d, 3H, J=6.9, Me (30)), 0.92 (s, 3H, Me (26)), 0.95 (s, 6H, Me (25), Me (27)), 1.00 (s, 3H, Me (24)), 1.06 (s, 3H, Me (23)), 1.15-1.95 (m, 18H), 2.23 (m, 4H), 2.43 (m, 2H, 2H—C (2))

$^{13}$C-NMR (CDCl$_3$): see Table 1

IR (KBr, cm$^{-1}$): 3380 m, 2930 s, 1683 s, 1451 s, 1383 s, 1364 s, 1236 s, 1194 s, 1165 s, 1137 s, 1100 s, 1017 m, 982 m, 957 m, 811 m

MS (ESI negative): 455 [M–H$^+$] (100%)

$[\alpha]_D^{20}$=+4.1° (c=3.44×10$^{-3}$ g/cm$^3$, CH$_2$Cl$_2$)

Example 10 synthesis of α-cholesteryl 3-oxo-lupan-28-oate 6a (Mitsunobu reaction)

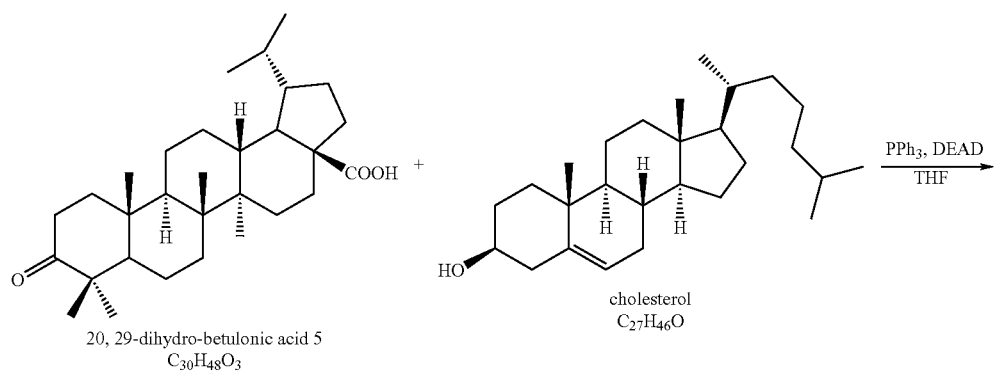

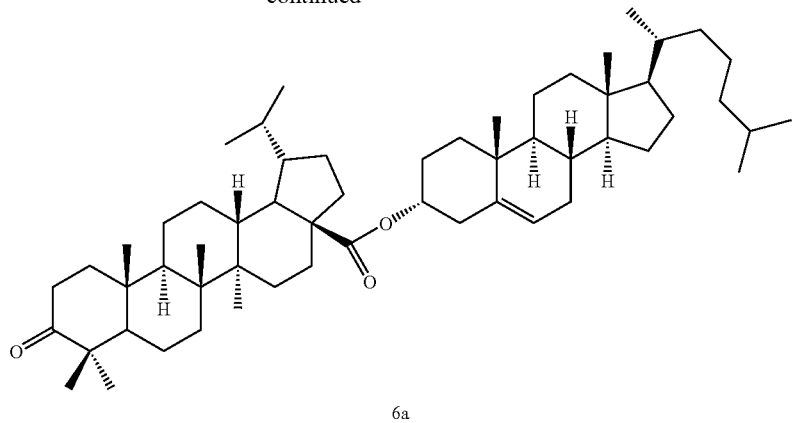

6a

In a 500 ml round-bottomed flask, equipped with a magnetic stirring bar and a septum fitted with a nitrogen inlet, was placed 25 g (54.74 mmol) 20,29-dihydro-betulonic acid 5 in 950 ml dry THF. The flask was cooled with an ice-acetone bath and 27.35 g (104.26 mmol) triphenyl phosphine, 20.16 g (52.13 mmol) cholesterol were added, in that order. Then 47.8 ml (104.26 mmol) diethyl azadicarboxylate (DEAD, 40% solution in toluene) was added dropwise by syringe. Then the solution was warmed to room temperature and stirred for 48 hours. The solution was quenched with distilled water (500 ml) and extracted three times with 500 ml ethyl acetate. The combined organic extracts were dried (MgSO$_4$) and the solvent was evaporated under reduced pressure to give a yellow solid. The crude residue was purified by chromatography on silica gel 60G (ethyl acetate/petroleum ether 40-60° C., 5/95 then 1/9) to yield 27.01 g (63%) 6a as a white solid.

α-Cholesteryl 3-oxo-lupan-28-oate 6a ($C_{57}H_{92}O_3$)

$^1$H-NMR (CDCl$_3$): 0.67 (s, 3H, Me (49)), 0.73 (d, 3H, J=6.9, Me (29)), 0.84 (d, 3H, J=6.6, Me (30)), 0.84 (d, 3H, J=1.2, Me (57)), 0.86 (d, 3H, J=1.2, Me (56)), 0.91 (s, 3H, Me (26)), 0.92 (m, 3H, Me (51)), 0.93 (s, 3H, Me (25)), 0.94 (s, 3H, Me (27)), 1.01 (s, 3H, Me (24)), 1.02 (s, 3H, Me (48)), 1.06 (s, 3H, Me (23)), 0.84-2.44 (m, 51H), 2.42-2.48 (m, 3H), 5.06 (m, 1H, H—C (33)), 5.27 (d, 1H, J=5.1, H—C (36))
$^{13}$C-NMR (CDCl$_3$): see Table 1

Example 11 synthesis of acetoxymethyl 3-oxo-lupan-28-oate 6c (nucleophilic substitution)

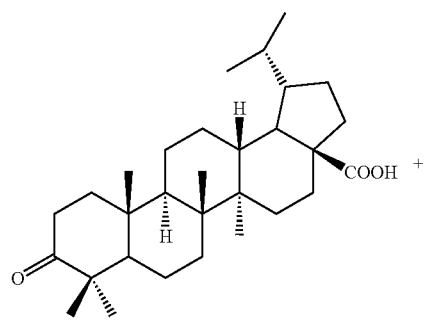

20, 29-dihydro-betulonic acid 5
$C_{30}H_{48}O_3$

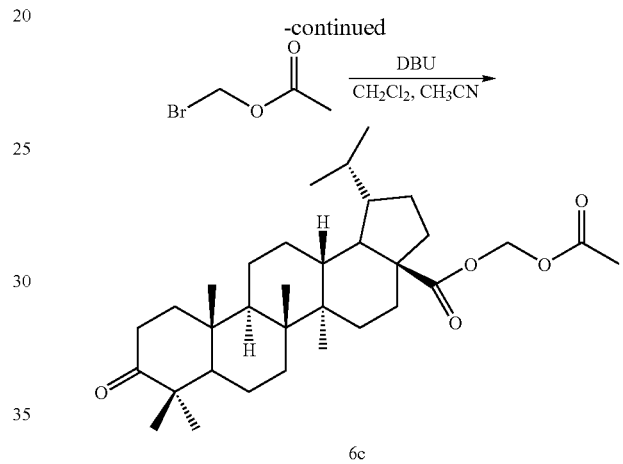

6c

In a 100 ml round bottomed flask, equipped with a magnetic stirring bar and a septum fitted with a nitrogen inlet, was placed 3.0 g (6.569 mmol) 20,29-dihydro-betulonic acid 5, 676 µl (6.897 mmol) bromomethyl acetate, 18 ml dichloromethane and 6 ml acetonitrile. The flask was cooled with an ice-acetone bath and 1.03 ml (6.897 mmol) diazabicyclo [5.4.0]undecene (DBU) was added dropwise by syringe. Then the solution was warmed to room temperature and stirred for 16 hours, then concentrated in the presence of silica gel 60G (600 mg) under reduced pressure. The crude residue was purified by chromatography on silica gel 60G (ethyl acetate/petroleum ether 40-60° C., 1/9 then 1/4) to yield 3.02 g (87.2%) 6c as a white solid.

Acetoxymethyl 3-oxo-lupan-28-oate 6c ($C_{33}H_{52}O_5$)

m.p.: 87-88° C. (CH$_3$OH)
$^1$H-NMR (CDCl$_3$): 0.74 (d, 3H, J=6.6, Me (29)), 0.84 (d, 3H, J=6.9, Me (30)), 0.93 (s, 3H, Me (26)), 0.95 (s, 6H, Me (25), Me (27)), 1.01 (s, 3H, Me (24)), 1.06 (s, 3H, Me (23)), 1.15-1.95 (m, 24H), 2.09 (s, 3H, Me (33)), 2.23 (m, 2H), 2.44 (m, 2H—C (2)), 5.69 (d, 1H, J=5.4, H—C (31)), 5.78 (d, 1H, J=5.4, H—C (31))
$^{13}$C-NMR (CDCl$_3$): see Table 1
IR (KBr, cm$^{-1}$): 2935 s, 1765 s, 1739 s, 1695 s, 1456 s, 1380 s, 1363 s, 1215 s, 1132 s, 1106 s, 1073 s, 1037 s, 1014 s, 997 s, 977 s
[α]$_D^{20}$=+8.6° (c=3.36×10$^{-3}$ g/cm$^3$, CH$_2$Cl$_2$)

Example 12 synthesis of α-cholesteryl 3β-hydroxy-lupan-28-oate 7a-β

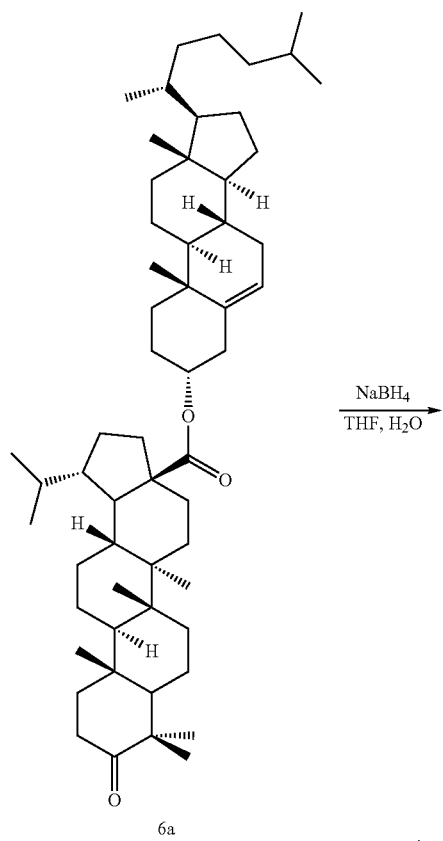

6a

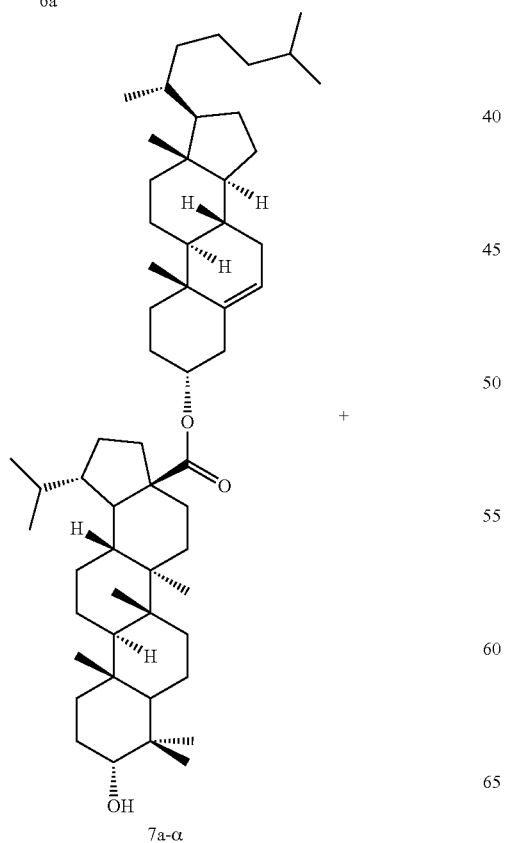

7a-α

+

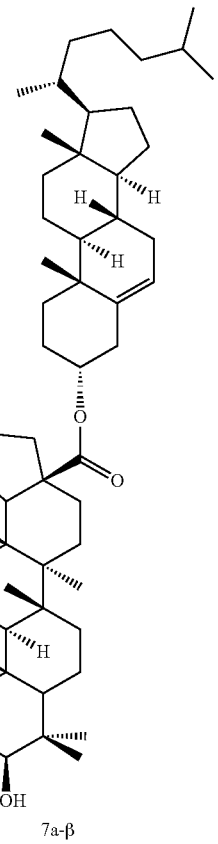

7a-β

In a 500 ml round-bottomed flask, equipped with a magnetic stirring bar and a septum fitted with a nitrogen inlet, was placed 25.0 g (30.289 mmol) derivative 6a in 200 ml THF. The flask was cooled with an ice-acetone bath and 1.15 g (30.289 mmol) borohydride sodium in 10 ml distilled water was added by syringe. Then the solution was warmed to room temperature and stirred for 1.5 hours, then concentrated in the presence of silica gel 60G (5 g) under reduced pressure. The crude residue was purified by chromatography on silica gel 60G (ethyl acetate/petroleum ether 40-60° C., 5/95 then 1/9) to yield 830 mg (3.3%) 7a-α as a white solid, then 20.259 g (81%) 7a-β as a white solid (ratio 7a-α/7a-β=3.9/96.1).

α-Cholesteryl 3β-hydroxy-lupan-28-oate 7a-β ($C_{17}H_{94}O_3$)

$^1$H-NMR (CDCl$_3$): 0.68 (s, 3H, Me (49)), 0.74 (d, 3H, J=6.6, Me (29)), 0.76 (s, 3H, Me (24)), 0.82 (s, 3H, Me (26)), 0.84 (d, 3H, J=6.6, Me (30)), 0.85 (d, 3H, J=1.2, Me (57)), 0.87 (d, 3H, J=1.2, Me (56)), 0.90 (s, 3H, Me (48)), 0.90 (m, 3H, Me (51)), 0.93 (s, 3H, Me (25)), 0.97 (s, 3H, Me (27)), 1.03 (s, 3H, Me (23)), 0.84-2.30 (m, 54H), 2.47 (d, 1H, J=15.0, H—C (37)), 3.19 (m, 1H, H—C (3)), 5.07 (br, 1H, H—C (33)), 5.31 (d, 1H, J=4.5, H—C (36))

$^{13}$C-NMR (CDCl$_3$): see Table 1

Example 13 synthesis of acetoxymethyl 3β-hydroxy-lupan-28-oate 7c-β

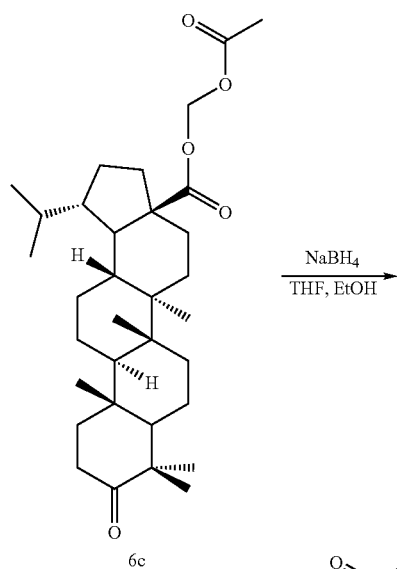

In a 100 ml round-bottomed flask, equipped with a magnetic stirring bar and a septum fitted with a nitrogen inlet, was placed 2.75 g (5.20 mmol) derivative 6c, 20 ml THF, 20 ml ethanol 96% and 1 ml distilled water. The flask was cooled with an ice-acetone bath and 198 mg (5.2 mmol) sodium borohydride was added by spatula. Then the solution was warmed to room temperature and stirred for 1 hour, then concentrated in the presence of neutral alumina WOELM-1 (500 mg) under reduced pressure. The crude residue was purified by chromatography on neutral alumina WOELM-1 (ethyl acetate/petroleum ether 40-60° C., 5/95 then 1/9 then 1/4) to yield 275 mg (10.0%) 7c-β as a white solid.

Acetoxymethyl 3β-hydroxy-lupan-28-oate 7c-β ($C_{33}H_{14}O_5$)

m.p.: 201-202° C. (AcOEt/EP)

$^1$H-NMR (CDCl$_3$): 0.73 (d, 3H, J=6.6, Me (29)), 0.75 (s, 3H, Me (24)), 0.82 (s, 3H, Me (26)), 0.84 (d, 3H, J=6.9, Me (30)), 0.91 (s, 3H, Me (25)), 0.94 (s, 3H, Me (27)), 0.96 (s, 3H, Me (23)), 1.10-1.60 (m, 23H), 2.09 (s, 3H, Me (33)), 2.23 (m, 2H), 3.18 (dd, 1H, J=5.1, 10.8, H—C (3)), 5.69 (d, 1H, J=5.4, H—C (31)), 5.78 (d, 1H, J=5.4, H—C (31))

$^{13}$C-NMR (CDCl$_3$): see Table 1

IR (KBr, cm$^{-1}$): 3535 m, 2940 s, 1762 s, 1747 s, 1708 s, 1446 s, 1362 s, 1225 s, 1165 s, 1145 s, 1098 s, 1042 s, 968 s $[\alpha]_D^{20}$=5.7° (c=2.09×10$^{-3}$ g/cm$^3$, CH$_2$Cl$_2$)

Example 14 synthesis of α-cholesteryl 3β-(methoxypolyethylene glycol acetoxy)-lupan-28-oate 8a-β

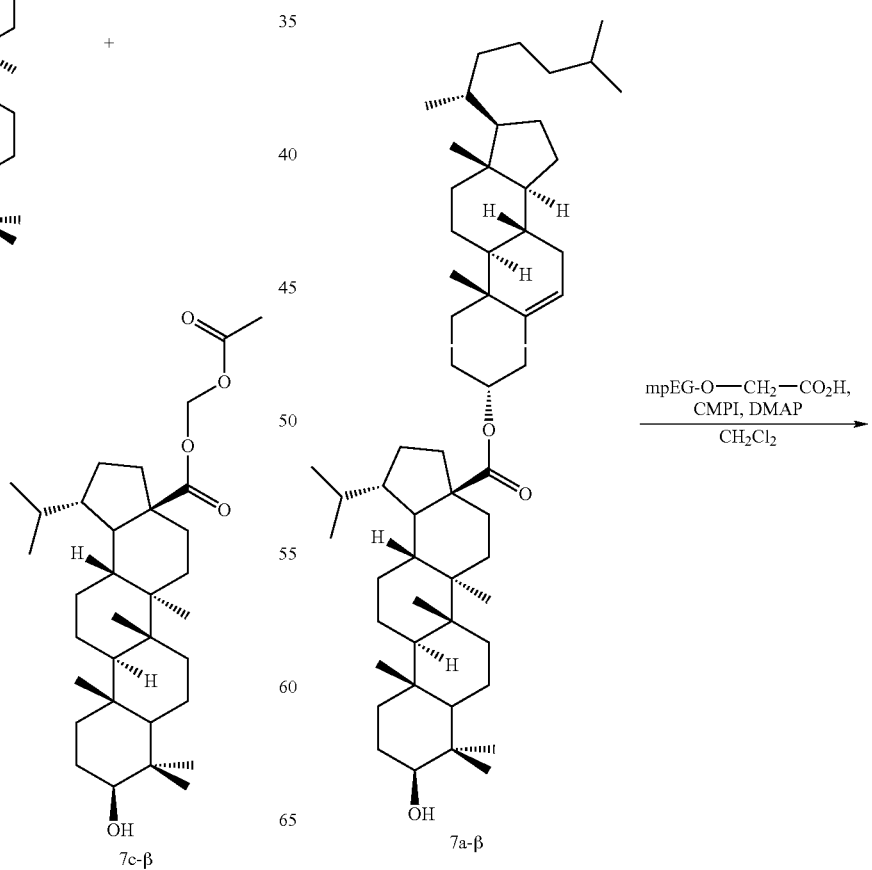

Example 15 synthesis of acetoxymethyl 3β-(methoxypolyethylene glycol acetoxy)-lupan-28-oate 8c-β

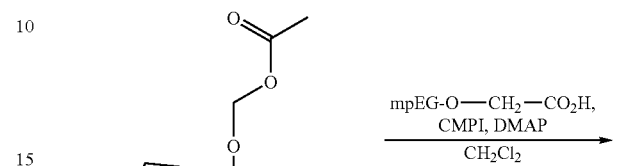

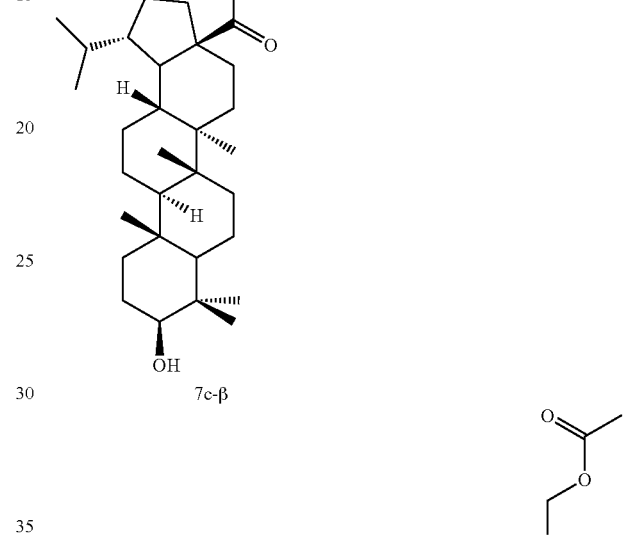

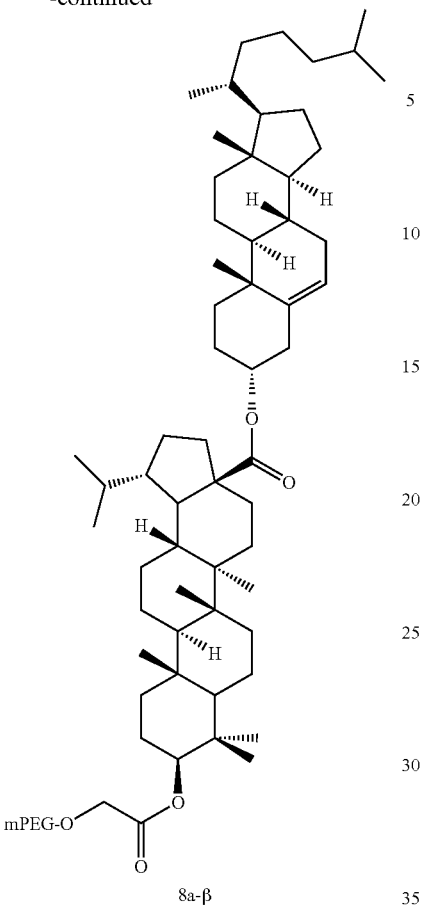

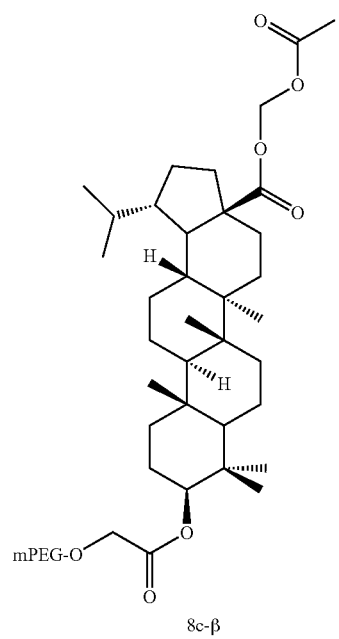

In a dry 2 l round-bottomed flask, equipped with a magnetic stirring bar and a septum fitted with nitrogen inlet, was placed 14.50 g (17.525 mmol) derivative 7a-β in 700 ml dry dichloromethane. The flask was cooled with an ice-acetone bath and 38.43 g (7.686 mmol) methoxypolyethylene glycol 5,000 acetic acid (mPEG-O—$CH_2$—$CO_2H$), 7.70 g (30.131 mmol) 2-chloro-1-methylpyridinium iodide (CMPI) and 7.36 g (60.261 mmol) DMAP were added, in that order, and stirred for 20 minutes at −5° C. Then the solution was warmed to room temperature and stirred for 48 hours. The solution was quenched with water (500 ml) and extracted three times (250 ml) with dichloromethane. The combined organic extracts were dried ($MgSO_4$). The solvent was evaporated under reduced pressure to yield a yellow oil that was recrystallised twice from propan-2-ol (500 ml), then lyophilized to give a white solid 8a-β (28.89 g, 68%).

α-Cholesteryl 3β-(methoxypolyethylene glycol acetoxy)-lupan-28-oate 8a-β

$^1$H-NMR ($CDCl_3$): 0.55 (s, 3H, Me (49)), 0.61 (d, 3H, J=6.6, Me (29)), 0.71 (m, 12H, Me (24), Me (26), Me (56), Me (57)), 0.74 (s, 6H, Me (25), Me (48)), 0.77 (m, 6H, Me (30), Me (51)), 0.80 (s, 3H, Me (27)), 0.89 (s, 3H, Me (23)), 0.84-2.30 (m, 52H), 2.36 (d, 1H, J=15.1, H—C (37)), 3.24 (s, 3H, MeO from mPEG), 3.27 (m, 2H), 3.51 (br, PEG), 3.74 (m, 2H), 3.99 (s, 2H, —$OCOCH_2OPEG$), 4.44 (m, 1H, H—C (3)), 4.93 (br, 1H, H—C (33)), 5.14 (br, 1H, H C (36)).

$^{13}$C-NMR ($CDCl_3$): see Table 1

In a dry 100 ml round-bottomed flask, equipped with a magnetic stirring bar and a septum fitted with nitrogen inlet, was placed 200 mg (0.3874 mmol) derivative 7c-β in 25 ml dry dichloromethane. The flask was cooled with an ice-acetone bath and 945 mg (0.1891 mmol) methoxypolyethylene glycol 5,000 acetic acid (mPEG-O—$CH_2$—$CO_2H$), 188 mg (0.7356 mmol) 2-chloro-1 methylpyridinium iodide (CMPI) and 183 mg (1.494 mmol) DMAP were added, in that order, and stirred for 20 minutes at −5° C. Then the solution was warmed to room temperature and stirred for 48 hours. The solution was quenched with water (25 ml) and extracted three times with 50 ml dichloromethane. The combined organic extracts were dried (MgSO₄). The solvent was evaporated under reduced pressure to yield a yellow oil that was recrystallised twice from propan-2-ol (125 ml), then lyophilized to give a white solid 8c-β (444 mg, 43%).

Acetoxymethyl 3β-(methoxypolyethylene glycol acetoxy)-lupan-28-oate 8c-β

¹H-NMR (CDCl₃): 0.72 (d, 3H, J=6.6, Me (29)), 0.80 (s, 3H, Me (24)), 0.81 (d, 3H, J=6.9, Me (30)), 0.82 (s, 6H, Me (26), Me (23)), 0.90 (s, 3H, Me (25)), 0.92 (s, 3H, Me (27)), 1.10-1.60 (m, 23H), 2.07 (s, 3H, Me (33)), 2.23 (m, 2H), 3.36 (s, 3H, MeO from mPEG), 3.39 (m, 2H), 3.62 (br, PEG), 3.86 (m, 2H), 4.11 (s, 2H, —OCOCH₂OPEG), 4.56 (m, 1H, H—C (3)), 5.67 (d, 1H, J=5.4, H—C ($\overline{31}$)), 5.76 (d, 1H, J=5.4, H—C (31))

¹³C-NMR (CDCl₃): see Table 1

Example 16 synthesis of α-cholesterol betulonate conjugated to mPEG (via DMAP carbamate methodology)

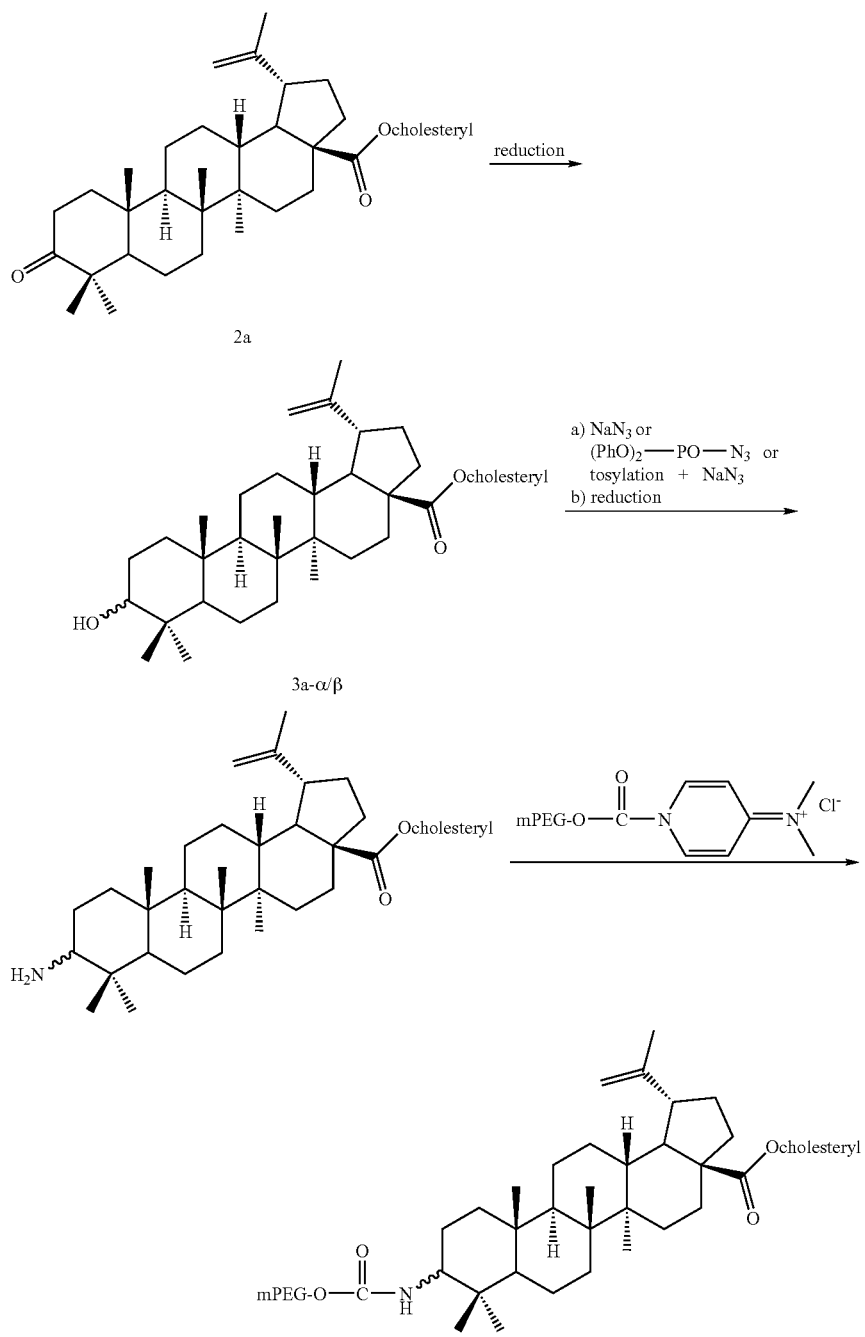

α-Cholesteryl betulonate 2a can be reduced to α-cholesteryl betulinate 3a-α/β using, for example, sodium borohydride or $M^+BHR_3^-$, wherein $M^+$ is $Na^+$, $Li^+$ or $K^+$, and R is independently a $C_{1-4}$ alkyl group such as s-butyl. The hydroxyl group of α-cholesteryl betulinate 3a-α/β can then be converted into an azide group using sodium azide or $(PhO)_2$—PO—$N_3$ or tosyl chloride followed by sodium azide. Subsequently the azide group can be reduced to an amino group, which can then be coupled to mPEG using, for example, an mPEG carbamate.

TABLE 1

$^{13}$C-NMR data

| Ci | Betulin | Betulonal | β-Betulinal | β-BetA | 1 | 2a | 2b | 2c |
|---|---|---|---|---|---|---|---|---|
| 1 | 38.74 | 39.75 | 38.73 | 38.67 | 39.73 | 39.79 | 39.83 | 39.72 |
| 2 | 26.97 | 33.75 | 27.39 | 26.77 | 33.72 | 33.91 | 33.76 | 33.74 |
| 3 | 78.84 | 218.00 | 78.99 | 78.60 | 218.41 | 218.29 | 218.24 | 218.13 |
| 4 | 38.82 | 47.42 | 38.85 | 38.67 | 47.44 | 47.48 | 47.46 | 47.43 |
| 5 | 55.29 | 55.07 | 55.31 | 55.28 | 55.03 | 55.09 | 55.10 | 55.06 |
| 6 | 18.30 | 19.73 | 18.26 | 18.15 | 19.73 | 20.95 | 19.79 | 19.76 |
| 7 | 34.20 | 34.23 | 34.33 | 34.21 | 34.24 | 34.41 | 34.28 | 34.23 |
| 8 | 40.88 | 40.89 | 40.82 | 40.54 | 40.74 | 40.85 | 40.79 | 40.76 |
| 9 | 50.38 | 49.94 | 50.40 | 50.44 | 49.95 | 50.01 | 50.07 | 50.01 |
| 10 | 37.11 | 37.00 | 37.17 | 37.01 | 37.03 | 37.04 | 37.05 | 37.02 |
| 11 | 20.83 | 21.39 | 20.74 | 20.75 | 21.49 | 21.60 | 21.58 | 21.52 |
| 12 | 25.21 | 25.66 | 25.53 | 25.41 | 25.60 | 25.92 | 25.69 | 25.61 |
| 13 | 37.28 | 38.87 | 38.69 | 38.18 | 38.64 | 38.99 | 38.46 | 38.43 |
| 14 | 42.68 | 42.72 | 42.55 | 42.29 | 42.60 | 42.73 | 42.60 | 42.56 |
| 15 | 29.14 | 28.91 | 28.80 | 29.53 | 27.03 | 26.64 | 29.72 | 29.62 |
| 16 | 27.05 | 29.26 | 29.25 | 30.44 | 30.67 | 30.95 | 30.77 | 30.49 |
| 17 | 47.70 | 59.41 | 59.31 | 56.10 | 56.53 | 56.97 | 56.61 | 56.69 |
| 18 | 47.79 | 47.59 | 47.52 | 46.88 | 47.02 | 47.11 | 47.09 | 46.85 |
| 19 | 48.75 | 48.09 | 48.06 | 49.20 | 49.31 | 49.26 | 49.53 | 49.40 |
| 20 | 150.59 | 149.74 | 149.72 | 150.59 | 150.42 | 151.03 | 150.74 | 150.26 |
| 21 | 29.71 | 29.98 | 29.89 | 32.14 | 32.22 | 32.12 | 32.27 | 31.77 |
| 22 | 33.95 | 33.28 | 33.22 | 37.01 | 37.17 | 36.46 | 37.20 | 36.71 |
| 23 | 27.91 | 26.73 | 27.97 | 27.68 | 26.76 | 26.79 | 26.77 | 26.73 |
| 24 | 15.37 | 21.12 | 15.33 | 15.16 | 21.11 | 21.18 | 21.13 | 21.13 |
| 25 | 15.93 | 15.84 | 15.89 | 15.69 | 15.94 | 16.10 | 15.91 | 15.86 |
| 26 | 16.08 | 16.07 | 16.13 | 15.89 | 16.07 | 16.13 | 16.10 | 16.07 |
| 27 | 14.72 | 14.30 | 14.26 | 14.46 | 14.74 | 14.77 | 14.76 | 14.73 |
| 28 | 60.03 | 206.55 | 206.67 | 179.00 | 182.72 | 176.23 | 176.09 | 174.73 |
| 29 | 109.58 | 110.32 | 110.15 | 109.26 | 109.89 | 109.59 | 109.68 | 109.92 |
| 30 | 19.06 | 19.12 | 18.99 | 19.05 | 19.49 | 19.21 | 19.54 | 19.49 |
| 31 | | | | | | 37.73 | 60.79 | 79.13 |
| 32 | | | | | | 34.30 | 118.83 | 169.65 |
| 33 | | | | | | 70.47 | 142.24 | 20.84 |
| 34 | | | | | | 39.66 | 39.64 | |
| 35 | | | | | | 138.91 | 26.85 | |
| 36 | | | | | | 122.41 | 124.41 | |
| 37 | | | | | | 29.69 | 131.44 | |
| 38 | | | | | | 31.97 | 39.76 | |
| 39 | | | | | | 50.68 | 26.44 | |
| 40 | | | | | | 37.15 | 123.82 | |
| 41 | | | | | | 20.94 | 131.44 | |
| 42 | | | | | | 39.96 | 16.15 | |
| 43 | | | | | | 42.46 | 16.71 | |
| 44 | | | | | | 57.00 | 17.84 | |
| 45 | | | | | | 24.42 | 25.85 | |
| 46 | | | | | | 28.38 | | |
| 47 | | | | | | 56.34 | | |
| 48 | | | | | | 19.21 | | |
| 49 | | | | | | 12.01 | | |
| 50 | | | | | | 35.94 | | |
| 51 | | | | | | 18.89 | | |
| 52 | | | | | | 36.83 | | |
| 53 | | | | | | 23.98 | | |
| 54 | | | | | | 39.67 | | |
| 55 | | | | | | 28.17 | | |
| 56 | | | | | | 22.97 | | |
| 57 | | | | | | 22.71 | | |

| Ci | 3a-α | 3a-β | 3c-β | 4a-β* | 4c-β | 5 |
|---|---|---|---|---|---|---|
| 1 | 33.42 | 38.92 | 38.83 | | 38.01 | 39.69 |
| 2 | 25.55 | 27.61 | 27.49 | | 25.08 | 33.78 |
| 3 | 76.39 | 79.14 | 79.03 | 81.50 | 81.13 | 218.36 |
| 4 | 37.69 | 39.02 | 38.96 | | 37.53 | 47.45 |
| 5 | 49.33 | 55.47 | 55.45 | | 55.04 | 55.01 |
| 6 | 18.43 | 18.51 | 18.40 | | 17.83 | 19.75 |
| 7 | 34.36 | 34.32 | 34.45 | | 33.90 | 34.23 |
| 8 | 41.11 | 40.91 | 40.81 | | 40.36 | 40.75 |
| 9 | 50.43 | 50.67 | 50.65 | | 50.07 | 49.72 |

TABLE 1-continued $^{13}$C-NMR data

| | | | | | | |
|---|---|---|---|---|---|---|
| 10 | 37.15 | 37.15 | 37.30 | | 36.74 | 37.00 |
| 11 | 20.94 | 20.98 | 20.99 | | 20.56 | 21.52 |
| 12 | 25.90 | 25.95 | 25.61 | | 23.39 | 22.87 |
| 13 | 38.88 | 38.92 | 38.35 | | 37.84 | 38.46 |
| 14 | 42.75 | 42.68 | 42.49 | | 42.04 | 42.74 |
| 15 | 29.67 | 29.76 | 29.64 | | 29.15 | 27.00 |
| 16 | 30.98 | 31.02 | 30.51 | | 30.03 | 29.80 |
| 17 | 57.00 | 57.00 | 56.71 | | 56.20 | 56.96 |
| 18 | 47.17 | 47.14 | 46.88 | | 46.45 | 44.26 |
| 19 | 49.17 | 49.34 | 49.47 | | 48.99 | 48.79 |
| 20 | 151.17 | 151.12 | 150.33 | 150.13 | 149.73 | 29.85 |
| 21 | 32.10 | 32.15 | 31.83 | | 31.37 | 32.12 |
| 22 | 36.84 | 36.87 | 36.73 | | 36.26 | 37.52 |
| 23 | 28.17 | 28.17 | 28.09 | | 27.68 | 26.77 |
| 24 | 19.80 | 19.83 | 15.47 | | 15.61 | 21.14 |
| 25 | 22.28 | 16.25 | 16.05 | | 15.87 | 16.00 |
| 26 | 16.33 | 16.33 | 16.24 | | 16.21 | 16.04 |
| 27 | 14.93 | 14.86 | 14.81 | | 14.36 | 14.67 |
| 28 | 176.33 | 176.28 | 174.76 | 174.58 | 174.19 | 182.87 |
| 29 | 109.74 | 109.52 | 109.85 | 109.59 | 109.52 | 23.11 |
| 30 | 19.22 | 19.22 | 19.48 | | 19.02 | 14.80 |
| 31 | 37.78 | 37.81 | 79.09 | | 78.64 | |
| 32 | 28.42 | 28.42 | 169.70 | | 169.93 | |
| 33 | 70.43 | 70.45 | 20.83 | 70.32 | 20.38 | |
| 34 | 39.67 | 39.71 | | | 169.08 | |
| 35 | 138.91 | 138.91 | | | | |
| 36 | 122.41 | 122.41 | | | mPEG | |
| 37 | 32.81 | 32.84 | | | | |
| 38 | 31.97 | 31.97 | | | CH$_3$O— | |
| 39 | 50.66 | 50.67 | | | 58.66 | |
| 40 | 37.46 | 37.33 | | | | |
| 41 | 20.94 | 21.10 | | | CH$_2$ | |
| 42 | 39.95 | 39.99 | | | | |
| 43 | 42.47 | 42.47 | | | 68.37 | |
| 44 | 56.99 | 57.00 | | | 70.23 | |
| 45 | 24.42 | 24.46 | | | 70.50 | |
| 46 | 23.96 | 24.01 | | | 70.77 | |
| 47 | 56.30 | 56.32 | | | 71.58 | |
| 48 | 16.04 | 15.52 | | | | |
| 49 | 12.02 | 12.02 | | | | |
| 50 | 35.93 | 35.94 | | | | |
| 51 | 18.89 | 18.89 | | | | |
| 52 | 36.33 | 36.38 | | | | |
| 53 | 26.63 | 26.68 | | | | |
| 54 | 39.67 | 39.71 | | | | |
| 55 | 28.17 | 28.17 | | | | |
| 56 | 22.97 | 22.97 | | | | |
| 57 | 22.72 | 22.71 | | | | |
| 58 | | | | 170.29 | | |

| Ci | 6a | 6c | 7a-β | 7c-β | 8a-β* | 8c-β |
|---|---|---|---|---|---|---|
| 1 | 39.63 | 39.67 | 38.86 | 38.86 | | 38.40 |
| 2 | 33.85 | 33.79 | 27.50 | 27.54 | | 25.89 |
| 3 | 218.12 | 218.04 | 78.98 | 79.10 | 80.53 | 81.64 |
| 4 | 47.43 | 47.39 | 38.95 | 39.00 | | 37.94 |
| 5 | 55.01 | 55.00 | 55.41 | 55.45 | | 55.42 |
| 6 | 19.80 | 19.73 | 18.44 | 18.45 | | 18.23 |
| 7 | 34.25 | 34.19 | 34.25 | 34.53 | | 34.38 |
| 8 | 40.86 | 40.74 | 40.89 | 40.87 | | 40.79 |
| 9 | 49.77 | 49.74 | 50.41 | 50.45 | | 50.26 |
| 10 | 36.97 | 36.95 | 37.03 | 37.32 | | 37.13 |
| 11 | 21.60 | 21.52 | 21.04 | 21.06 | | 20.97 |
| 12 | 26.63 | 22.67 | 23.92 | 22.74 | | 23.78 |
| 13 | 38.87 | 38.22 | 38.76 | 38.22 | | 38.11 |
| 14 | 42.81 | 42.68 | 42.72 | 42.69 | | 42.61 |
| 15 | 27.24 | 26.97 | 27.23 | 27.03 | | 26.90 |
| 16 | 29.63 | 29.59 | 29.63 | 29.67 | | 29.56 |
| 17 | 57.26 | 57.09 | 57.24 | 57.19 | | 57.10 |
| 18 | 44.39 | 44.06 | 44.39 | 44.17 | | 44.09 |
| 19 | 48.72 | 48.86 | 48.76 | 48.99 | | 48.89 |
| 20 | 29.92 | 29.79 | 29.89 | 29.85 | | 29.76 |
| 21 | 32.13 | 31.64 | 32.11 | 31.78 | | 31.67 |
| 22 | 36.84 | 37.04 | 36.81 | 37.13 | | 37.10 |
| 23 | 26.77 | 26.70 | 28.11 | 28.13 | | 28.06 |
| 24 | 21.16 | 21.12 | 15.51 | 15.52 | | 16.04 |
| 25 | 16.04 | 15.87 | 16.17 | 16.13 | | 16.22 |
| 26 | 16.14 | 16.00 | 16.31 | 16.24 | | 16.59 |

TABLE 1-continued

13C-NMR data

| | | | | | | |
|---|---|---|---|---|---|---|
| 27 | 14.69 | 14.61 | 14.76 | 14.75 | | 14.63 |
| 28 | 176.41 | 174.84 | 176.42 | 174.98 | 175.18 | 174.88 |
| 29 | 23.28 | 23.04 | 23.28 | 23.10 | | 23.02 |
| 30 | 14.87 | 14.74 | 14.87 | 14.80 | | 14.72 |
| 31 | 38.04 | 79.06 | 38.04 | 79.08 | | 79.02 |
| 32 | 34.25 | 169.61 | 28.34 | 169.75 | | 169.63 |
| 33 | 70.32 | 20.80 | 70.26 | 20.88 | 69.79 | 20.79 |
| 34 | 39.75 | | 39.63 | | | 170.40 |
| 35 | 138.82 | | 138.79 | | 137.89 | |
| 36 | 122.40 | | 122.37 | | 121.46 | mPEG |
| 37 | 32.59 | | 32.63 | | | |
| 38 | 31.93 | | 31.91 | | | $CH_3O-$ |
| 39 | 50.67 | | 50.62 | | | 59.09 |
| 40 | 37.07 | | 37.24 | | | |
| 41 | 20.91 | | 20.89 | | | $CH_2$ |
| 42 | 39.93 | | 39.90 | | | |
| 43 | 42.42 | | 42.39 | | | 68.81 |
| 44 | 57.00 | | 56.97 | | | 70.46 |
| 45 | 24.39 | | 24.37 | | | 70.63 |
| 46 | 28.35 | | 26.60 | | | 70.85 |
| 47 | 56.31 | | 56.27 | | | 71.99 |
| 48 | 19.19 | | 19.17 | | | |
| 49 | 11.98 | | 11.97 | | | |
| 50 | 35.90 | | 35.88 | | | |
| 51 | 18.87 | | 18.85 | | | |
| 52 | 36.31 | | 36.30 | | | |
| 53 | 23.95 | | 23.92 | | | |
| 54 | 39.63 | | 39.63 | | | |
| 55 | 28.13 | | 28.11 | | | |
| 56 | 22.95 | | 22.94 | | | |
| 57 | 22.69 | | 22.68 | | | |
| 58 | | | | | 169.35 | |

(*not all peaks were recorded)

For the purposes of the present invention, for all the synthetic examples described above, where there are reaction conditions described, such as reagents, solvents and temperatures, above and/or below an arrow in a graphical representation, it is to be understood that these reaction conditions, in particular solvents and temperatures, are not essential to the reaction being carried out and may be varied.

Example 17

Chronic Lymphoid Leukaemia

The sensibility of human leukaemia cells to acetoxymethyl 3β-(methoxypolyethylene glycol acetoxy)-lup-20(29)-en-28-oate 4c-β at different concentrations (from 0.04 mM up to 1 mM) was tested in vitro. The lymphocytes of three patients (4266866, 4266860 and 4262311) suffering from chronic lymphoid leukaemia were used in cell cultures.

The following protocol was followed:

On day 0: A multi-well plate was prepared per patient, each comprising $10^6$ cells/well in a total volume of 1 ml. Cells, RPMI (cell growth medium) and test compound 4c-β were added in accordance with table 2 (all experiments were duplicated). The test compound dissolved in RPMI was added in the following amounts: 10 μl≡0.04 mM, 50 μl≡0.2 mM, 100 μl≡0.4 mM, 150 μl≡0.6 mM, 200 μl≡0.8 mM, and 250 μl≡1 mM.

On day 2:
- 500 μl was taken from each well of plate 1 and put into a well of plate 2.
- Plate 2: cells were tritiated with $^3$H-thymidine for 4 hours; after the 4 hours incubation in the presence of radioactivity, plate 2 was harvested and radioactivity was counted.
- Plate 1: 50 μl PHA was added to the 500 μl of each well of plate 1.

On day 5:
- Plate 1: cells and PHA were tritiated with $^3$H-thymidine for 4 hours; after the 4 hours incubation in the presence of radioactivity, plate 1 was harvested and radioactivity was counted.

TABLE 2 plate preparation

| Well | Patient 1 (4266866) | Patient 2 (4266860) | Patient 3 (4262311) |
|---|---|---|---|
| 1 (control) | 100 μl cells + 900 μl RPMI | 200 μl cells + 800 μl RPMI | 100 μl cells + 900 μl RPMI |
| 2 (control) | 100 μl cells + 900 μl RPMI | 200 μl cells + 800 μl RPMI | 100 μl cells + 900 μl RPMI |
| 3 | 100 μl cells + 890 μl RPMI + 10 μl compound 4c-β | 200 μl cells + 790 μl RPMI + 10 μl compound 4c-β | 100 μl cells + 890 μl RPMI + 10 μl compound 4c-β |
| 4 | 100 μl cells + 850 μl RPMI + | 200 μl cells + 750 μl RPMI + | 100 μl cells + 850 μl RPMI + |

TABLE 2-continued

| | plate preparation | | |
|---|---|---|---|
| Well | Patient 1 (4266866) | Patient 2 (4266860) | Patient 3 (4262311) |
| 5 | 50 µl compound 4c-β 100 µl cells + 800 µl RPMI + | 50 µl compound 4c-β 200 µl cells + 700 µl RPMI + | 50 µl compound 4c-β 100 µl cells + 800 µl RPMI + |
| 6 | 100 µl compound 4c-β 100 µl cells + 750 µl RPMI + | 100 µl compound 4c-β 200 µl cells + 650 µl RPMI + | 100 µl compound 4c-β 100 µl cells + 750 µl RPMI + |
| 7 | 150 µl compound 4c-β 100 µl cells + 700 µl RPMI + | 150 µl compound 4c-β 200 µl cells + 600 µl RPMI + | 150 µl compound 4c-β 100 µl cells + 700 µl RPMI + |
| 8 | 200 µl compound 4c-β 100 µl cells + 650 µl RPMI + 250 µl compound 4c-β | 200 µl compound 4c-β 200 µl cells + 550 µl RPMI + 250 µl compound 4c-β | 200 µl compound 4c-β 100 µl cells + 650 µl RPMI + 250 µl compound 4c-β |

Figure 2A:
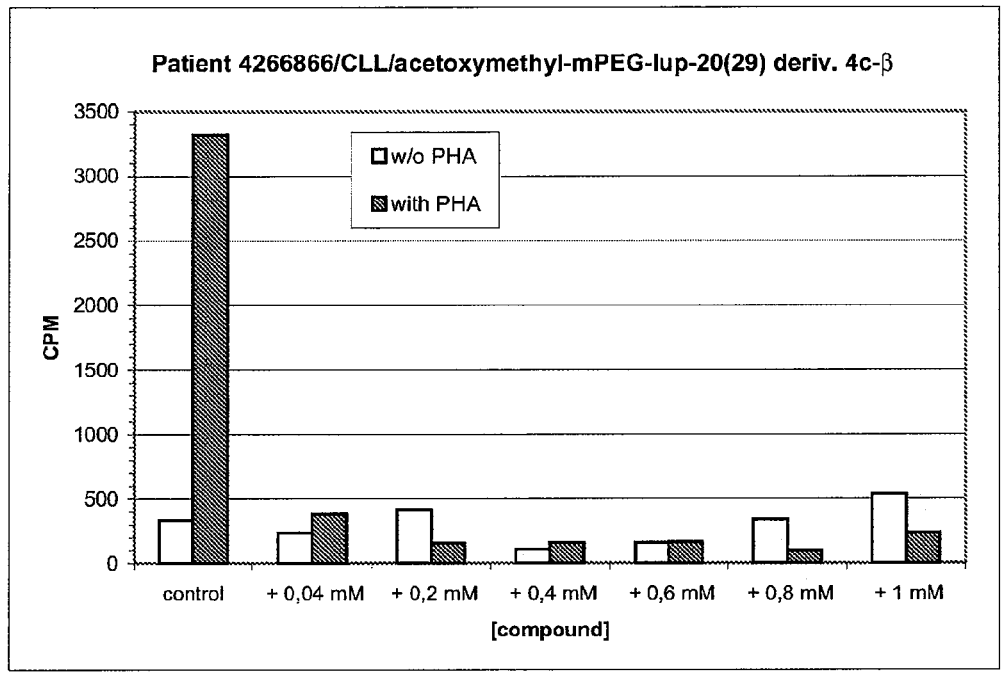
FIGS. 2a-c are graphs showing the results of treating cells of three patients suffering from chronic lymphoid leukaemia with a compound according to the present invention, compound 4c-β.
Figure 2B:
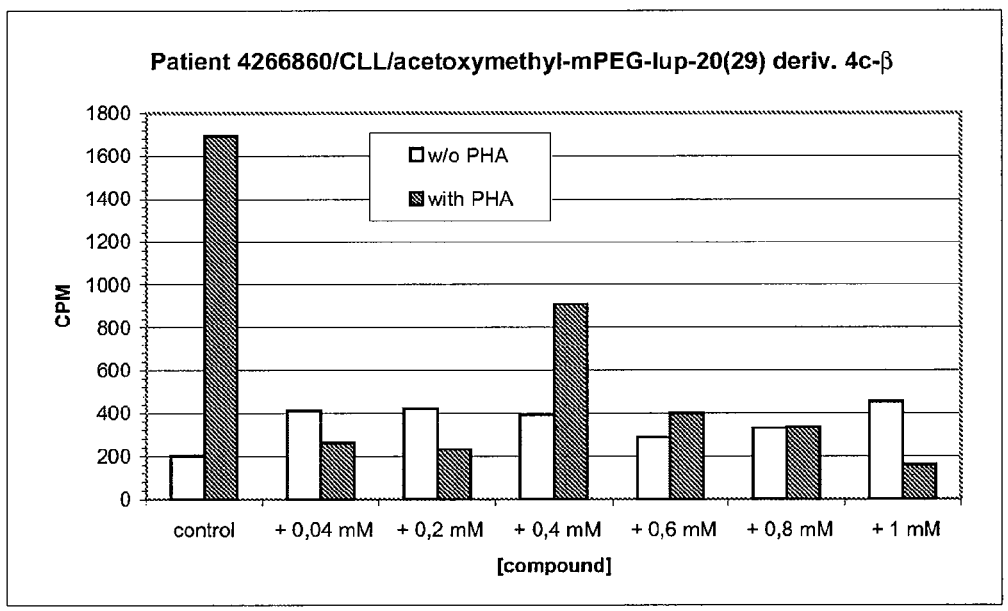
Figure 2C:
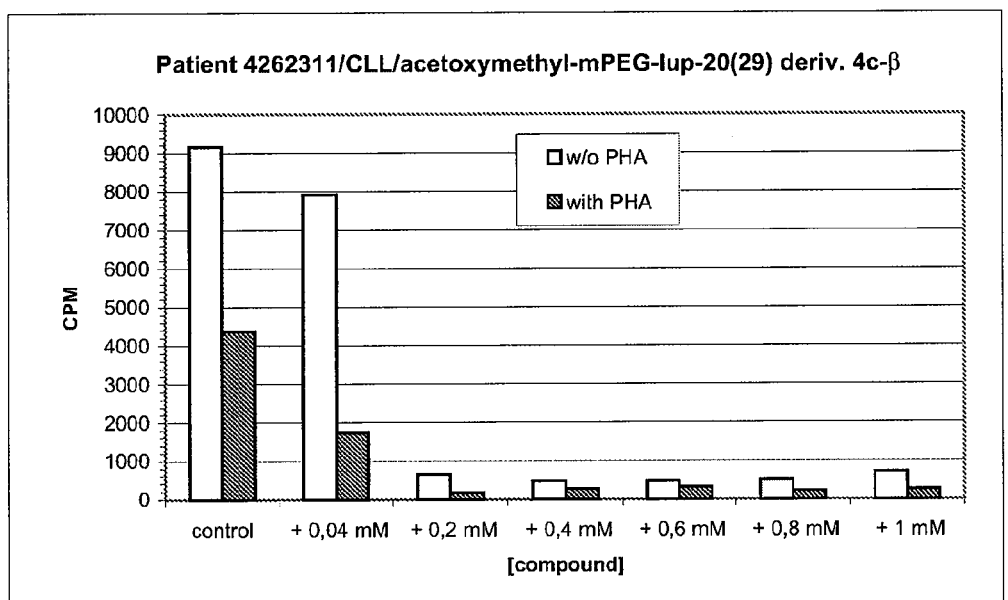

The experimental results are summarised in FIGS. 2a-c.

PHA (a lectin named phytoagglutine, which is a mitogen activating living cells) was added to the cells in culture. PHA acts as a stimulating agent. All human lymphocytes have receptors for this type of lectin and all human lymphocytes undergo lymphoblastic transformation when stimulated by PHA. By adding PHA to the cells in culture, it was possible to measure whether the cells were still alive.

CPM stands for counts per minute and measures the disintegration of the tritiated $^3$H-thymidine. Thus, CPM reflects the radioactivity of the cells' DNA having incorporated the tritiated $^3$H-thymidine after mitosis.

As can be seen from the plate 2 experiments, cells contacted with test compound 4c-β were killed within 48 hours, their death being measured by CPM after addition of tritiated $^3$H-thymidine, which is not incorporated into the cells' DNA, because the cells were unable to perform mitosis. As can be seen from the plate 1 experiments, the cells could no longer be activated by PHA.

Example 18

Chronic Lymphoid Leukaemia

The sensibility of human leukaemia cells to α-cholesteryl 3β-(methoxypolyethylene glycol acetoxy)-lup 20(29)-en-28-oate 4a-β at different concentrations (0.5 mM and 1 mM) was tested in vitro. The lymphocytes of one patient (4308840) suffering from chronic lymphoid leukaemia were used in cell cultures.

The following protocol was followed:
On day 0: A multi-well plate was prepared, comprising 10$^6$ cells/well in a total volume of 1.5 ml. Cells, RPMI (cell growth medium), PHA and test compound 4a-β were added in accordance with table 3 (all experiments were triplicated). The test compound dissolved in RPMI was added in the following amounts: 125 µl≡0.5 mM and 250 µl≡1 mM.

On day 1:
2×500 µl were taken from each well of plate 1 and put into a well of plates 2 and 3.
Plate 2: cells were tritiated with $^3$H-thymidine for 4 hours; after the 4 hours incubation in the presence of radioactivity, plate 2 was harvested and radioactivity was counted.
Plate 1: 50 µl PHA was added to the 500 µl of each well of plate 1.
On day 2:
Plate 1: cells were tritiated with $^3$H-thymidine for 4 hours; after the 4 hours incubation in the presence of radioactivity, plate 1 was harvested and radioactivity was counted.
Plate 3: cells were tritiated with $^3$H-thymidine for 4 hours; after the 4 hours incubation in the presence of radioactivity, plate 3 was harvested and radioactivity was counted.

TABLE 3

| | plate preparation |
|---|---|
| Well | Patient (4308840) |
| 1 (control) | 1 ml cells + 500 µl RPMI |
| 2 (positive control) | 1 ml cells + 450 µl RPMI + 50 µl PHA |
| 3 | 1 ml cells + 375 µl RPMI + 125 µl compound 4a-β |
| 4 | 1 ml cells + 250 µl RPMI + 250 µl compound 4a-β |

Figure 3:
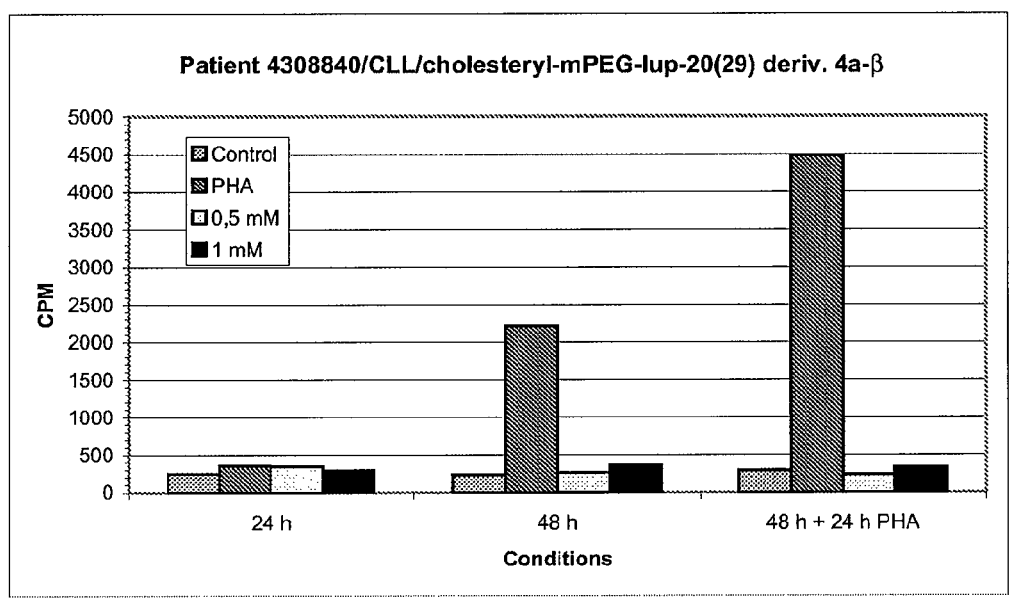
FIG. 3 is a graph showing the results of treating cells of one patient suffering from chronic lymphoid leukaemia with another compound according to the present invention, compound 4a-β.

The experimental results are summarised in FIG. 3.

As can be seen, the cells contacted with 0.5 mM and 1 mM of test compound 4a-β could not be activated by addition of PHA after 48 hours. Hence cells contacted with 0.5 mM and 1 mM of the test compound were killed within 48 hours. In contrast to this, the cells not in contact with the test compound (positive control in well 2), reacted to the addition of further PHA after 48 hours, showing that the cells were still alive.

The fact that the cancer cells died without the addition of lipase shows that hydrolysis of the test compound is not necessary to obtain a lethal effect on this type of cancer cell.

Example 19

Chronic Lymphoid Leukaemia

The sensibility of human leukaemia cells to acetoxymethyl 3β-(methoxypolyethylene glycol acetoxy)-lupan-28-oate 8c-β at different concentrations (0.5 mM and 1 mM) was tested in vitro. The lymphocytes of one patient (4316182) suffering from chronic lymphoid leukaemia were used in cell cultures.

The following protocol was followed:
On day 0: A multi-well plate was prepared, comprising 10$^6$ cells/well in a total volume of 1.5 ml. Cells, RPMI (cell growth medium), PHA and test compound 8c-β were added in accordance with table 4 (all experiments were triplicated). The test compound dissolved in RPMI was added in the following amounts: 125 µl≡0.5 mM and 250 µl≡1 mM.

On day 1:

750 μl were taken from each well of plate 1 and put into a well of plate 2.

Plate 1: 50 μl PHA was added to the 750 μl of each well of plate 1.

On day 2:

Plate 1: cells were tritiated with $^3$H-thymidine for 4 hours; after the 4 hours incubation in the presence of radioactivity, plate 1 was harvested and radioactivity was counted.

Plate 2: cells were tritiated with $^3$H-thymidine for 4 hours; after the 4 hours incubation in the presence of radioactivity, plate 2 was harvested and radioactivity was counted.

TABLE 4 plate preparation

| Well | Patient (4316182) |
|---|---|
| 1 (control) | 1 ml cells + 500 μl RPMI |
| 2 (positive control) | 1 ml cells + 450 μl RPMI + 50 μl PHA |
| 3 | 1 ml cells + 375 μl RPMI + 125 μl compound 8c-β |
| 4 | 1 ml cells + 250 μl RPMI + 250 μl compound 8c-β |

Figure 4:
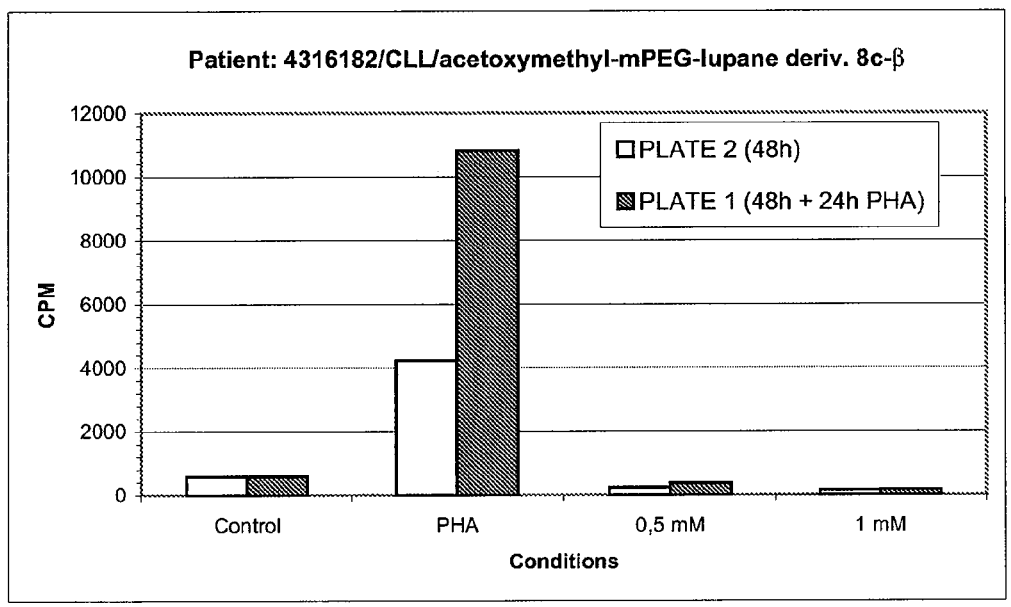
FIG. 4 is a graph showing the results of treating cells of one patient suffering from chronic lymphoid leukaemia with yet another compound according to the present invention, compound 8c-β.
Figure 5A:
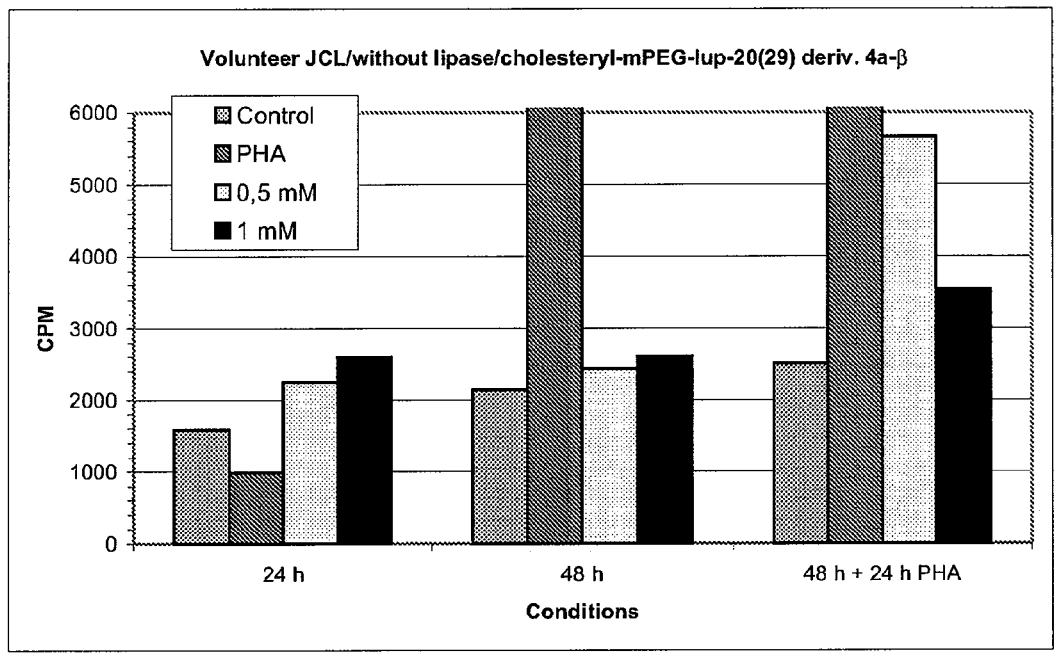
FIGS. 5a-c are graphs showing the results of treating cells of three healthy volunteers with a compound according to the present invention, compound 4a-β, in the absence of lipase.
Figure 5B:
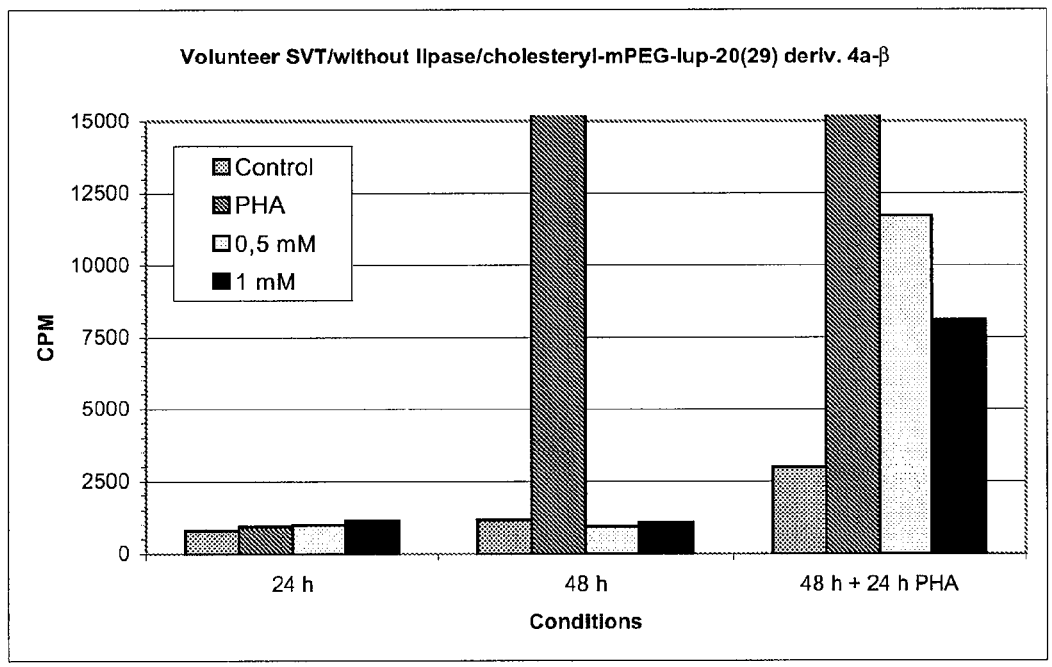
Figure 5C:
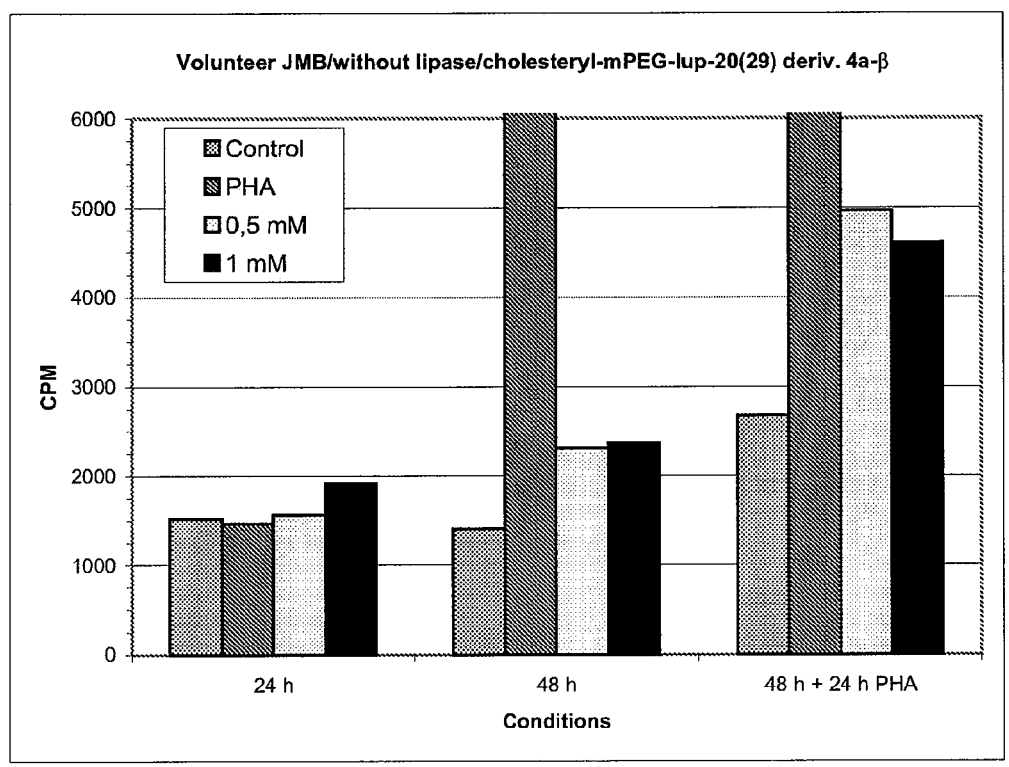
Figure 6A:
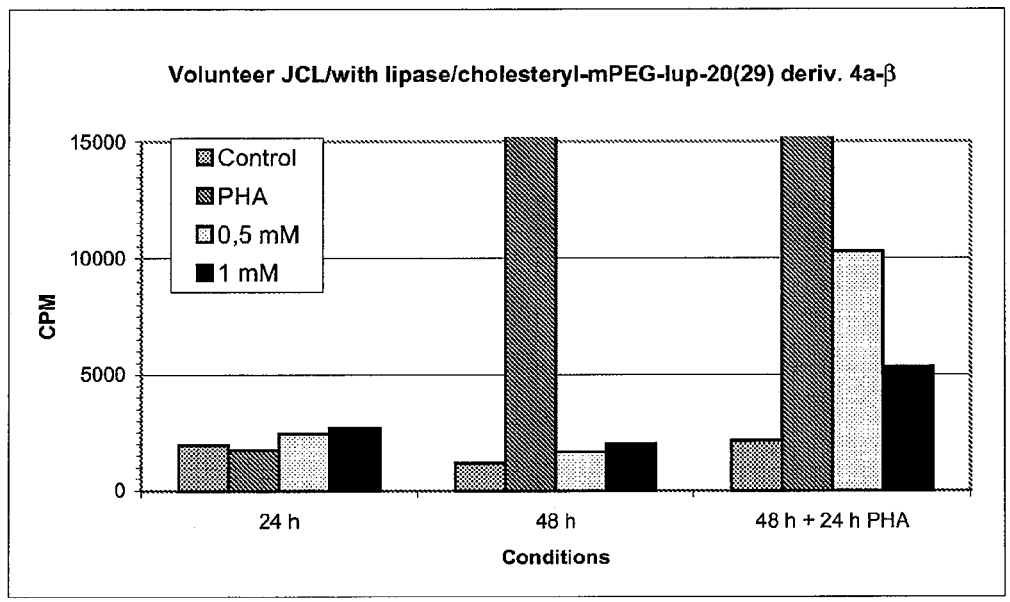
FIGS. 6a-c are graphs showing the results of treating cells of three healthy volunteers with a compound according to the present invention, compound 4a-β, in the presence of lipase.
Figure 6B:
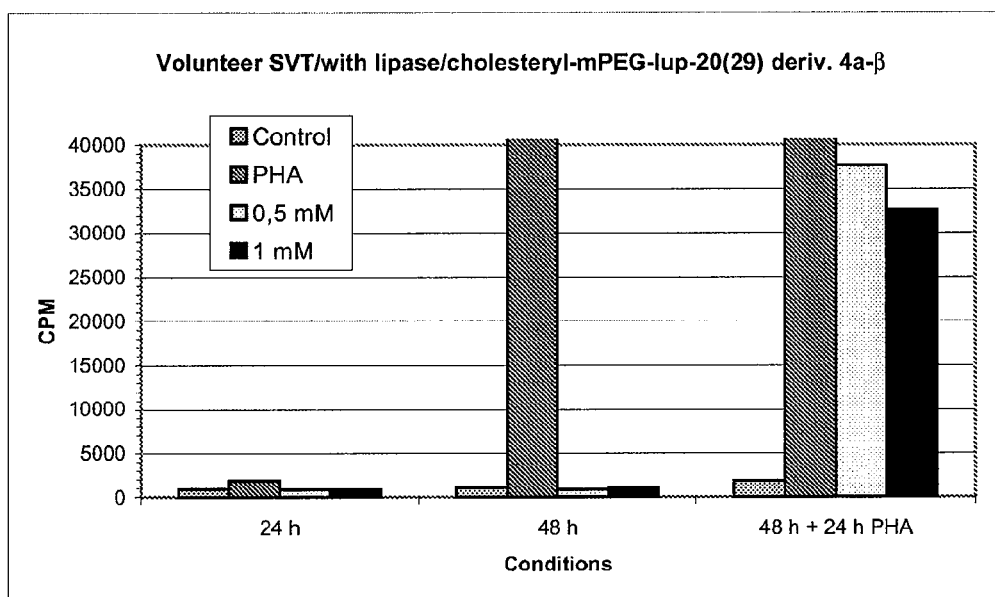
Figure 6C:
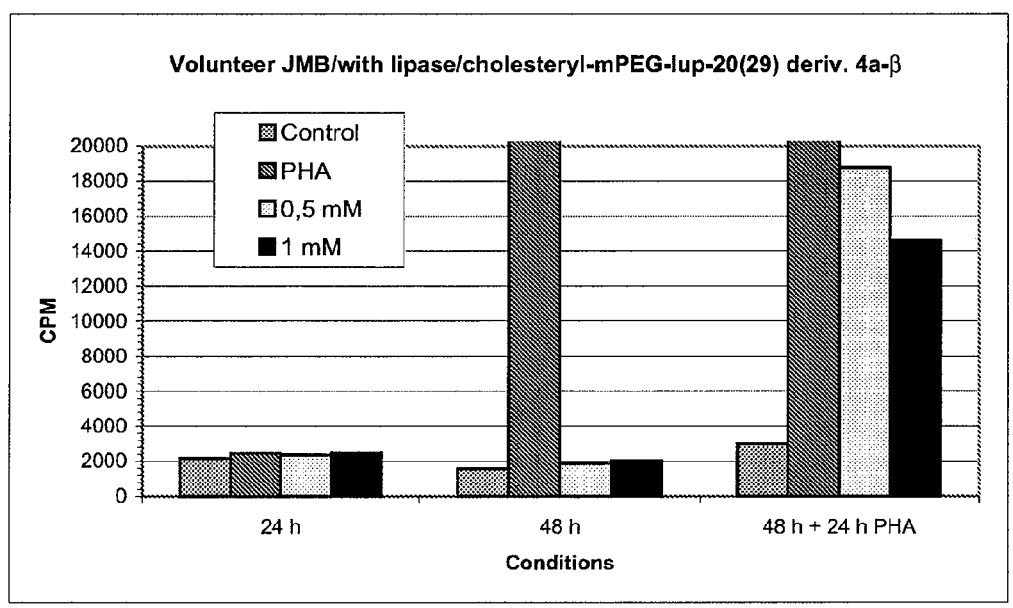

The experimental results are summarised in FIG. 4.

As can be seen, at 0.5 mM and 1 mM test compounds 8c-β killed the cells, they were unable to be reactivated by the addition of PHA. Only the cells, which were not in contact with the test compound, were still alive and could be reactivated with PHA.

Example 20

Healthy Lymphocytes

The sensibility of healthy human lymphocytes to α-cholesteryl 3β-(methoxypolyethylene glycol acetoxy)-lup-20 (29)-en-28-oate 4a-β at different concentrations (0.5 mM and 1 mM) was tested in vitro. The lymphocytes of three healthy volunteers (JCL, SVT and JMB) were used in cell cultures.

The following protocol was followed:

On day 0: A multi-well plate was prepared per volunteer, each comprising $0.5 \times 10^6$ cells/well in a total volume of 1.5 ml. Cells, RPMI (cell growth medium), PHA, lipase and test compound 4a-β were added in accordance with table 5 (all experiments were triplicated). The test compound dissolved in RPMI was added in the following amounts: 125 μl=0.5 mM and 250 μl=1 mM.

TABLE 5 plate preparation

| Plate | Volunteer 1 (JCL) | Volunteer 2 (SVT) | Volunteer 3 (JMB) |
|---|---|---|---|
| 1 (control) | 1 ml cells + 500 μl RPMI | 1 ml cells + 500 μl RPMI | 1 ml cells + 500 μl RPMI |
| 2 (control) | 1 ml cells + 450 μl RPMI + 50 μl PHA | 1 ml cells + 450 μl RPMI + 50 μl PHA | 1 ml cells + 450 μl RPMI + 50 μl PHA |
| 3 | 1 ml cells + 375 μl RPMI + 125 μl compound 4a-β | 1 ml cells + 375 μl RPMI + 125 μl compound 4a-β | 1 ml cells + 375 μl RPMI + 125 μl compound 4a-β |
| 4 | 1 ml cells + 250 μl RPMI + 250 μl compound 4a-β | 1 ml cells + 250 μl RPMI + 250 μl compound 4a-β | 1 ml cells + 250 μl RPMI + 250 μl compound 4a-β |
| 5 (control) | 1 ml cells + 470 μl RPMI + 30 μl lipase | 1 ml cells + 470 μl RPMI + 30 μl lipase | 1 ml cells + 470 μl RPMI + 30 μl lipase |
| 6 (control) | 1 ml cells + 420 μl RPMI + 30 μl lipase + 50 μl PHA | 1 ml cells + 420 μl RPMI + 30 μl lipase + 50 μl PHA | 1 ml cells + 420 μl RPMI + 30 μl lipase + 50 μl PHA |
| 7 | 1 ml cells + 345 μl RPMI + 30 μl lipase + 125 μl compound 4a-β | 1 ml cells + 345 μl RPMI + 30 μl lipase + 125 μl compound 4a-β | 1 ml cells + 345 μl RPMI + 30 μl lipase + 125 μl compound 4a-β |
| 8 | 1 ml cells + 220 μl RPMI + 30 μl lipase + 250 μl compound 4a-β | 1 ml cells + 220 μl RPMI + 30 μl lipase + 250 μl compound 4a-β | 1 ml cells + 220 μl RPMI + 30 μl lipase + 250 μl compound 4a-β |

On day 1:

2×500 μl were taken from each well of plate 1 and put into a well of plates 2 and 3.

Plate 2: cells were tritiated with $^3$H-thymidine for 4 hours; after the 4 hours incubation in the presence of radioactivity, plate 2 was harvested and radioactivity was counted.

Plate 1: 50 μl PHA was added to the 500 μl of each well of plate 1.

On day 2:
Plate 1: cells were tritiated with $^3$H-thymidine for 4 hours; after the 4 hours incubation in the presence of radioactivity, plate 1 was harvested and radioactivity was counted.
Plate 3: cells were tritiated with $^3$H-thymidine for 4 hours; after the 4 hours incubation in the presence of radioactivity, plate 3 was harvested and radioactivity was counted.

The experimental results are summarised in FIGS. 5a-c and 6a-c.

As can be seen, test compound 4a-β had no lethal effect on normal lymphocytes, since they remained alive even after 48 hours in contact with the test compound. The cells reacted positively to the addition of PHA, they remained thus alive.

The addition of lipase did not influence the results, showing that not only the pegylated test compound 4a-β, but also the hydrolysed mPEG-betulonic acid had no toxic effect on healthy lymphocytes.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of one of the formulae (IIIc-α), (IIIa-β), (IVa-α) or (IVa-β):

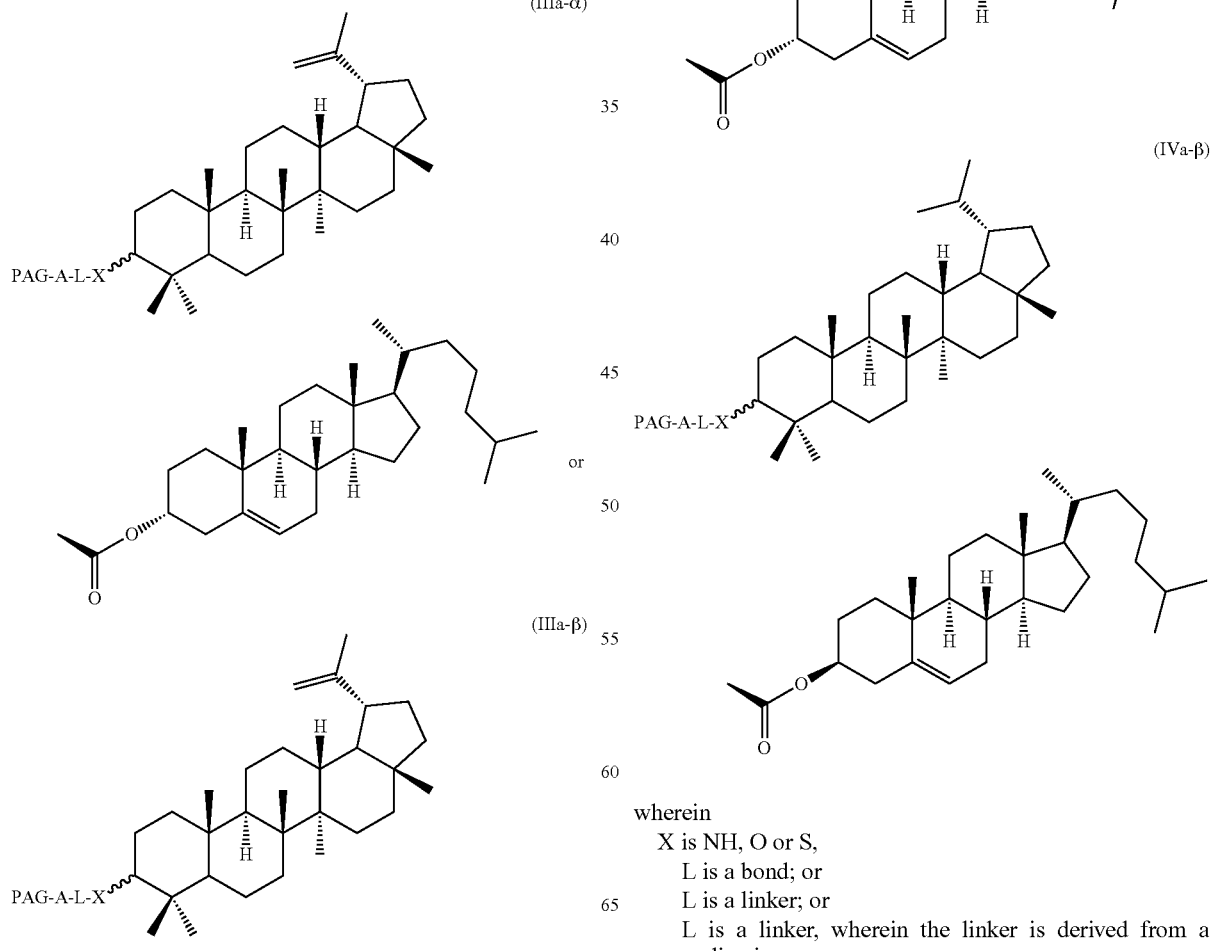

wherein
X is NH, O or S,
L is a bond; or
L is a linker; or
L is a linker, wherein the linker is derived from a diamine; or L is a linker, wherein the linker is derived from an amino acid; or L is a linker, wherein the linker is derived from lysine, glycine or ornithine; or L is a linker, wherein the linker is or forms part of a peptide, an ester or a carbonate; or the PAG-A-L-X— moiety is:

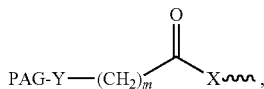

wherein Y=bond, O or NH, and m=0 to 30, wherein PAG is a poly(alkylene glycol) and X is NH, O or S; or the PAG-A-L-X— moiety is:

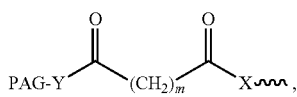

wherein Y=bond, O or NH, and m=0 to 30, wherein PAG is a poly(alkylene glycol) and X is NH, O or S; or the PAG-A-L-X— moiety is:

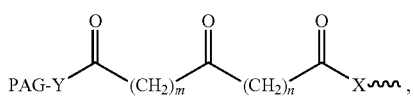

wherein Y=bond, O or NH, m=0 to 30, and n=0 to 30, wherein PAG is a poly(alkylene glycol) and X is NH, O or S; or the PAG-A-L-X— moiety is:

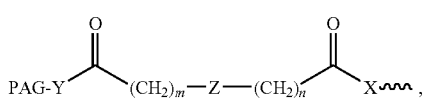

wherein Y=bond, O or NH, Z=O or NH, m=0 to 30, and n=0 to 30, wherein PAG is a poly(alkylene glycol) and X is NH, O or S; or the PAG-A-L-X— moiety is:

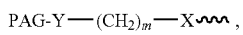

where Y=bond, O or NH, and m=0 to 30, wherein PAG is a poly(alkylene glycol) and X is NH, O or S; or the PAG-A-L-X— moiety is:

wherein Y=bond, O or NH, m=0 to 30, and n=0 to 30, wherein PAG is a poly(alkylene glycol) and X is NH, O or S; or the PAG-A-L-X— moiety is:

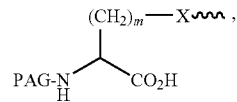

wherein m=1 to 6, wherein PAG is a poly(alkylene glycol) and X is NH, O or S; or the PAG-A-L-X— moiety is:

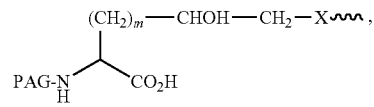

wherein m=1 to 4, wherein PAG is a poly(alkylene glycol) and X is NH, O or S; or the PAG-A-L-X— moiety is:

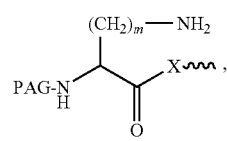

wherein m=1 to 6, wherein PAG is a poly(alkylene glycol) and X is NH, O or S; or the PAG-A-L-X— moiety is:

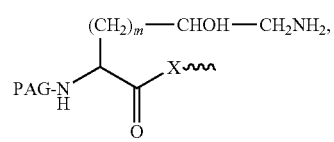

wherein m=1 to 4, wherein PAG is a poly(alkylene glycol) and X is NH, O or S; or the PAG-A-L-X— moiety is:

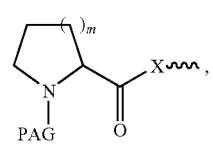

wherein m=1 or 2, wherein PAG is a poly(alkylene glycol) and X is NH, O or S; or the PAG-A-L-X— moiety is:

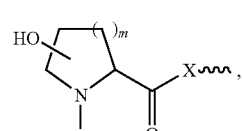

wherein m=1 or 2, wherein PAG is a poly(alkylene glycol) and X is NH, O or S; or the PAG-A-L-X— moiety is:
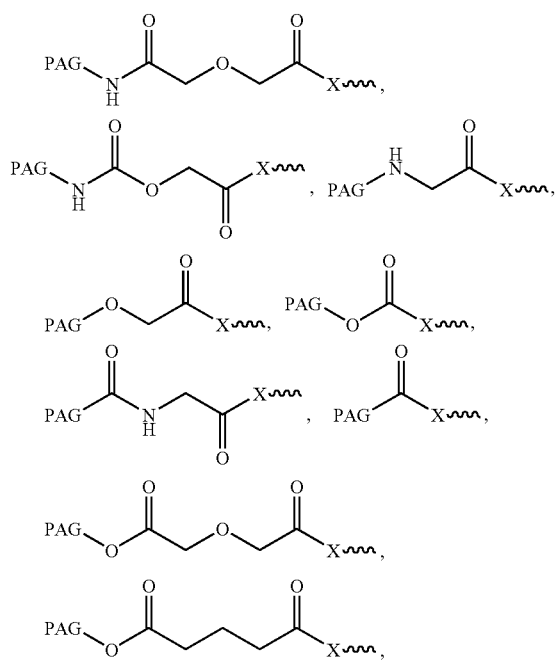
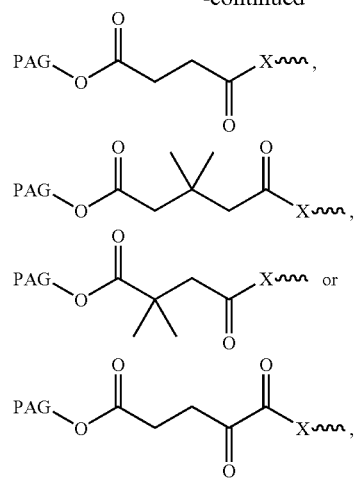
wherein PAG is a poly(alkylene glycol) and X is NH, O or S;
or
A is —O—CO—; or
the poly(alkylene glycol) is poly(ethylene glycol); or
the poly(ethylene glycol) is monomethoxy poly(ethylene glycol).
2. A compound of the structure, wherein:
(a) the compound is one of the formulae (III-α), (IIIb-β), (IVb-α) or (IVb-β):
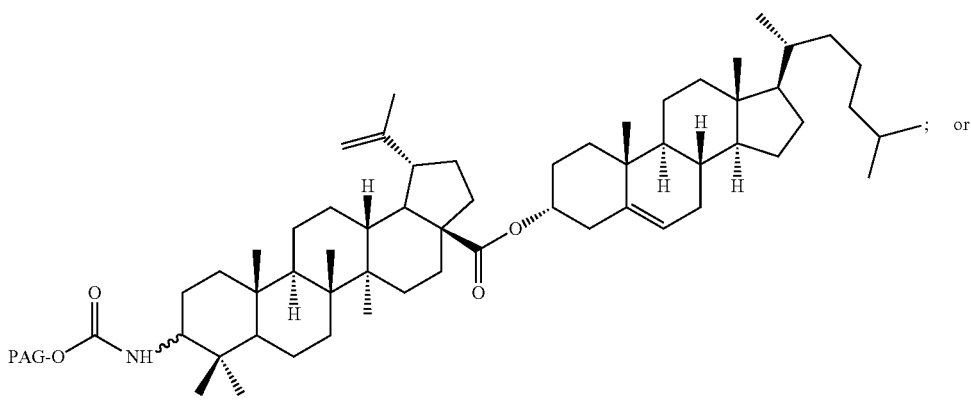
(IIIb-α)
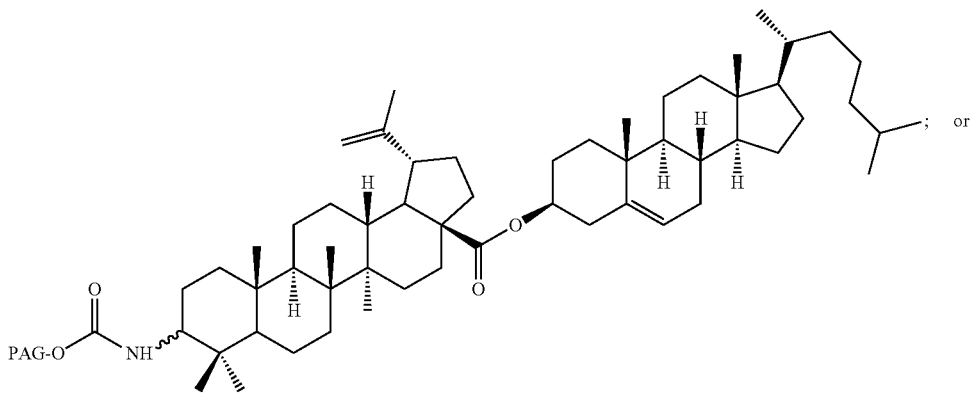
(IIIb-β)

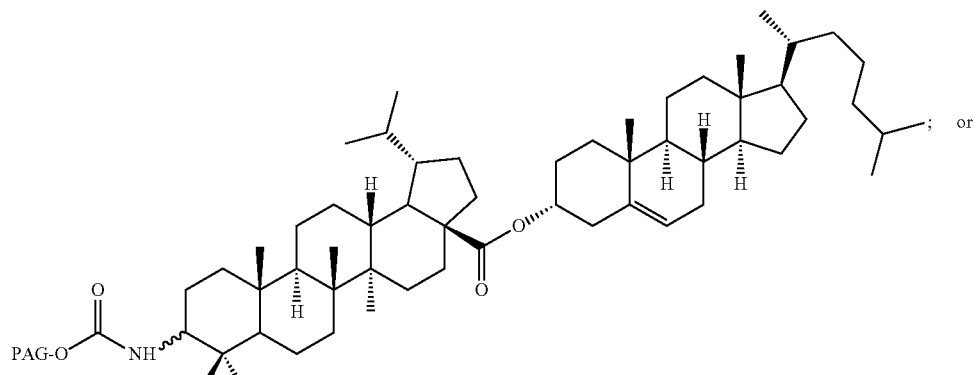
(IVb-α)
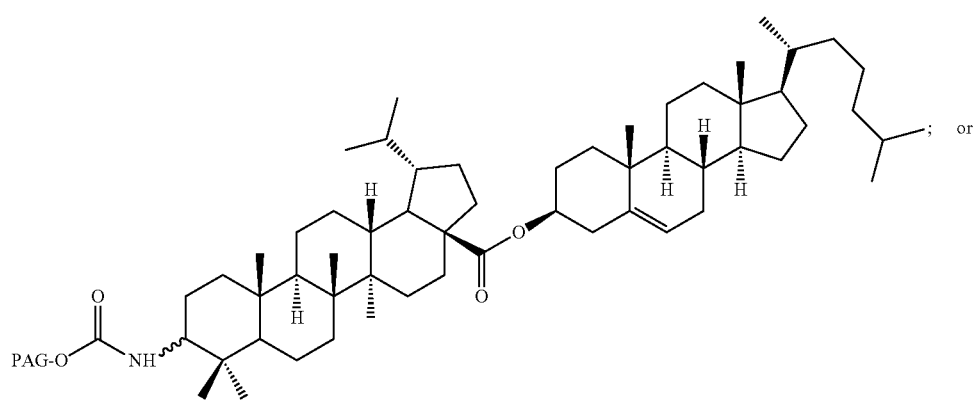
(IVb-β)
or
(b) the compounds of one of the formulae (IIIc-α), (IIIc-β), (IVc-α) or (IVc-β):
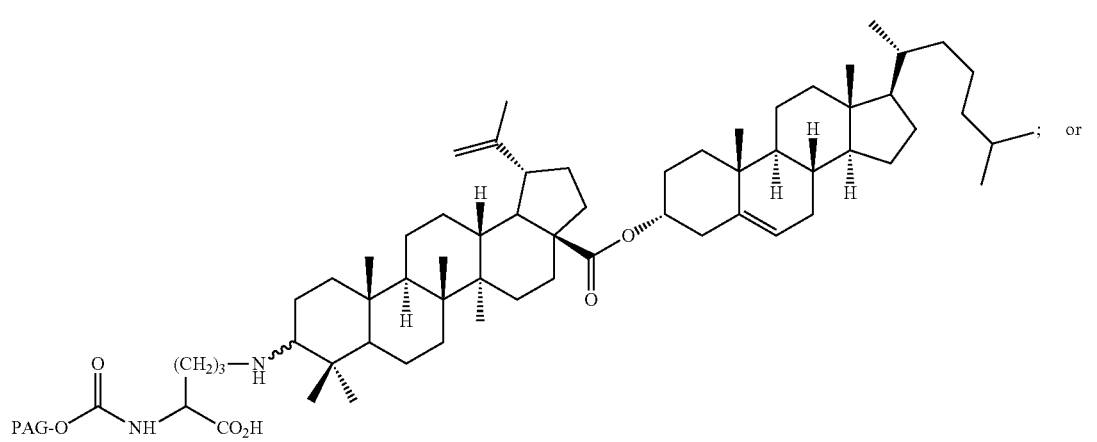
(IIIc-α)
or

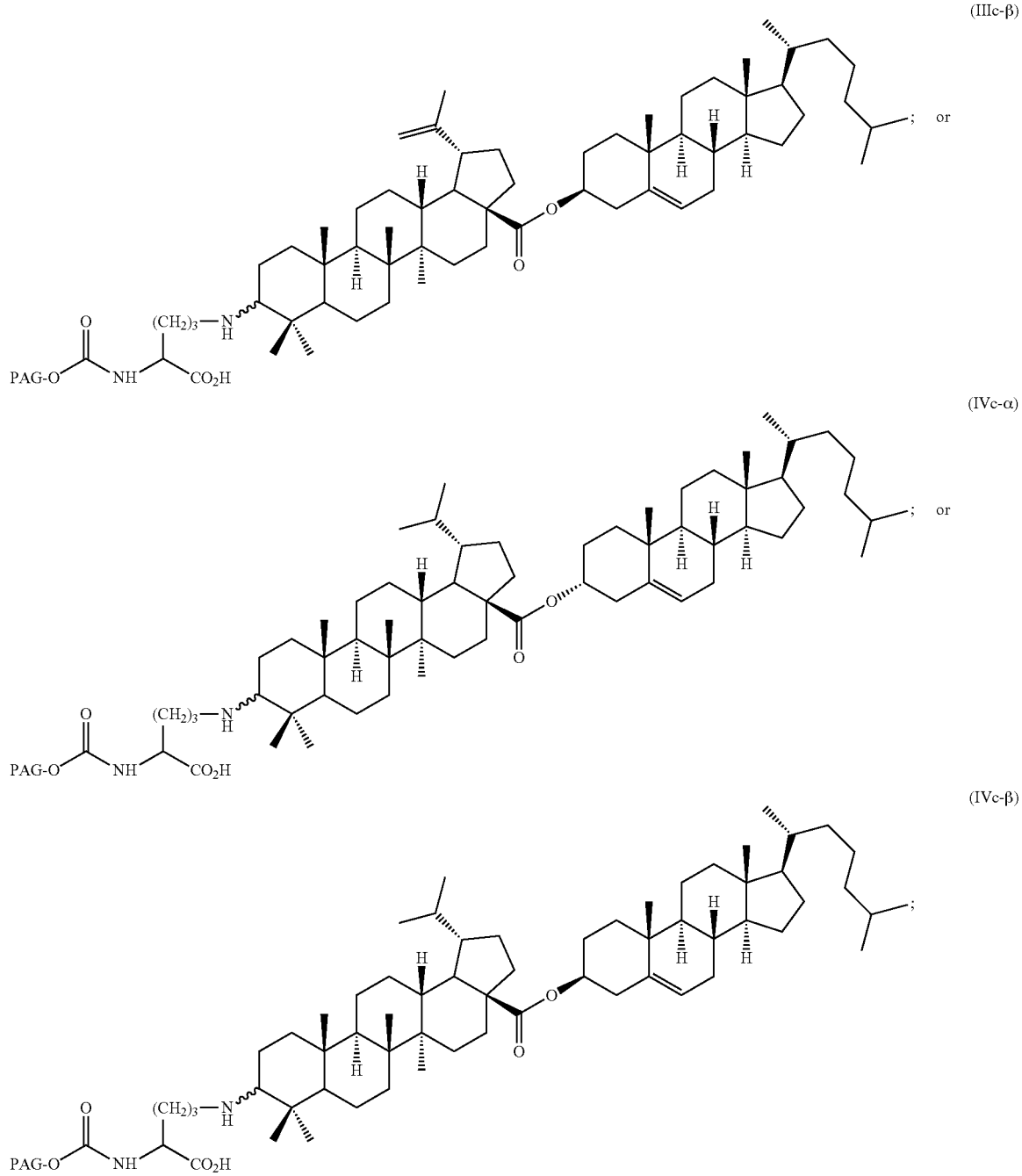

wherein PAG is a poly(alkylene glycol).

3. A method to treat leukaemia comprising administering a therapeutically effective amount of any of the compounds of claim 1.

4. A pharmaceutical composition comprising a compound as claimed in claim 1 and a pharmaceutically acceptable carrier or diluent, optionally further comprising PEG-albumin or a liposome.

5. A pharmaceutical composition comprising a compound as claimed in claim 2 and a pharmaceutically acceptable carrier or diluent, optionally further comprising PEG-albumin or a liposome.

6. A method to treat leukaemia comprising administering a therapeutically effective amount of any of the compounds of claim 2 to a subject in need thereof.

* * * * *